(12) United States Patent
Song et al.

(10) Patent No.: US 6,399,627 B1
(45) Date of Patent: Jun. 4, 2002

(54) INHIBITORS OF FACTOR XA

(75) Inventors: Yonghong Song, Foster City; Bing-Yan Zhu, Belmont; Robert M. Scarborough, Half Moon Bay; Lane Clizbe, Redwood City; Zhaozhong Jon Jia, South San Francisco; Ting Su, Belmont; Willy Teng, San Francisco, all of CA (US)

(73) Assignee: Cor Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/501,371

(22) Filed: Feb. 11, 2000

Related U.S. Application Data
(60) Provisional application No. 60/119,640, filed on Feb. 11, 1999.

(51) Int. Cl.$^7$ ........................ A61K 31/47; C07D 217/02
(52) U.S. Cl. .................. 514/307; 514/252.12; 514/315; 514/346; 514/617; 546/146; 546/248; 546/293; 544/358; 564/161
(58) Field of Search ................................ 546/146, 248, 546/293; 514/307, 346, 315, 252.12, 617; 544/358; 564/161

(56) References Cited

U.S. PATENT DOCUMENTS 4,588,587 A 5/1986 Gasic ........................... 424/95

FOREIGN PATENT DOCUMENTS

| WO | WO 94/13693 | 6/1994 |
| WO | 98/28269 | 7/1998 |
| WO | 98/28282 | 7/1998 |
| WO | 98/57934 | 12/1998 |

OTHER PUBLICATIONS

Chemical Abstracts, vol. 59, No. 3, Abstract No. 3857h, Aug. 5, 1963.*
Claeson, G. "Synthetic Peptides and Peptidomimetics as Substrates and Inhibitors of Thrombin and Other Proteases in the Blood Coagulation System", *Blood Coag. Fibrinol.*, 5, pp. 411–436 (1994).
Davie, E.J. et al., "The Coagulation Cascade: Initiation, Maintenance and Regulation", *Biochemistry*, 30, pp. 10363–10370 (1991).
Etingin, O.R., et al., "Viral Activation of the Coagulation Cascade: Molecular Interactions at the Surface of Infected Endothelial Cells", *Cell*, 61, pp. 657–662 (1990).
Furie, B., et al., "The Molecular Basis of Blood Coagulation", *Cell*, 53, pp. 505–518 (1988).
Girard, T.J. et al., "Functional Significance of the Kunitz–type Inhibitory Domains of Lipoprotein–associated Coagulation Inhibitor", *Nature*, 338, pp. 518–520 (1989).
Hoover, R.J., et al., "The Adhesive Interaction Between Polymorphonuclear Leukocytes and Endothelial Cells in Vitro", *Cell*, 14, pp. 423–428 (1978).
Tidwell, R.R. et al., "Strategies for Anticoagulation With Synthetic Protease Inhibitors. Xa Inhibitors Versus Thrombin Inhibitors", *Thromb. Res.*, 19, pp. 339–349 (1980).
R. Kuhn, et al., "Addition von Maleinsäure–anhydrid an Polyene.(Über konjugierte Dopplebindungen, XIV.)", *Berichte Der Deutschen Chemischen Gesellschaft*, vol. 63, pp. 2662–2679, (1930).
P. H. G. op het Veld, et al., "Synthetic and Mechanistic aspects of the Photocyclization of 2–(beta–arylvinyl)biphenyls into 9–aryl–9, 10–dihydrophenanthrenes", *Journal of the Chemical Society, Perkin Transactions 2*, No. 9, pp. 915–922, (1978).
W. E. Bachmann, et al., "Reduction by Magnesium and Magnesium Halide. XII. The reaction between Epoxy Ketones and Grignard Reagents", *Journal of the American Chemical Society*, vol. 56, No. 7, pp. 1559–1560, (1934).
V. N. Listvyan, et al., "(p–Benzoylbenzylidene) Triphenylphosphorane and its Application for the Preparation of Unsaturated Benzophenone Derivatives by the Wittig Reaction", *Journal of General Chemistry USSR*, vol. 50, No. 7, part 1, Jul. 1980, pp. 1231–1235, XP002161033.
D. Hellwinkel, et al., "Einfache Synthesen von 1, 2–Diaryl–und Triarylethenen mit Trägergebundenen Fluoridbasen", *Synthesis*, No. 9, pp. 973–978, (1994).
S. A. Vartanyan, et al., "Synthesis of 1, 1–diaryl–2–haloethanes and Some of Their Reactions", pp. 396, Chemical Abstracts, vol. 78, No. 13, Apr. 2, 1973, abstract No. 83924p, XP002161034.

\* cited by examiner

*Primary Examiner*—Zinna Northington Davis
(74) *Attorney, Agent, or Firm*—Morgan, Lewis & Bockius LLP

(57) ABSTRACT

Novel compounds, their salts and compositions related thereto having activity against mammalian factor Xa are disclosed. The compounds are useful in vitro or in vivo for preventing or treating coagulation disorders.

25 Claims, No Drawings

INHIBITORS OF FACTOR XA

CROSS REFERENCE TO RELATED APPLICATIONS

This application claims priority to U.S. Provisional Patent Application No. 60/119,640, filed on Feb. 11, 1999, which is herein incorporated in its entirety by reference.

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., Thromb. Res. 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, Haementeria officinalis. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988). Another potent and highly specific inhibitor of Factor Xa, called tick anticoagulant peptide (TAP), has been isolated from the whole body extract of the soft tick Ornithidoros moubata, as reported by Waxman, L., et al., "Tick Anticoagulant Peptide (TAP) is a Novel Inhibitor of Blood Coagulation Factor Xa" Science, 248, 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 22, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal $C(=NH)-NH_2$ group; WO 97/21437 describes benzimidazole compounds substituted by a basic radical which are connected to a naphthyl group via a straight or branched chain alkylene, $-C(=O)$ or $-S(=O)_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In a preferred embodiment, the present invention provides a compound of the formula I:

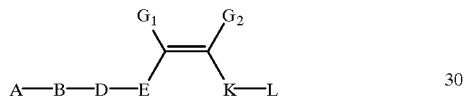

wherein:

A is selected from:
- (a) phenyl, which is independently substituted with 0–2 R substituents;
- (b) naphthyl, which is independently substituted with 0–2 R substituents; and
- (c) an aromatic or non-aromatic monocyclic heterocyclic ring system having from 5 to 8 ring atoms, wherein 1–4 ring atoms of the ring system are selected from N, O and S, and wherein the ring system may be substituted with 0–2 R substituents;

R is selected from:
halo, —$C_{1-4}$alkyl substituted by up to 4 of the same or different halogen atoms selected independently from the group consisting of chlorine, bromine, iodine and fluorine atoms, —$C_{1-4}$alkyl, —$C_{1-4}$alkyl-phenyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_m NR^1R^2$, —$SO_2NR^1R^2$, —$SO_2R^1$, —C(=O)—$NR^1R^2$, —$CF_3$, —$OR^1$, and a 5–6 membered aromatic heterocyclic system containing from 1–4 heteroatoms selected from N, O and S, wherein from 1–4 hydrogen ring atoms on the aromatic heterocyclic system, or on the phenyl portion of the —$C_{1-4}$alkyl-phenyl group, may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$NH_2$; —N(—$C_{1-4}$alkyl, —$C_{0-4}$alkyl), and —$NO_2$;

$R^1$ and $R^2$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —C(=O)—OH, —C(=O)—O—$C_{1-6}$alkyl, —C(=O)—$NH_2$, —C(=O)—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$NH_2$; —N(—$C_{1-4}$alkyl, —$C_{0-4}$alkyl), and —$NO_2$;

m is an integer of 0–2;

B is a member selected from the group consisting of:
a direct link, —C(=O)—, —N($R^3$)—, —C(—$R^{3a}$, —$R^{3b}$)—, —C(=O)—N($R^3$)—, —N($R^3$)—C(=O)—, —$SO_2$—, —O—, —$SO_2$—N($R^3$)— and —N($R^3$)—$SO_2$—;

$R^3$, $R^{3a}$ and $R^{3b}$ are each independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$;

D is a member selected from the group consisting of:
- (a) phenyl, which is independently substituted with 0–2 $R^a$ substituents; and
- (b) an aromatic six-membered heterocyclic ring having from 1–2 ring nitrogen atoms, and wherein the ring atoms may be substituted with 0–2 $R^a$ substituents;

$R^a$ is selected from:
halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_n NR^{1a}R^{2a}$, —$SO_2NR^{1a}R^{2a}$, —$SO_2R^{1a}$, —$CF_3$, —$SR^{1a}$, —$OR^{1a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

n is an integer of 0–2;

$R^{1a}$ and $R^{2a}$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

$G^1$ and $G^2$ are each independently a member selected from the group consisting of:
hydrogen, halo, —$C_{1-6}$alkyl, haloalkyl, —CN, —NO2, —$C_{2-6}$alkenyl, —$C_{2-6}$alkynyl, —$C_{3-8}$cycloalkyl, —$C_{0-4}$alkyl-$C_{3-8}$-cycloalkyl, —$C_{0-4}$alkyl-CN, —$C_{0-4}$alkyl-$NO_2$, —$C_{0-4}$alkyl-O—$R^4$, —$C_{0-4}$alkyl-S—$R^4$, —$C_{0-4}$alkyl-S(=O)$_2$—$R^4$, —$C_{0-4}$alkyl-S(O)—$R^4$, —$C_{0-4}$alkyl-C(=O)—$OR^4$, —$C_{0-4}$alkyl-C(=O)—N($R^{4a}$,$R^{4b}$), —$C_{0-4}$alkyl-C(=O)—$R^4$, —$C_{0-4}$alkyl-N($R^{4a}$,$R^{4b}$), —$C_{0-4}$alkyl-N(—$R^{4a}$)—C(=O)—$R^{4b}$), —$C_{0-4}$alkyl-N(—$R^{4a}$)—C(=O)—$R^{4b}$), —$C_{0-4}$alkyl-N(—$R^{4a}$)—C(=O)—N(—$R^{4b}$), —$C_{0-4}$alkyl-N(—$R^{4a}$)—C(=O)—N(—$R^{4b}$), —$C_{0-4}$alkyl-N(—$R^{4a}$)—S(=O)$_2$—$R^{4b}$, —$C_{0-4}$alkyl-S(=O)$_2$—N($R^{4a}$,$R^{4b}$), —$C_{0-4}$alkyl-S(=O)$_2$—$R^4$, —$C_{0-4}$alkyl-P(=O)(—$OR^{4a}$)(—$OR^{4b}$), —$C_{0-4}$alkyl-N(—$R^4$)—P(=O)(—$OR^{4a}$)(—$OR^{4b}$), —$C_{0-4}$alkyl-phenyl, —$C_{0-4}$alkyl-naphthyl, —$C_{0-4}$alkyl-heterocyclic ring system containing from 1–4 heteroatoms selected from the group consisting of O, N and S, wherein the heterocyclic ring system is a 5–6 membered monocyclic ring or a 8–12 membered bicyclic ring, and wherein 0–4 hydrogen atoms of the phenyl ring, the naphthyl ring carbon and the heterocyclic ring system are replaced by a member selected from the group consisting of —$C_{1-4}$alkyl, haloalkyl, halo, —CN, —$NO_2$, —$OR^{4c}$, —$SR^{4c}$, —S(O)$R^{4c}$, —C(=O)—$OR_{4c}$, —C(=O)—N($R^{4c}$, $R^{4d}$), —C(=O)—$R^{4c}$, —N($R^{4c}$,$R^{4d}$), —N(—$R^{4c}$)—C(=O)—$R^{4d}$, —N(—$R^{4c}$)—C(=O)—$OR^{4d}$, —N(—$R^{4c}$)—C(=O)—N(—H, $R^{4d}$), —N(—$R^{4c}$)—$SO_2$—$R^{4d}$, —$SO_2$—N(—$R^{4c}$, $R_{4d}$), —$SO_2$—$R^{4c}$; or G1 and a nitrogen on the E group can combine to form a 5–7 membered heterocyclic ring containing a 0–3 additional heteroatoms selected from the group consisting of O, N and S;

$R^4$, $R^{4a}$, $R^{4b}$, $R^{4c}$ and $R^{4d}$ are each independently a member selected from the group consisting of:
H, halo —$C_{1-6}$alkyl, —$C_{2-6}$alkenyl, —$C_{2-6}$alkynyl, —$C_{3-8}$cycloalkyl, —$C_{0-4}$alkyl-$C_{3-8}$cycloalkyl, —$CH_2CH_2OH$, —$CH_2CH_2$—O—$CH_3$, —$C_{0-4}$alkylphenyl, —$C_{0-4}$alkylheterocycle wherein the heterocycle may be a 5–6 membered ring, and wherein from 0–4 hydrogen atoms from the ring atoms of the phenyl and heterocycle groups may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl-$C_{3-8}$cycloalkyl, —CN, —$NO_2$, —C(=O)—OH, —C(=O)—O—$C_{1-4}$alkyl, —C(=O)—$NH_2$, —C(=O)—N(—H, —C1-4alkyl), and —C(=O)—N(—$C_{1-4}$alkyl, —$C_{1-4}$alkyl);
alternatively, $R^{4a}$ taken with $R^{4b}$ or $R^{4c}$ taken with $R^{4d}$ when either pair of groups is attached to the same nitrogen atom may combine with that nitrogen atom to form a 5–8 membered saturated, partially saturated or unsaturated ring which contains from 0–1 additional heteroatoms selected from a group consisting of —N, —O, S, wherein any S ring atom may be present as a —S—, —S(=O)— or —S(=O)$_2$— group;

E is a member selected from the group consisting of:
a direct link, —C(=O)—, —C(=O)—N($R^5$)—, —N($R^5$)—C(=O)—, —S(=O)$_2$—N($R^5$)—, —$CH_2$—O—, —$CH_2$—S—, —$CH_2$—S(=O)—, —$CH_2$—S(=O)$_2$—, —$CH_2$—N(—$R^5$)—, —C(—$R^{5a}$,—$R^{6a}$)— and —(—C(—$R^{5b}$,—$R^{6b}$)—C(—$R^{5c}$,—$R^{6c}$)—;
wherein $R^5$, $R^6$, $R^{5a}$, $R^{6a}$, $R^{5b}$ $R^{6b}$, $R^{5c}$ and $R^{6c}$ are each independently selected from:
H, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$alkyl, —CN and —$NO_2$;

K is a member selected from the group consisting of:
(a) phenyl, which is independently substituted with 0–2 $R^b$ substituents;
(b) naphthyl, which is independently substituted with 0–2 $R^b$ substituents; and
(c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^b$ substituents;

$R^b$ is a member selected from the group consisting of:
halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $NR^{1b}R^{2b}$, $SO_2NR^{1b}R^{2b}$, $SO_2R^{1b}$, $CF_3$, $OR^{1b}$, O—$CH_2$—$CH_2$—$OR^{1b}$, O—$CH_2$—$COOR^{1b}$, N($R^{1b}$)—$CH_2$—$CH_2$—$OR^{1b}$, N(—$CH_2$—$CH_2$—$OR^{1b}$)$_2$, N($R^{1b}$)—C(=O)$R^{2b}$, N($R^{1b}$)—$SO_2$—$R^{2b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{1b}$ and $R^{2b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

L is selected from:
H, —CN, C(=O)$NR^{12}R^{13}$, $(CH_2)_nNR^{12}R^{13}$, —C(=$NR^{12}$)$NR^{12}R^{13}$, —CH=N—N(—$R^{12}$)—C(=$NR^{12a}$, —N(—$R^{12b}$,—$R^{12c}$), —$OR^{12}$, —$NR^{12}$C(=$NR^{12}$)$NR^{12}R^{13}$, and $NR^{12}$C(=$NR^{12}$)—$R^{13}$;
$R^{12}$, $R^{12a}$, $R^{12b}$, $R^{12c}$ and $R^{13}$ are independently selected from:

hydrogen, —OR$^{14}$, —NR$^{14}$R$^{15}$, C$_{1-4}$alkyl, C$_{0-4}$alkylphenyl, C$_{0-4}$alkylnaphthyl, COOC$_{1-4}$ alkyl, COO—C$_{0-4}$alkylphenyl and COO—C$_{0-4}$ alkylnaphthyl, wherein from 1–4 hydrogen atoms on the ring atoms of the phenyl and naphthyl moieties may be independently replaced with a member selected from the group consisting of halo, —OH, —O—C$_{1-4}$alkyl, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN, and —NO$_2$;

R$^{14}$ and R$^{15}$ are independently selected from: H, C$_{1-4}$alkyl, —C(=O)—O—C$_{0-6}$alkyl, —C(=O)—NH$_2$, —C(=O)—N(—H, —C$_{1-6}$ alkyl) —C(=O)—N(—C$_{1-6}$alkyl, —C$_{1-6}$ alkyl), —C(=O)—N(—H, —C$_{1-6}$alkyl-N(— C$_{1-6}$alkyl, —C$_{1-6}$alkyl)), —C(=O)—N(—C$_{1-6}$ alkyl, —C$_{1-6}$alkyl-N(— C$_{1-6}$alkyl, —C$_{1-6}$ alkyl)), —C(=O)—([N,N]-piperazino-C$_{1-6}$ alkyl), —C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, —C$_{1-4}$alkyl, —C$_{2-6}$ alkenyl, —C$_{2-6}$alkynyl, —C$_{3-8}$cycloalkyl, —C$_{0-4}$alkylC$_{3-8}$cycloalkyl, —CN, —NO$_2$, and —COO—C$_{0-4}$alkyl;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "C$_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from lower alkoxy, lower alkyl, lower alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, lower alkylphenyl, naphthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a cyclohexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more than 1 O or S ring atoms in the same ring of a given heterocyclic ring structure.

Examples of monocyclic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimnidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In a preferred embodiment, the present invention provides a compound according to the formula I:

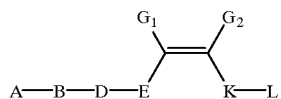

wherein:

A is selected from:
(a) phenyl, which is independently substituted with 0–2 R substituents;
(b) naphthyl, which is independently substituted with 0–2 R substituents; and
(c) an aromatic or non-aromatic monocyclic heterocyclic ring system having from 5 to 8 ring atoms, wherein 1–4 ring atoms of the ring system are selected from N, O and S, and wherein the ring system may be substituted with 0–2 R substituents;

R is selected from:
halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_m NR^1 R^2$, —$SO_2 NR^1 R^2$, —C(=O)—$NR^1 R^2$, —$SO_2 R^1$, —$CF_3$, —$OR^1$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl and —$NO_2$; A-B-D-E K-L $R^1$ and $R^2$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —C(=O)—OH, —C(=O)—O—$C_{1-6}$alkyl, —C(=O)—$NH_2$, —C(=O)—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$–$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$NH_2$; —N(—$C_{1-4}$alkyl, —$C_{0-4}$alkyl), and —$NO_2$;

m is an integer of 0–2;

B is a direct link;

D is a member selected from the group consisting of:
(a) phenyl, which is independently substituted with 0–2 $R^a$ substituents; and
(b) an aromatic six-membered heterocyclic ring having from 1–2 ring nitrogen atoms, and wherein the ring atoms may be substituted with 0–2 $R^a$ substituents;

$R^a$ is selected from:
halo, —$CF_3$, —$CHF_2$, —$CH_2$—F, —$SR^{1a}$ and —$OR^{1a}$;

$R^{1a}$, in each occurrence, is independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$G^1$ and $G^2$ are each independently selected from hydrogen or $R^4$;

$R^4$ is independently a member selected from the group consisting of:
F; Br; Cl; —CN; —$NO_2$; —$C_{1-6}$alkyl; —O—$C_{1-6}$alkyl; —$C_{1-4}$alkyl substituted by up to 4 of the same or different halogen atoms independently selected from the group consisting of F, Br, and Cl; —$C_{3-8}$ cycloalkyl substituted by up to 6 of the same or different halogen atoms independently selected from the group consisting of F, Br, and Cl; phenyl; pyridyl; pyrimidyl; imidazolyl; pyrrolyl; furanyl; thiophenyl; tetrazolyl; pyrazolyl; oxazolyl; isoxazolyl; —O—$C_{1-4}$alkyl; —N(—H)—C(=O)—$C_{1-6}$ alkyl; —N(—H)—C(=O)-phenyl; methoxycarbonylphenyl; carboxyphenyl; —$(CH_2)_n$—C(=O)—OH; —$(CH_2)_n$—C(=O)—O—$C_{1-6}$alkyl, —$(CH_2)_n$—C(=O)—N(—H, —$C_{1-6}$alkyl; —$(CH_2)_n$—C(=O)—N(—$C_{1-6}$alkyl, —$C_{1-6}$alkyl), —$(CH_2)_n$—C(=O)—[N]-morpholinyl; —$(CH_2)_n$—C(=O)—[N]-piperidyl; —$(CH_2)_n$—C(=O)—[N]-piperazinyl; —$(CH_2)_n$—S(=O)$_2$—$C_{1-6}$alkyl; —$(CH_2)_n$—S(=O)$_2$-phenyl; —$(CH_2)_n$—P(=O, (—O—$C_{1-6}$alkyl)$_2$); —CN, benzyl, pryidylmethyl and imidazolylmethyl;

n is 0–2

E is a member selected from the group consisting of:
a direct link, —C(=O)—, —C(=O)—N($R^5$)—, —N($R^5$)—C(=O)—, —S(=O)$_2$—N($R^5$)—, —$CH_2$—O—, —$CH_2$—S—, —$CH_2$—S(=O)—, —$CH_2$—S(=O)$_2$—, —$CH_2$—N(—$R^5$)—, —C(—$R^{5a}$,—$R^{6a}$)— and —(—C(—$R^{5b}$,—$R^{6b}$)—C(—$R^{5c}$,—$R^{6c}$)—;

wherein $R^5$, $R^6$, $R^{5a}$, $R^{6a}$, $R^{5b}$ $R^{6b}$, $R^{5c}$ and $R^{6c}$ are independently selected from:

H, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$alkyl, —CN and —$NO_2$;

K is a member selected from the group consisting of:
(a) phenyl, which is independently substituted with 0–2 $R^b$ substituents;
(b) naphthyl, which is independently substituted with 0–2 $R^b$ substituents; and
(c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^b$ substituents;

$R^b$ is a member selected from the group consisting of:
halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $NR^{1b}R^{2b}$, $SO_2NR^{1b}R^{2b}$, $SO_2R^{1b}$, $CF_3$, $OR^{1b}$, O—$CH_2$—$CH_2$—$OR^{1b}$, O—$CH_2$—$COOR^{1b}$, $N(R^{1b})$—$CH_2$—$CH_2$—$OR^{1b}$, $N(-CH_2-CH_2-OR^{1b})_2$, $N(R^{1b})$—$C(=O)R^{2b}$, $N(R^{1b})$—$SO_2$—$R^{2b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{1b}$ and $R^{2b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

L is selected from:
H, —CN, $C(=O)NR^{12}R^{13}$, $(CH_2)_nNR^{12}R^{13}$, —$C(=NR^{12})NR^{12}R^{13}$, —CH=N—N(—$R^{12}$)—C(=$NR^{12a}$), —N(—$R^{12b}$,—$R^{12c}$), —$OR^{12}$, —$NR^{12}$C(=$NR^{12}$)$NR^{12}R^{13}$, and $NR^{12}C(=NR^{12})$—$R^{13}$;

$R^{12}$, $R^{12a}$, $R^{12b}$, $R^{12c}$ and $R^{13}$ are independently selected from:
hydrogen, —$OR^{14}$, —$NR^{14}R^{15}$, $C_{1-4}$alkyl, $C_{0-4}$alkylphenyl, $C_{0-4}$alkylnaphthyl, COO$C_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

$R^{14}$ and $R^{15}$ are independently selected from:
H, $C_{1-4}$alkyl, —C(=O)—O—$C_{0-6}$alkyl, —C(=O)—$NH_2$, —C(=O)—N(—H, —$C_{1-6}$alkyl) —C(=O)—N(—$C_{1-6}$alkyl, —$C_{1-6}$alkyl), —C(=O)—N(—H, —$C_{1-6}$alkyl-N(—$C_{1-6}$alkyl, —$C_{1-6}$alkyl)), —C(=O)—N(—$C_{1-6}$alkyl, —$C_{1-6}$alkyl-N(—$C_{1-6}$alkyl, —$C_{1-6}$alkyl)), —C(=O)—([N,N]-piperazino-$C_{1-6}$alkyl), —$C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, and —COO—$C_{0-4}$alkyl;

and all pharmaceutically acceptable isomers, salts, hydrates, solvates and prodrug derivatives thereof.

In a further preferred embodiment, the present invention provides a compound according to the formula I:

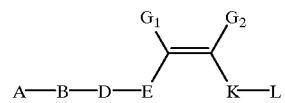

wherein:
A is selected from:
(a) phenyl, which is independently substituted with 0–2 R substituents; and
(b) an aromatic or non-aromatic monocyclic heterocyclic ring having from 5 to 6 ring atoms, wherein 1–4 ring atoms of the ring system are selected from N, O and S, and wherein the ring system may be substituted with 0–2 R substituents;

R is selected from:
—$(CH_2)_mNR^1R^2$, —$SO_2NR^1R^2$, —C(=O)—$NR^1R^2$, —$SO_2R^1$, —$CF_3$, —$SR^1$, —$OR^1$, and a 5–6 membered aromatic heterocyclic system containing from 1–4 heteroatoms selected from N, O and S;

$R^1$ and $R^2$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —C(=O)—OH, —C(=O)—O—$C_{1-6}$alkyl, —C(=O)—$NH_2$, —C(=O)—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —C$_1$–C$_4$-alkyl, —CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —NH$_2$; —N(—C$_{1-4}$alkyl, —C$_{0-4}$alkyl), and —NO$_2$;
m is an integer of 0–2;
B is a member selected from the group consisting of:
a direct link,
D is a member selected from the group consisting of:
(a) phenyl, which is independently substituted with 0–2 R$^a$ substituents; and
(b) pyridyl, which may be substituted with 0–2 R$^a$ substituents;
R$^a$ is selected from:
halo, —CF$_3$, —CBF$_2$, —CH$_2$—F, —SR$^{1a}$ and —OR$^{1a}$;
R$^{1a}$, in each occurrence, is independently selected from the group consisting of:
H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;
G$^1$ and G$^2$ are each independently selected from hydrogen or R$^4$;
R$^4$ is independently a member selected from the group consisting of:
F; Br; Cl; —CN; —NO$_2$; —C$_{1-6}$alkyl; —O—C$_{1-6}$alkyl; —C$_{1-4}$alkyl substituted by up to 4 of the same or different halogen atoms independently selected from the group consisting of F, Br, and Cl; —C$_{3-8}$cycloalkyl substituted by up to 6 of the same or different halogen atoms independently selected from the group consisting of F, Br, and Cl; phenyl; pyridyl; pyrimidyl; imidazolyl; pyrrolyl; furanyl; thiophenyl; tetrazolyl; pyrazolyl; oxazolyl; isoxazolyl; —O—C$_{1-4}$alkyl; —N(—H)—C(=O)—C$_{1-6}$alkyl; —N(—H)—C(=O)-phenyl; methoxycarbonylphenyl; carboxyphenyl; —(CH$_2$)$_n$—C(=O)—OH; —(CH$_2$)$_n$—C(=O)—O—C$_{1-6}$alkyl, —(CH$_2$)$_n$—C(=O)—N(—H, —C$_{1-6}$alkyl; —CH$_2$)$_n$—C(=O)—N(—C$_{1-6}$alkyl, —C$_{1-6}$alkyl), —(CH$_2$)$_n$—C(=O)—[N]-morpholinyl; —(CH$_2$)$_n$—C(=O)—[N]-piperidyl; —(CH$_2$)$_n$—C(=O)—[N]-piperazinyl; —(CH$_2$)$_n$—S(=O)$_2$—C$_{1-6}$alkyl; —(CH$_2$)$_n$—S(=O)$_2$-phenyl; —(CH$_2$)$_n$—P(=O, (—O—C$_{1-6}$alkyl)$_2$); —CN, benzyl, pryidylmethyl and imidazolylmethyl;
n is 0–2
E is a member selected from the group consisting of:
a direct link, —C(=O)—, —C(=O)—N(R$^5$)—, —N(R$^5$)—C(=O)—, —S(=O)$_2$—N(R$^5$)—, —CH$_2$—O—, —CH$_2$—S—, —CH$_2$—S(=O)—, —CH$_2$—S(=O)$_2$—, —CH$_2$—N(—R$^5$)—, —C(—R$^{5a}$,—R$^{6a}$)— and —(—C(—R$^{5b}$,—R$^{6b}$)—C(—R$^{5c}$,—R$^{6c}$)—;
wherein R$^5$, R$^6$, R$^{5a}$, R$^{6a}$, R$^{5b}$ R$^{6b}$, R$^{5c}$ and R$^{6c}$ are independently selected from:

H, —OH, —O—C$_{1-4}$alkyl, —C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl, C$_{0-4}$alkylnaphthyl, C$_{0-4}$alkylheteroaryl, C$_{1-4}$alkylCOOH and C$_{1-4}$alkylCOOC$_{1-4}$alkyl, wherein from 0–4 hydrogen atoms on the ring atoms of the phenyl, naphthyl and heteroaryl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —OH, —O—C$_{1-4}$alkyl, —SH, —S—C$_{1-4}$alkyl, —CN and —NO$_2$;

K and L taken together are a member selected from the group consisting of:

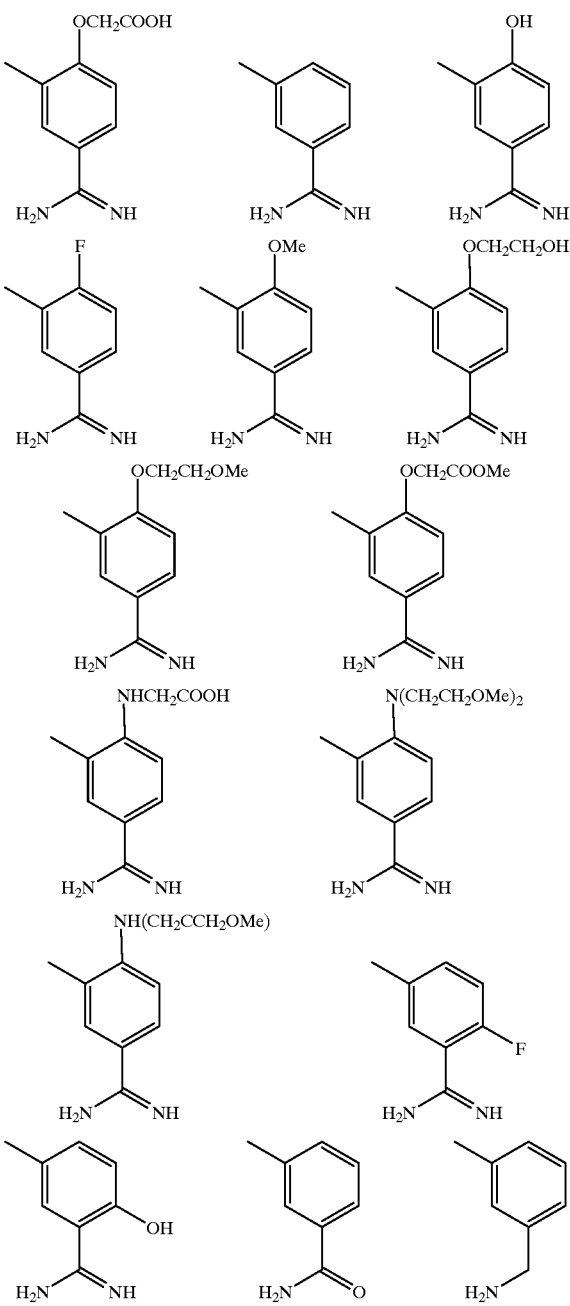

-continued

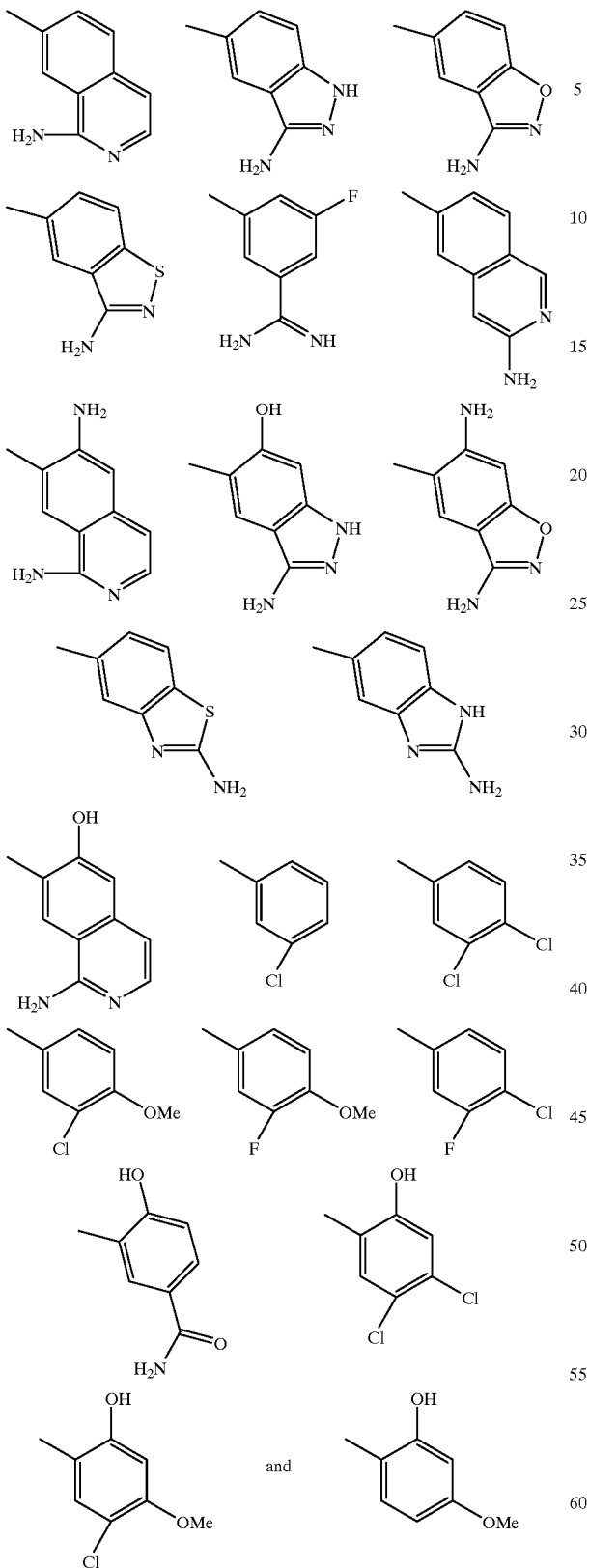

and all pharmaceutically acceptable isomers, salts, hydrates, solvates and prodrug derivatives thereof.

In a further preferred embodiment, the present invention provides a compound according to the formula I:

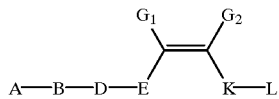

wherein:

A is selected from:
(a) phenyl, which is independently substituted with 0–2 R substituents; and
(b) an aromatic or non-aromatic monocyclic heterocyclic ring having from 5 to 6 ring atoms, wherein 1–4 ring atoms of the ring system are selected from N, O and S, and wherein the ring system may be substituted with 0–2 R substituents;

R is selected from:
—$(CH_2)_m NR^1R^2$, —$SO_2NR^1R^2$, —C(=O)—$NR^1R^2$, —$SO_2R^1$, —$CF_3$, —$SR^1$, —$OR^1$, and a 5–6 membered aromatic heterocyclic system containing from 1–4 heteroatoms selected from N, O and S;

$R^1$ and $R^2$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —C(=O)—OH, —C(=O)—O—$C_{1-6}$alkyl, —C(=O)—$NH_2$, —C(=O)—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$-$C_4$-alkyl, —CN, —$C_{1-4}$alkyl, —$C_{2-6}$alkenyl, —$C_{2-6}$ alkynyl, —$C_{3-8}$cycloalkyl, —$C_{0-4}$alkyl$C_{3-8}$ cycloalkyl, —$NH_2$; —N(—$C_{1-4}$alkyl, —$C_{0-4}$ alkyl), and —$NO_2$;
m is an integer of 0–2;

B is a member selected from the group consisting of:
a direct link,

D is a member selected from the group consisting of:
(a) phenyl, which is independently substituted with 0–2 $R^a$ substituents; and
(b) pyridyl, which may be substituted with 0–2 $R^a$ substituents;
$R^a$ is selected from:
halo, —$CF_3$, —$CHF_2$, —$CH_2$—F, —$SR^{1a}$ and —$OR^{1a}$,
$R^{1a}$, in each occurrence, is independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$G^1$ and $G^2$ are each independently selected from hydrogen or $R^4$;

$R^4$ is independently a member selected from the group consisting of:

F; Br; Cl; —CN; —$NO_2$; —$C_{1-6}$alkyl; —O—$C_{1-6}$alkyl; —$C_{1-4}$alkyl substituted by up to 4 of the same or different halogen atoms independently selected from the group consisting of F, Br, and Cl; —$C_{3-8}$ cycloalkyl substituted by up to 6 of the same or different halogen atoms independently selected from the group consisting of F, Br, and Cl; phenyl; pyridyl; pyrimidyl; imidazolyl; pyrrolyl; furanyl; thiophenyl; tetrazolyl; pyrazolyl; oxazolyl; isoxazolyl; —O—$C_{1-4}$alkyl; —N(—H)—C(=O)—$C_{1-6}$ alkyl; —N(—H)—C(=O)-phenyl; methoxycarbonylphenyl; carboxyphenyl; —$(CH_2)_n$—C(=O)—OH; —$(CH_2)_n$—C(=O)—O—$C_{1-6}$alkyl, —$(CH_2)_n$—C(=O)—N(—H, —$C_{1-6}$alkyl; —$(CH_2)_n$—C(=O)—N(—$C_{1-6}$alkyl, —$C_{1-6}$alkyl), —$(CH_2)_n$—C(=O)—[N]-morpholinyl; —$(CH_2)_n$—C(=O)—[N]-piperidyl; —$(CH_2)_n$—C(=O)—[N]-piperazinyl; —$(CH_2)_n$—S(=O)$_2$—$C_{1-6}$alkyl; —$(CH_2)_n$—S(=O)$_2$-phenyl; —$(CH_2)_n$—P(=O, (—O—$C_{1-6}$alkyl)$_2$); —CN, benzyl, pryidylmethyl and imidazolylmethyl;

n is 0–2

E is a member selected from the group consisting of: a direct link, —C(=O)—, —C(=O)—N($R^5$)—, —S(=O)$_2$—N($R^5$)—, —N($R^5$)—C(=O)—, —$CH_2$—O—, —$CH_2$—S—, —$CH_2$—S(=O)—, —$CH_2$—S(=O)$_2$—, —$CH_2$—N(—$R^5$)—, —C(—$R^{5a}$,—$R^{6a}$)— and —(—C(—$R^{5b}$,—$R^{6b}$)—C(—$R^{5c}$,—$R^{6c}$)—;

wherein $R^5$, $R^6$, $R^{5a}$, $R^{6a}$, $R^{5b}$ $R^{6b}$, $R^{5c}$ and $R^{6c}$ are independently selected from:

H, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl, —OH, —O—$C_{1-4}$alkyl, —SH, —S—$C_{1-4}$alkyl, —CN and —$NO_2$;

K and L taken together are a member selected from the group consisting of:

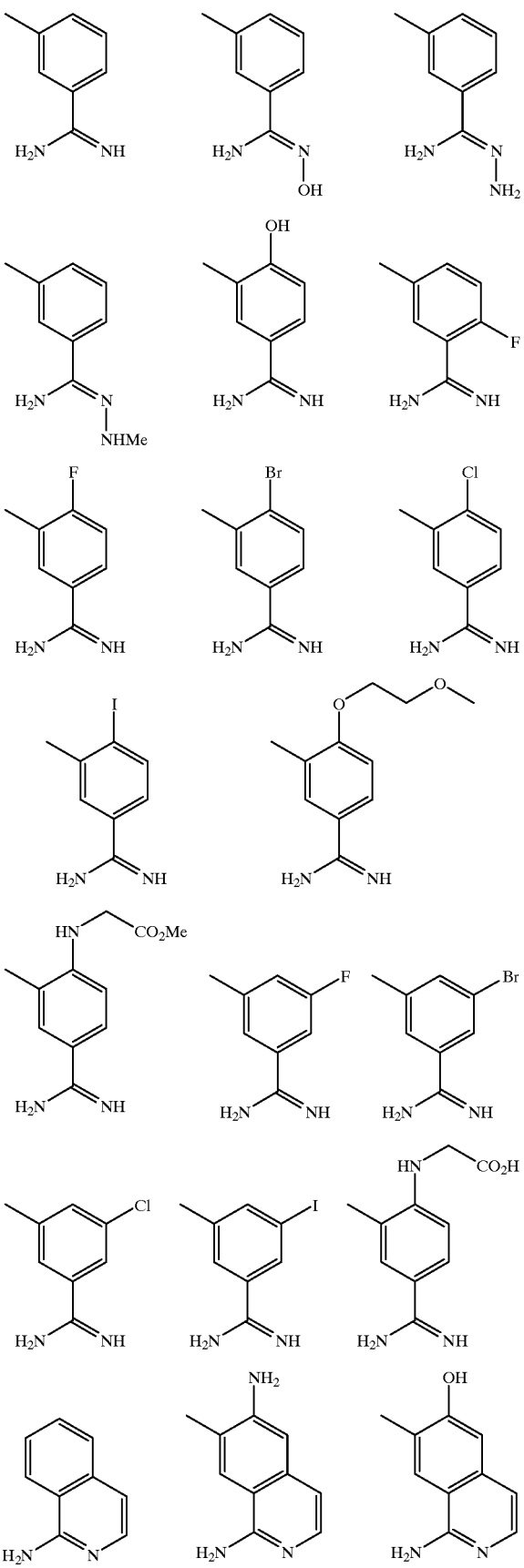

and all pharmaceutically acceptable isomers, salts, hydrates, solvates and prodrug derivatives thereof.

In yet another preferred embodiment, the present invention provides a compound according to formula I:

$$A-B-D-E\underset{K-L}{\overset{G_1\quad G_2}{\diagup\!\!\!\diagdown}}$$

wherein

A is a member selected from the group consisting of:

B is a direct link;

D is a member selected from the group consisting of:

E is the group:

wherein $R^5$ member selected from the group consisting of:
H, $CH_2CO_2H$, $CH_2CO_2CH_3$, benzyl, carboxybenzyl, phenyl and carboxyphenyl;

K and L taken together are a member selected from the group consisting of:

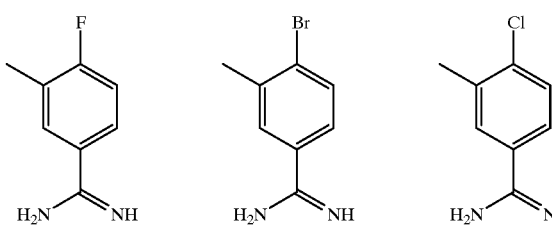
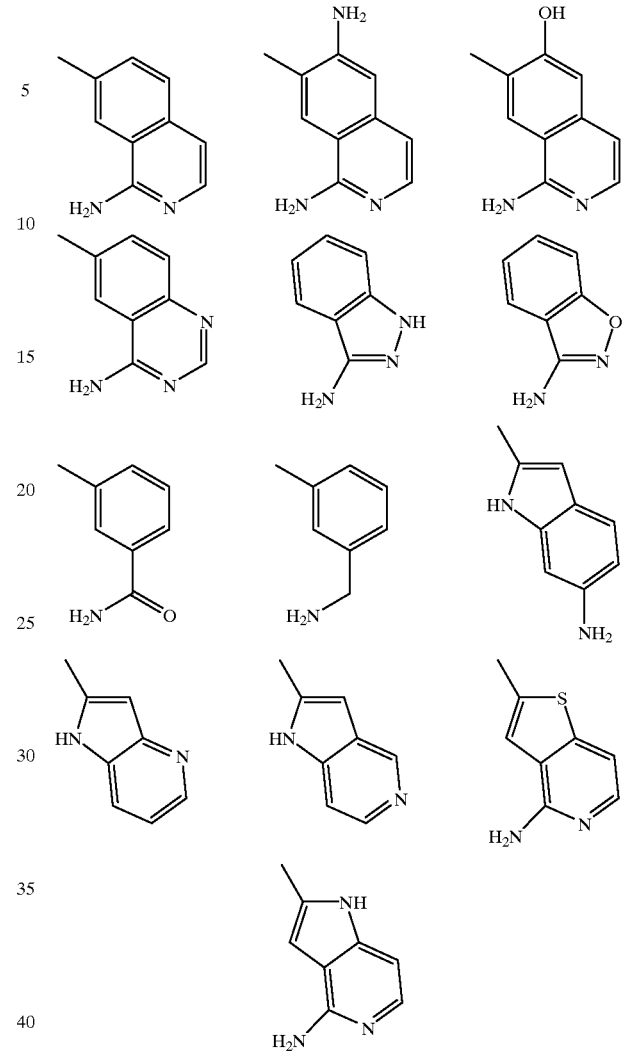
and all pharmaceutically acceptable isomers, salts, hydrates, solvates and prodrug derivatives thereof.
TABLE 1
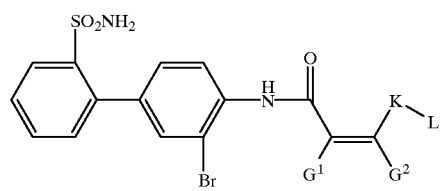
Formula II
| $G^1$ | $G^2$ | $G^1$ | $G^2$ |
|---|---|---|---|
| H | H | OMe | H |
| Me | Me | OMe | Me |
| | | F | H |

TABLE 1-continued
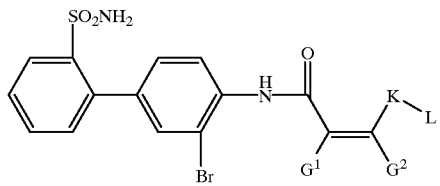
Formula II
| G¹ | G² | G¹ | G² |
|---|---|---|---|
| 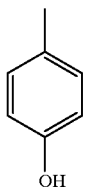 | 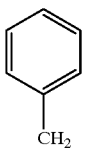 | —OMe | Me |
| 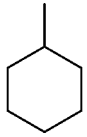 | 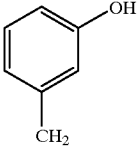 | F | Me |
| 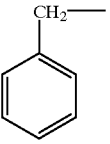 | 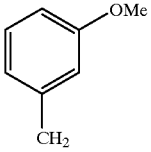 | —CF3 | H |
| 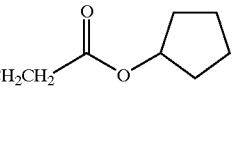 | 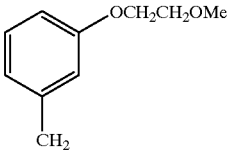 | OCH2Ph | H |
| 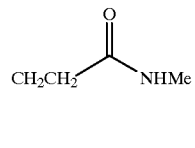 | 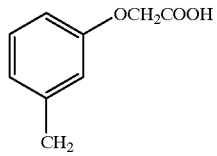 | OCH2CH2OMe | H |
| 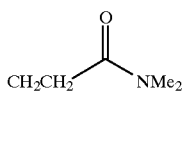 | 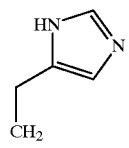 | H | Et |
| 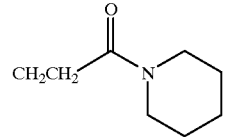 | 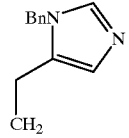 | Me | Et |

TABLE 1a

Formula IIa

[Structure: 2'-sulfamoyl-3-bromo-biphenyl-4-yl acrylamide with G¹, G² on alkene and K-L substituent]

| G¹ | G² | G¹ | G² |
|---|---|---|---|
| H | H | OMe | H |
| Me | Me | OMe | Me |
| 4-methylphenyl | phenyl | F | H |
| 4-hydroxy-4-methylphenyl | benzyl (PhCH₂) | —OMe | Me |
| 4-methylcyclohexyl | 3-hydroxybenzyl | F | Me |
| PhCH₂CH₂— | 3-methoxybenzyl | —CF3 | H |
| cyclopentyl-O-C(=O)-CH₂CH₂— | 3-(OCH2CH2OMe)benzyl | OCH2Ph | H |
| MeHN-C(=O)-CH₂CH₂— | 3-(OCH2COOH)benzyl | OCH2CH2OMe | H |
| Me₂N-C(=O)-CH₂CH₂— | (1H-imidazol-5-yl)methyl | H | Et |

TABLE 1a-continued
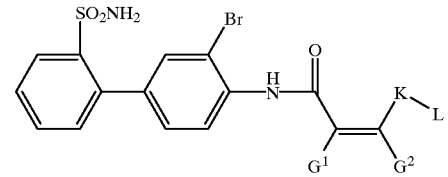
Formula IIa
| G¹ | G² | G¹ | G² |
|---|---|---|---|
| 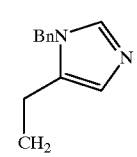 | 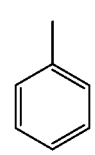 | Me | Et |
TABLE 1b
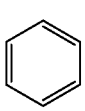
| G¹ | G² | G¹ | G² |
|---|---|---|---|
| H | H | OMe | H |
| Me | Me | OMe | Me |
| 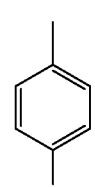 | 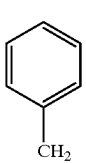 | F | H |
| 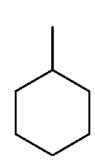 | 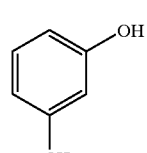 | —OMe | Me |
| 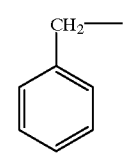 | 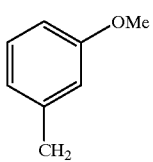 | F | Me |
|  |  | —CF3 | H |

TABLE 1b-continued
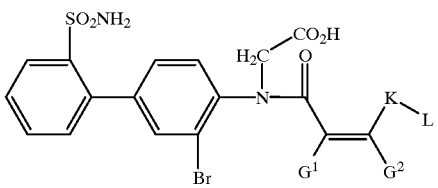
| G¹ | G² | G¹ | G² |
|---|---|---|---|
| 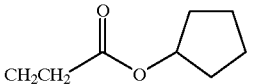 | 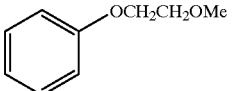 | OCH2Ph | H |
| 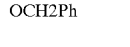 | 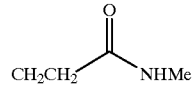 | OCH2CH2OMe | H |
| 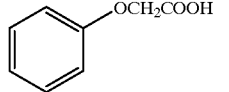 |  | H | Et |
| 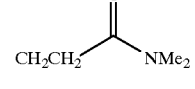 | 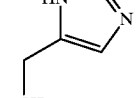 | Me | Et |
TABLE 2
Formula III
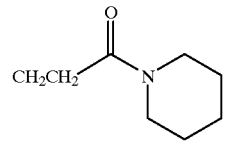
| G¹ | G² | G¹ | G² |
|---|---|---|---|
| H | H | OMe | H |
| Me | Me | OMe | Me |
| 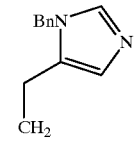 | 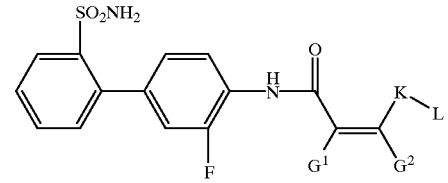 | F | H |

TABLE 2-continued
Formula III
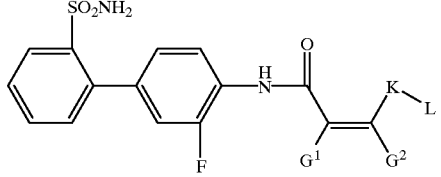
| G¹ | G² | G¹ | G² |
|---|---|---|---|
| 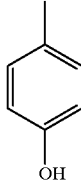 | 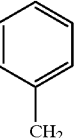 | —OMe | Me |
| 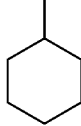 | 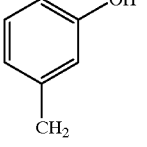 | F | Me |
| 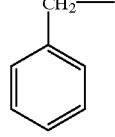 | 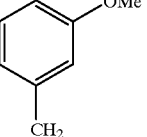 | —CF3 | H |
| 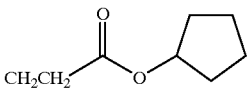 | 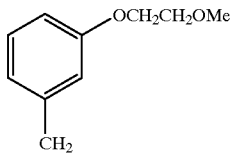 | OCH2Ph | H |
| 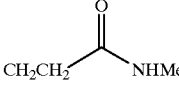 | 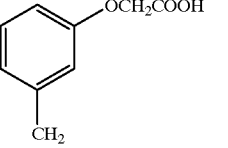 | OCH2CH2OMe | H |
| 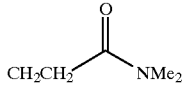 | 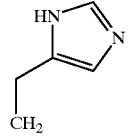 | H | Et |
| 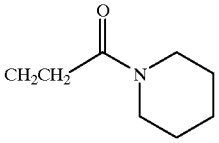 |  | Me | Et |

TABLE 2a

Formula IIIa

[Structure: 2-sulfamoyl-2'-fluoro-4'-(acylamino)biphenyl with acrylamide bearing G¹ and G² substituents, and K-L group]

| G¹ | G² | G¹ | G² |
|---|---|---|---|
| H | H | OMe | H |
| Me | Me | OMe | Me |
| 4-methylphenyl | phenyl | F | H |
| 4-hydroxy-methylphenyl | benzyl (PhCH₂) | —OMe | Me |
| 4-methylcyclohexyl | 3-hydroxybenzyl | F | Me |
| benzyl (PhCH₂—) | 3-methoxybenzyl | —CF3 | H |
| CH₂CH₂C(O)O-cyclopentyl | 3-(OCH₂CH₂OMe)benzyl | OCH2Ph | H |
| CH₂CH₂C(O)NHMe | 3-(OCH₂COOH)benzyl | OCH2CH2OMe | H |
| CH₂CH₂C(O)NMe₂ | (1H-imidazol-5-yl)methyl | H | Et |

TABLE 2a-continued

Formula IIIa

[Structure: 2-sulfamoyl-biphenyl with 3-fluoro and 4-NH-C(=O)-C(G¹)=C(G²)-K-L substituents]

| G¹ | G² | G¹ | G² |
|---|---|---|---|
| CH₂CH₂-C(=O)-N(piperidine) | CH₂-(1-Bn-imidazol-5-yl) | Me | Et |

TABLE 2b

Formula IIIb

[Structure: 2-sulfamoyl-biphenyl with 3-fluoro and 4-N(CH₂CO₂H)-C(=O)-C(G¹)=C(G²)-K-L substituents]

| G¹ | G² | G¹ | G² |
|---|---|---|---|
| H | H | OMe | H |
| Me | Me | OMe | Me |
| 4-methylphenyl | phenyl | F | H |
| 4-hydroxy-3-methylphenyl | benzyl (CH₂-phenyl) | —OMe | Me |
| cyclohexyl-CH— | 3-hydroxybenzyl (CH₂-C₆H₄-OH) | F | Me |
| benzyl (CH₂-phenyl) | 3-methoxybenzyl (CH₂-C₆H₄-OMe) | —CF₃ | H |

TABLE 2b-continued
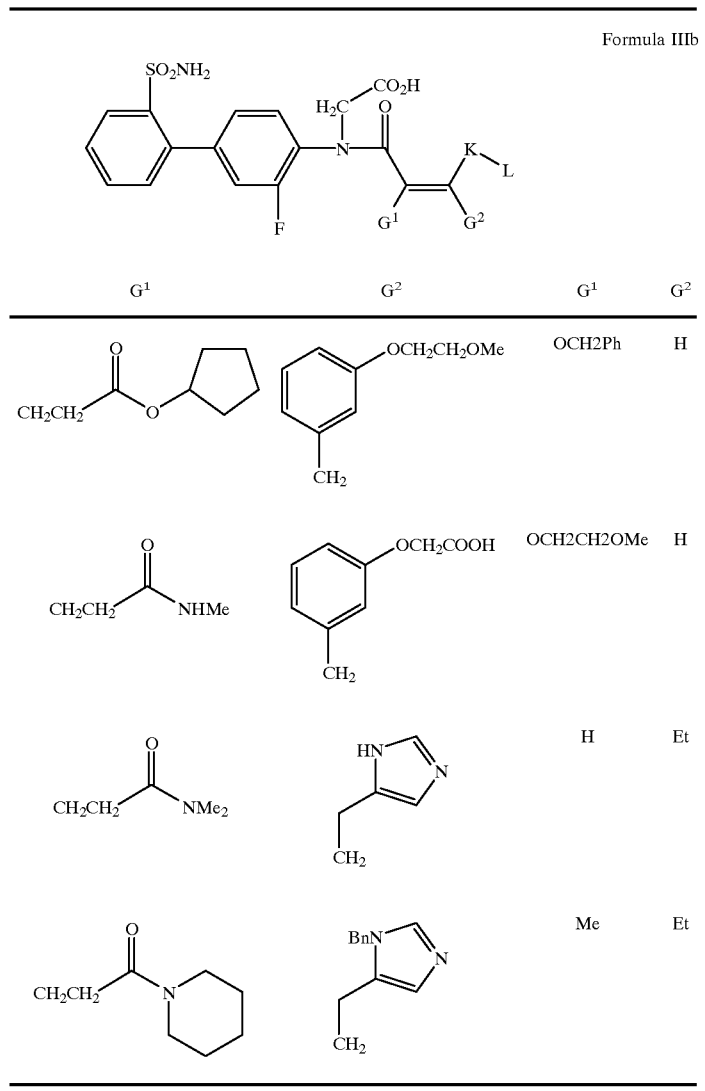
Formula IIIb
TABLE 3
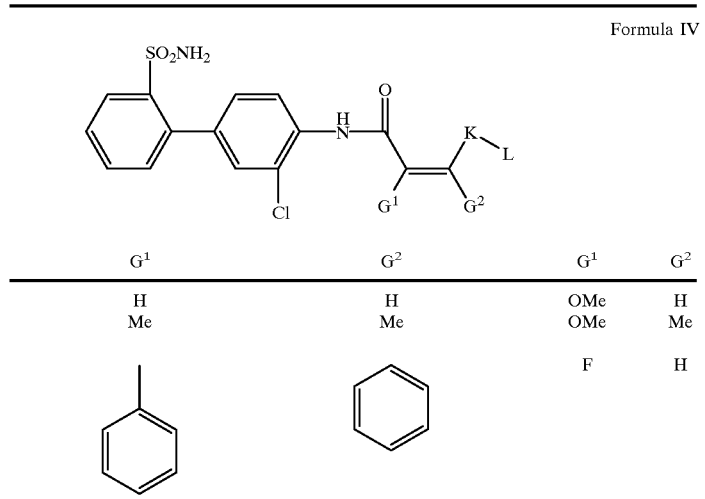
Formula IV
| $G^1$ | $G^2$ | $G^1$ | $G^2$ |
|---|---|---|---|
| H | H | OMe | H |
| Me | Me | OMe | Me |
| Ph | Ph | F | H |

TABLE 3-continued
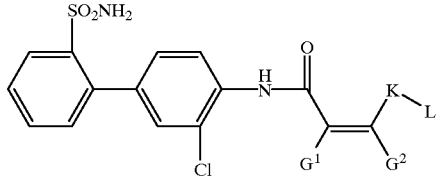
Formula IV
| G¹ | G² | G¹ | G² |
|---|---|---|---|
| 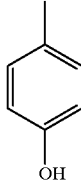 | 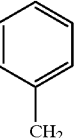 | —OMe | Me |
| 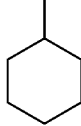 | 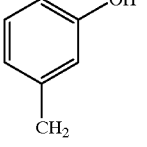 | F | Me |
| 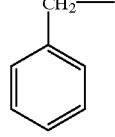 | 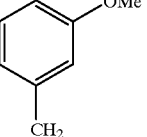 | —CF3 | H |
| 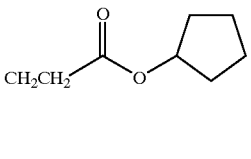 | 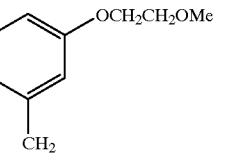 | OCH2Ph | H |
| 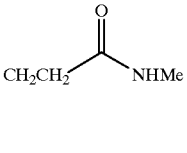 | 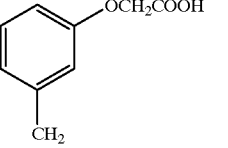 | OCH2CH2OMe | H |
| 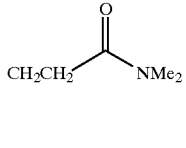 | 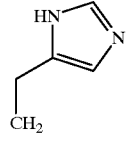 | H | Et |
| 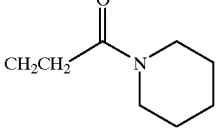 | 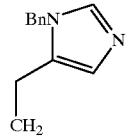 | Me | Et |

TABLE 3a

Formula IVa

[Structure: 2-sulfamoyl-biphenyl with 3-chloro-4-(NH-CO-C(G¹)=C(G²)-K-L) substituent]

| G¹ | G² | G¹ | G² |
|---|---|---|---|
| H | H | OMe | H |
| Me | Me | OMe | Me |
| 4-methylphenyl | phenyl | F | H |
| 4-hydroxy-4-methylphenyl | benzyl (CH₂-phenyl) | —OMe | Me |
| 4-methylcyclohexyl | 3-hydroxybenzyl (CH₂-C₆H₄-OH) | F | Me |
| benzyl (CH₂-phenyl) | 3-methoxybenzyl (CH₂-C₆H₄-OMe) | —CF3 | H |
| CH₂CH₂-C(O)-O-cyclopentyl | 3-(OCH₂CH₂OMe)benzyl | OCH2Ph | H |
| CH₂CH₂-C(O)-NHMe | 3-(OCH₂COOH)benzyl | OCH2CH2OMe | H |
| CH₂CH₂-C(O)-NMe₂ | (1H-imidazol-5-yl)methyl | H | Et |

TABLE 3a-continued
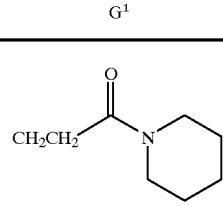
Formula IVa
| G¹ | G² | G¹ | G² |
|---|---|---|---|
| 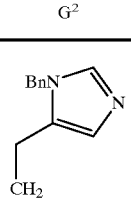 | 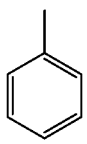 | Me | Et |
TABLE 3b
Formula IVb
| G¹ | G² | G¹ | G² |
|---|---|---|---|
| H | H | OMe | H |
| Me | Me | OMe | Me |
| 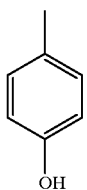 | 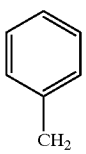 | F | H |
| 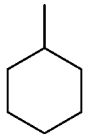 | 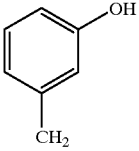 | —OMe | Me |
| 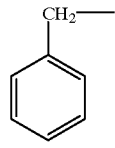 | 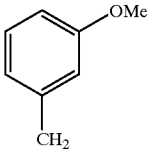 | F | Me |
| | | —CF3 | H |

TABLE 3b-continued
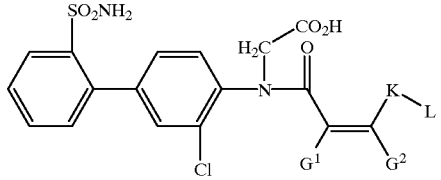
Formula IVb
| G¹ | G² | G¹ | G² |
|---|---|---|---|
| 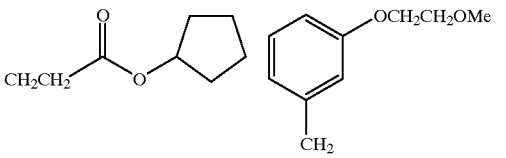 | 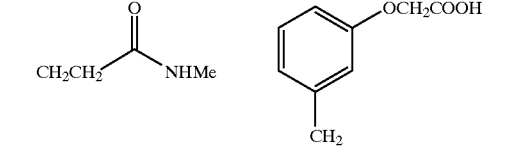 | OCH2Ph | H |
| 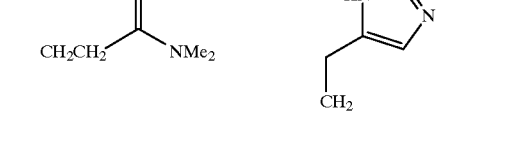 | 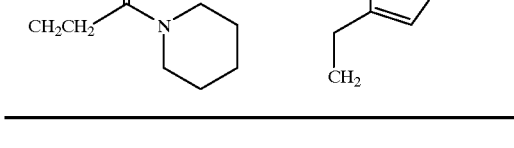 | OCH2CH2OMe | H |
| 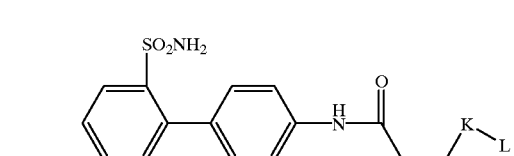 | 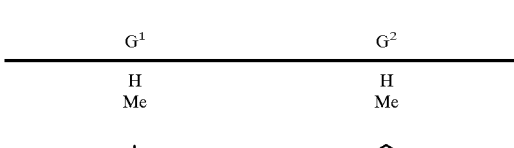 | H | Et |
|  | 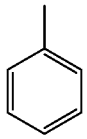 | Me | Et |
TABLE 4
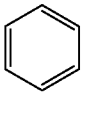
Formula V
| G¹ | G² | G¹ | G² |
|---|---|---|---|
| H | H | OMe | H |
| Me | Me | OMe | Me |
| Ph | Ph | F | H |

TABLE 4-continued

Formula V

[Structure: 2-sulfamoyl-biphenyl with iodo substituent, linked via NH-C(=O)-C(G¹)=C(G²)-K-L acrylamide]

| G¹ | G² | G¹ | G² |
|---|---|---|---|
| 4-hydroxy-4-methylphenyl | 3-(CH₂)-phenyl (benzyl) | —OMe | Me |
| cyclohexyl-methyl | 3-hydroxybenzyl | F | Me |
| benzyl-CH₂ | 3-methoxybenzyl | —CF3 | H |
| CH₂CH₂-C(=O)-O-cyclopentyl | 3-(OCH₂CH₂OMe)-benzyl | OCH2Ph | H |
| CH₂CH₂-C(=O)-NHMe | 3-(OCH₂COOH)-benzyl | OCH2CH2OMe | H |
| CH₂CH₂-C(=O)-NMe₂ | (1H-imidazol-5-yl)methyl | H | Et |
| CH₂CH₂-C(=O)-piperidinyl | (1-Bn-imidazol-5-yl)methyl | Me | Et |

TABLE 4a

Formula Va

[Structure: 2'-sulfamoyl-3-iodo-biphenyl with NH-C(=O)-C(G¹)=C(G²)-K-L substituent]

| G¹ | G² | G¹ | G² |
|---|---|---|---|
| H | H | OMe | H |
| Me | Me | OMe | Me |
| 4-methylphenyl | phenyl | F | H |
| 4-hydroxy-4-methylphenyl | benzyl (CH₂-phenyl) | —OMe | Me |
| cyclohexylmethyl | 3-hydroxybenzyl | F | Me |
| CH₂—phenyl (benzyl) | 3-methoxybenzyl | —CF₃ | H |
| CH₂CH₂C(=O)O-cyclopentyl | 3-(OCH₂CH₂OMe)benzyl | OCH2Ph | H |
| CH₂CH₂C(=O)NHMe | 3-(OCH₂COOH)benzyl | OCH2CH2OMe | H |
| CH₂CH₂C(=O)NMe₂ | (1H-imidazol-5-yl)methyl | H | Et |

TABLE 4a-continued

Formula Va

| G¹ | G² | G¹ | G² |
|---|---|---|---|
| | | Me | Et |
| CH₂CH₂-C(=O)-N(piperidine) | CH₂-(1-Bn-imidazol-5-yl) | | |

TABLE 4b

Formula Vb

| G¹ | G² | G¹ | G² |
|---|---|---|---|
| H | H | OMe | H |
| Me | Me | OMe | Me |
| 4-methylphenyl | phenyl | F | H |
| 4-hydroxyphenyl (CH₂) | benzyl (CH₂) | —OMe | Me |
| cyclohexyl | 3-hydroxybenzyl (CH₂) | F | Me |
| benzyl (CH₂) | 3-methoxybenzyl (CH₂) | —CF₃ | H |

TABLE 4b-continued
Formula Vb
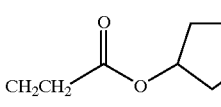
| G¹ | G² | G¹ | G² |
|---|---|---|---|
| 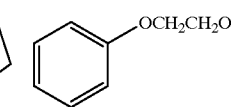 |  | OCH2Ph | H |
| 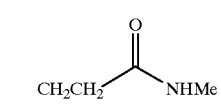 | 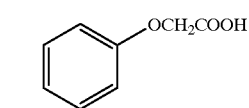 | OCH2CH2OMe | H |
|  | 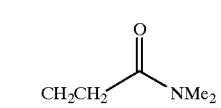 | H | Et |
| 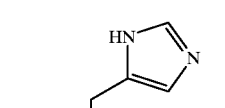 | 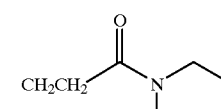 | Me | Et |
TABLE 5
Formula VI
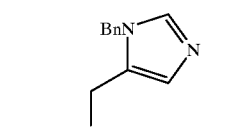
| G¹ | G² | G¹ | G² |
|---|---|---|---|
| H | H | OMe | H |
| Me | Me | OMe | Me |
| | | F | H |

TABLE 5-continued
Formula VI
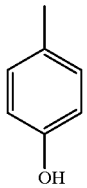
| G¹ | G² | G¹ | G² |
|---|---|---|---|
| | | —OMe | Me |
| 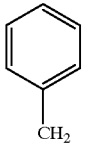 | 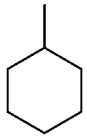 | | |
| 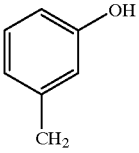 | 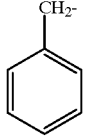 | F | Me |
| 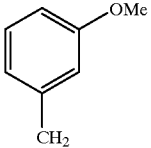 | 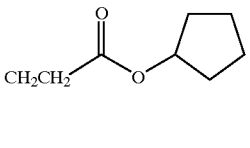 | —CF3 | H |
| 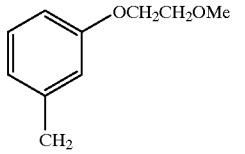 | 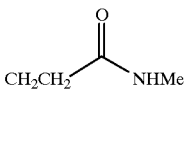 | OCH2Ph | H |
| 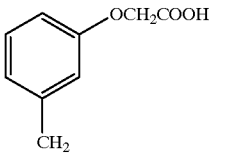 | 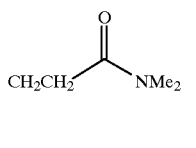 | OCH2CH2OMe | H |
| 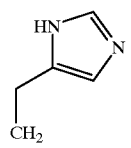 | 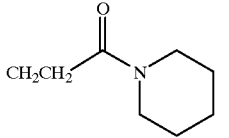 | H | Et |
| 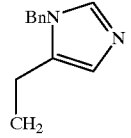 | | Me | Et |

TABLE 5a

Formula VIa

[Structure: 2'-sulfamoyl-3-trifluoromethyl biphenyl connected via NH-C(=O)-C(G¹)=C(G²)-K-L amide]

| G¹ | G² | G¹ | G² |
|---|---|---|---|
| H | H | OMe | H |
| Me | Me | OMe | Me |
| 4-methylphenyl | phenyl | F | H |
| 4-hydroxyphenyl | benzyl (PhCH₂) | —OMe | Me |
| cyclohexyl | 3-hydroxybenzyl | F | Me |
| benzyl (PhCH₂-) | 3-methoxybenzyl | —CF3 | H |
| CH₂CH₂C(=O)O-cyclopentyl | 3-(OCH₂CH₂OMe)benzyl | OCH2Ph | H |
| CH₂CH₂C(=O)NHMe | 3-(OCH₂COOH)benzyl | OCH2CH2OMe | H |
| CH₂CH₂C(=O)NMe₂ | (1H-imidazol-5-yl)methyl | H | Et |

TABLE 5a-continued
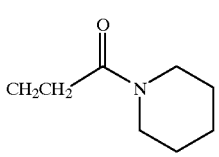
Formula VIa
| G¹ | G² | G¹ | G² |
|---|---|---|---|
|  | 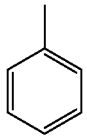 | Me | Et |
TABLE 5b
Formula VIb
| G¹ | G² | G¹ | G² |
|---|---|---|---|
| H | H | OMe | H |
| Me | Me | OMe | Me |
| 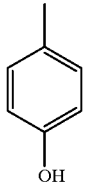 | 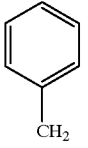 | F | H |
| 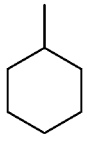 | 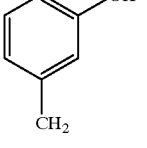 | —OMe | Me |
| 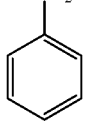 | 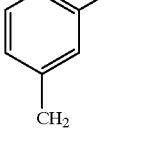 | F | Me |
| | | —CF3 | H |

TABLE 5b-continued

Formula VIb

[Structure: biphenyl with SO₂NH₂ on one ring and CF₃, N(CH₂CO₂H)-C(=O)-C(G¹)=C(G²)-K-L substituent on the other]

| G¹ | G² | G¹ | G² |
|---|---|---|---|
| CH₂CH₂-C(=O)-O-cyclopentyl | 3-(OCH₂CH₂OMe)-benzyl (CH₂-C₆H₄-OCH₂CH₂OMe) | OCH2Ph | H |
| CH₂CH₂-C(=O)-NHMe | 3-(OCH₂COOH)-benzyl | OCH2CH2OMe | H |
| CH₂CH₂-C(=O)-NMe₂ | (1H-imidazol-5-yl)methyl | H | Et |
| CH₂CH₂-C(=O)-N(piperidinyl) | (1-Bn-imidazol-5-yl)methyl | Me | Et |

TABLE 6

Formula VII

[Structure: biphenyl with SO₂NH₂ on one ring and OH, NH-C(=O)-C(G¹)=C(G²)-K-L on the other]

| G¹ | G² | G¹ | G² |
|---|---|---|---|
| H | H | OMe | H |
| Me | Me | OMe | Me |
| tolyl (4-methylphenyl) | phenyl | F | H |

TABLE 6-continued

Formula VII

[Structure: 2'-sulfamoyl-biphenyl with 3-hydroxy-4-(acrylamide) substituent, where the acrylamide has G¹, G² on the alkene carbon and K-L substituent]

| G¹ | G² | G¹ | G² |
|---|---|---|---|
| 4-hydroxyphenyl (p-HOC₆H₄–) | benzyl (PhCH₂–) | —OMe | Me |
| cyclohexyl | 3-hydroxybenzyl (3-HO-C₆H₄-CH₂–) | F | Me |
| benzyl (PhCH₂–) | 3-methoxybenzyl (3-MeO-C₆H₄-CH₂–) | —CF3 | H |
| cyclopentyl propanoate (–CH₂CH₂C(O)O-cyclopentyl) | 3-(2-methoxyethoxy)benzyl | OCH2Ph | H |
| –CH₂CH₂C(O)NHMe | 3-(carboxymethoxy)benzyl (3-HOOCCH₂O-C₆H₄-CH₂–) | OCH2CH2OMe | H |
| –CH₂CH₂C(O)NMe₂ | (1H-imidazol-5-yl)methyl | H | Et |
| –CH₂CH₂C(O)-piperidin-1-yl | (1-benzyl-1H-imidazol-5-yl)methyl | Me | Et |

TABLE 6a

Formula VIIa

[Structure: 2'-sulfamoyl-3-hydroxy-biphenyl-4-yl acrylamide with G¹, G² substituents on the alkene and K-L group]

| G¹ | G² | G¹ | G² |
|---|---|---|---|
| H | H | OMe | H |
| Me | Me | OMe | Me |
| 4-methylphenyl | phenyl | F | H |
| 4-hydroxy-methylphenyl | benzyl (PhCH₂) | —OMe | Me |
| cyclohexyl-methyl | 3-hydroxybenzyl | F | Me |
| benzyl (PhCH₂-) | 3-methoxybenzyl | —CF₃ | H |
| cyclopentyl propanoate (CH₂CH₂C(O)O-cyclopentyl) | 3-(OCH₂CH₂OMe)benzyl | OCH2Ph | H |
| CH₂CH₂C(O)NHMe | 3-(OCH₂COOH)benzyl | OCH2CH2OMe | H |
| CH₂CH₂C(O)NMe₂ | (1H-imidazol-5-yl)methyl | H | Et |

TABLE 6a-continued

Formula VIIa

| G¹ | G² | G¹ | G² |
|---|---|---|---|
| CH₂CH₂-C(O)-N(piperidine) | CH₂-(1-Bn-imidazol-5-yl) | Me | Et |

TABLE 6b

Formula VIIb

| G¹ | G² | G¹ | G² |
|---|---|---|---|
| H | H | OMe | H |
| Me | Me | OMe | Me |
| 4-methylphenyl | phenyl | F | H |
| 4-hydroxy-3-methylphenyl | benzyl (PhCH₂) | —OMe | Me |
| 4-methylcyclohexyl | 3-hydroxybenzyl | F | Me |
| benzyl (PhCH₂-) | 3-methoxybenzyl | —CF₃ | H |

TABLE 6b-continued

Formula VIIb

[Structure: biphenyl with SO₂NH₂ on one ring; other ring has OH and N(CH₂CO₂H)-C(=O)-C(G¹)=C(G²)-K-L substituent]

| G¹ | G² | G¹ | G² |
|---|---|---|---|
| [cyclopentyl propanoate ester: CH₂CH₂-C(=O)-O-cyclopentyl] | [3-(2-methoxyethoxy)benzyl: CH₂-C₆H₄-OCH₂CH₂OMe] | OCH2Ph | H |
| [N-methylpropanamide: CH₂CH₂-C(=O)-NHMe] | [3-(carboxymethoxy)benzyl: CH₂-C₆H₄-OCH₂COOH] | OCH2CH2OMe | H |
| [N,N-dimethylpropanamide: CH₂CH₂-C(=O)-NMe₂] | [(1H-imidazol-4-yl)methyl: CH₂-imidazole] | H | Et |
| [1-(piperidin-1-yl)propan-1-one: CH₂CH₂-C(=O)-N(piperidine)] | [(1-benzylimidazol-5-yl)methyl: CH₂-imidazole-Bn] | Me | Et |

TABLE 7

Formula VIII

[Structure: biphenyl with SO₂NH₂ on one ring; other ring has SH and NH-C(=O)-C(G¹)=C(G²)-K-L substituent]

| G¹ | G² | G¹ | G² |
|---|---|---|---|
| H | H | OMe | H |
| Me | Me | OMe | Me |
| [phenyl] | [phenyl] | F | H |

TABLE 7-continued
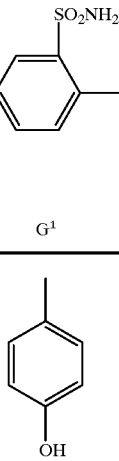
Formula VIII
| G¹ | G² | G¹ | G² |
|---|---|---|---|
| 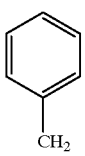 | 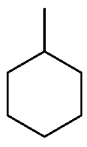 | —OMe | Me |
| 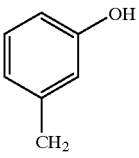 | 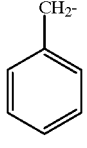 | F | Me |
| 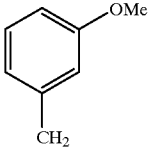 | 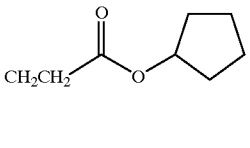 | —CF3 | H |
| 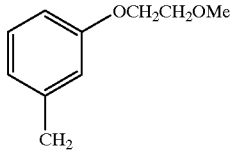 | 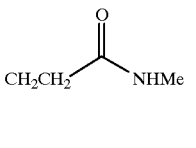 | OCH2Ph | H |
| 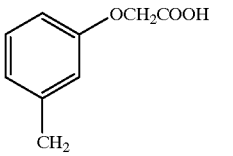 | 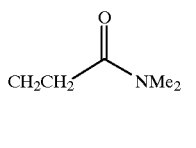 | OCH2CH2OMe | H |
| 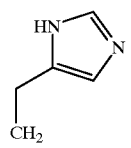 | 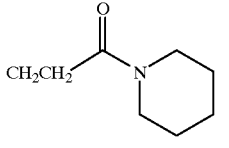 | H | Et |
| 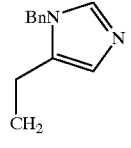 | | Me | Et |

TABLE 7a

Formula VIIIa

| G¹ | G² | G¹ | G² |
|---|---|---|---|
| H | H | OMe | H |
| Me | Me | OMe | Me |
| 4-methylphenyl | phenyl | F | H |
| 4-methylphenol | benzyl (CH₂-Ph) | —OMe | Me |
| cyclohexyl | 3-hydroxybenzyl | F | Me |
| benzyl (CH₂-Ph) | 3-methoxybenzyl | —CF₃ | H |
| CH₂CH₂C(O)O-cyclopentyl | 3-(OCH₂CH₂OMe)-benzyl | OCH2Ph | H |
| CH₂CH₂C(O)NHMe | 3-(OCH₂COOH)-benzyl | OCH2CH2OMe | H |
| CH₂CH₂C(O)NMe₂ | (1H-imidazol-5-yl)methyl | H | Et |

TABLE 7a-continued

Formula VIIIa

[Structure: biphenyl with SO₂NH₂, SH, and acrylamide substituents with G¹, G², K, L groups]

| G¹ | G² | G¹ | G² |
|---|---|---|---|
| CH₂CH₂-C(O)-N(piperidine) | BnN-imidazole-CH₂ | Me | Et |

TABLE 7b

Formula VIIIb

[Structure: biphenyl with SO₂NH₂, SH, CO₂H-CH₂, and N-acyl substituents with G¹, G², K, L groups]

| G¹ | G² | G¹ | G² |
|---|---|---|---|
| H | H | OMe | H |
| Me | Me | OMe | Me |
| 4-methylphenyl | phenyl | F | H |
| 4-hydroxy-3-methylphenyl | benzyl (PhCH₂) | —OMe | Me |
| 4-methylcyclohexyl | 3-hydroxybenzyl | F | Me |
| benzyl (PhCH₂-) | 3-methoxybenzyl | —CF₃ | H |

TABLE 7b-continued

Formula VIIIb

| G¹ | G² | G¹ | G² |
|---|---|---|---|
| (cyclopentyl propanoate ester: CH₂CH₂-C(=O)-O-cyclopentyl) | 3-(OCH₂CH₂OMe)-benzyl (CH₂-C₆H₄-OCH₂CH₂OMe) | OCH2Ph | H |
| CH₂CH₂-C(=O)-NHMe | 3-(OCH₂COOH)-benzyl | OCH2CH2OMe | H |
| CH₂CH₂-C(=O)-NMe₂ | (1H-imidazol-5-yl)methyl | H | Et |
| CH₂CH₂-C(=O)-piperidine | (1-benzyl-imidazol-5-yl)methyl | Me | Et |

Some preferred compounds are set forth in Tables 8–23, below.

TABLE 8

TABLE 8-continued

TABLE 8-continued
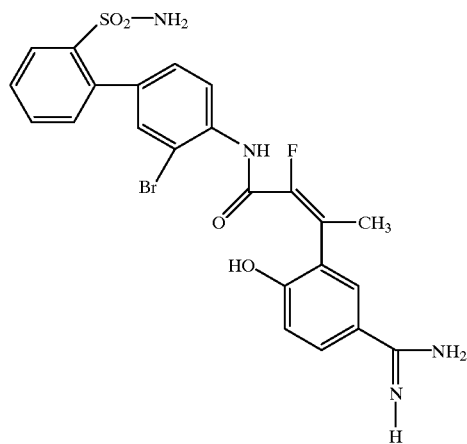
and
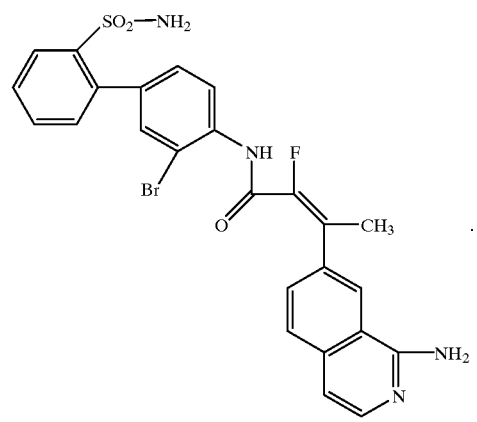
.
TABLE 9
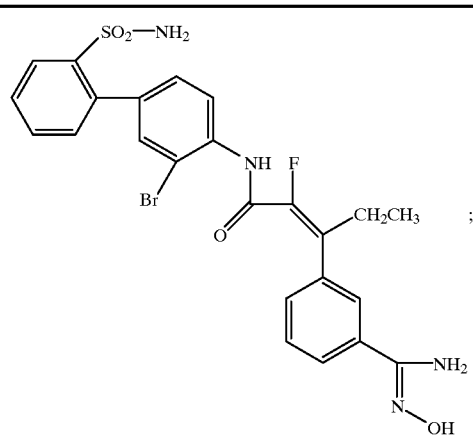
;
TABLE 9-continued
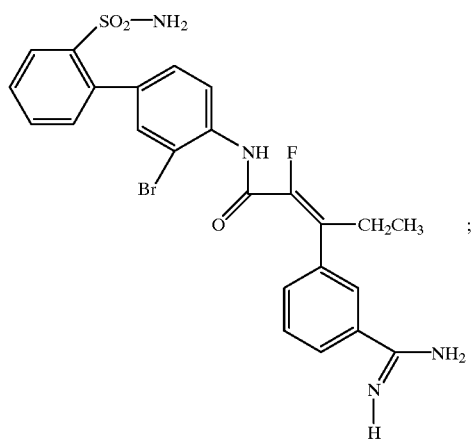
;
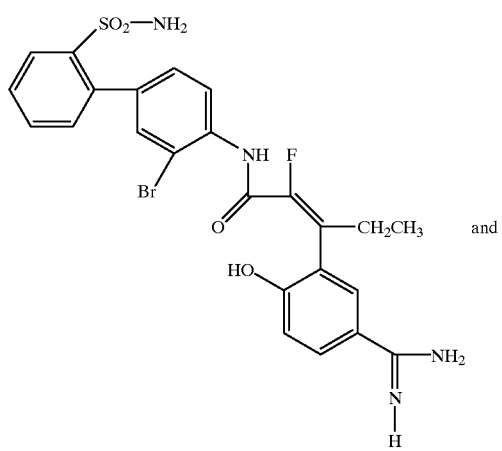
and
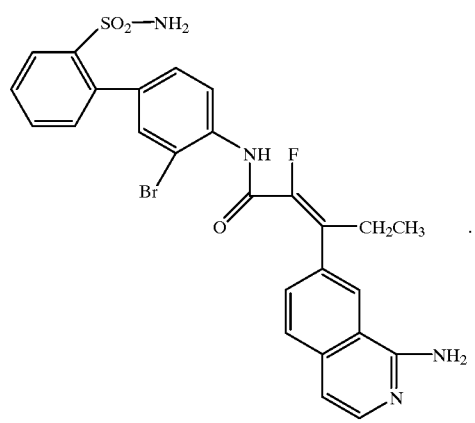
.

TABLE 10
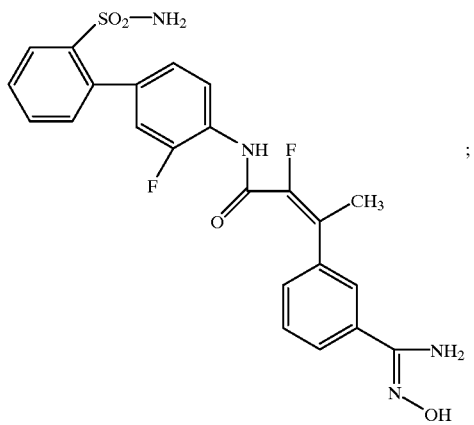
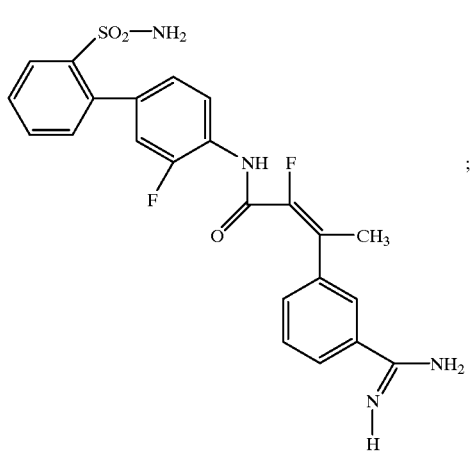
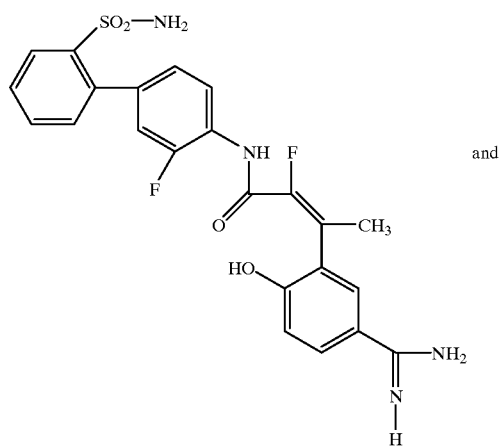
and
TABLE 10-continued
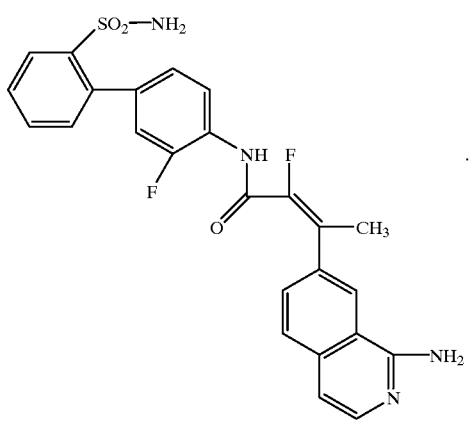
TABLE 11
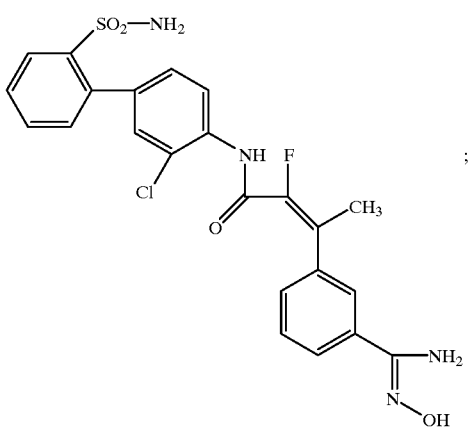
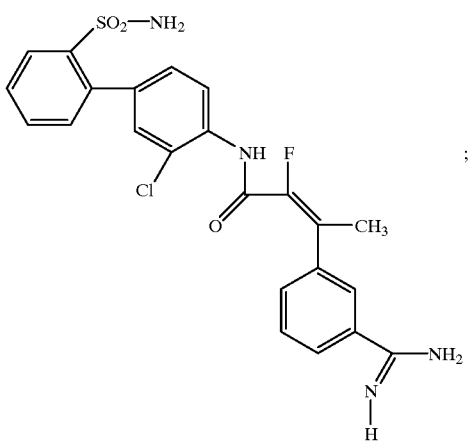

TABLE 11-continued
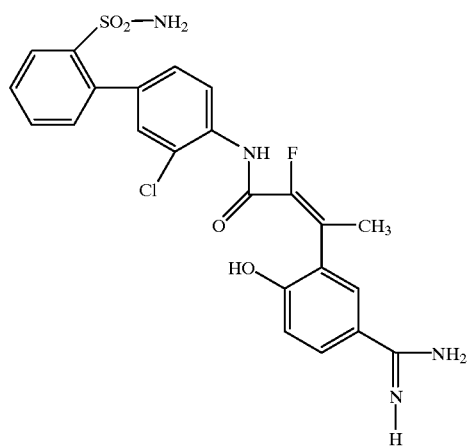
and
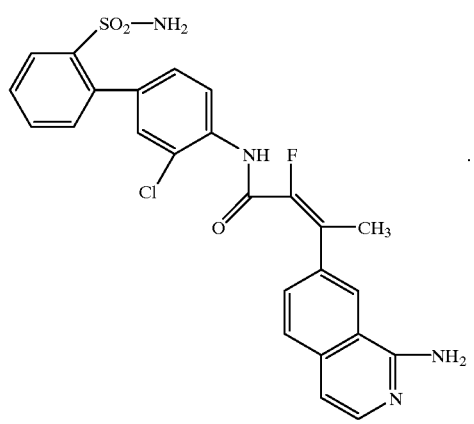
.
TABLE 12
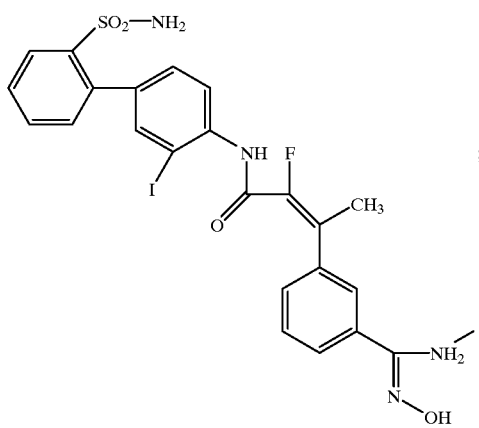
;
TABLE 12-continued
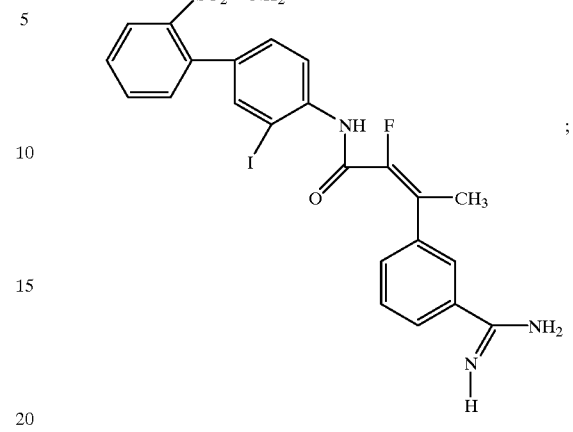
;
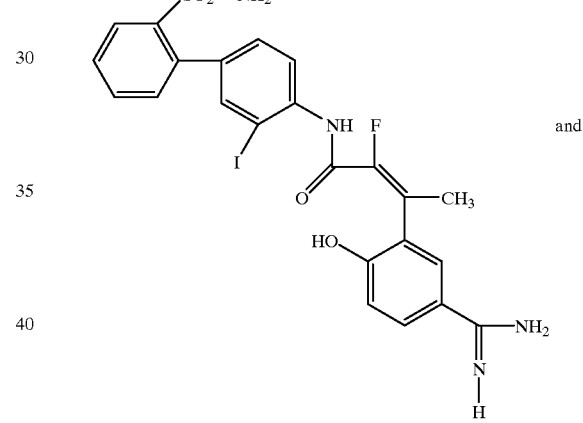
and
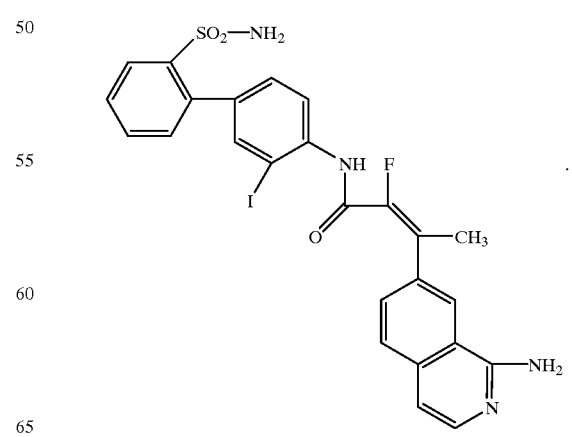
.

TABLE 13
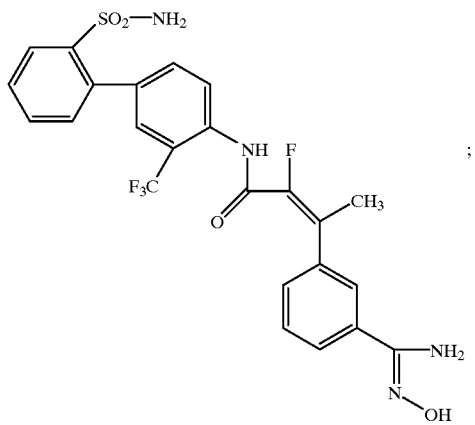
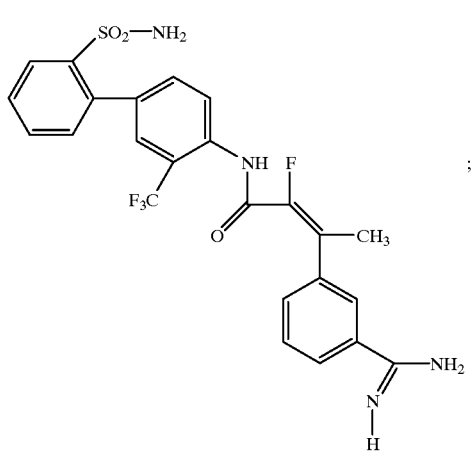
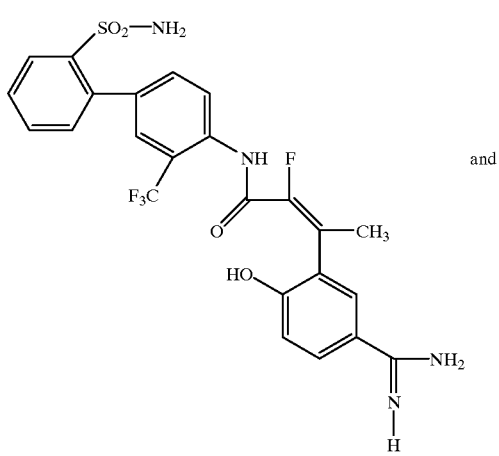
TABLE 13-continued
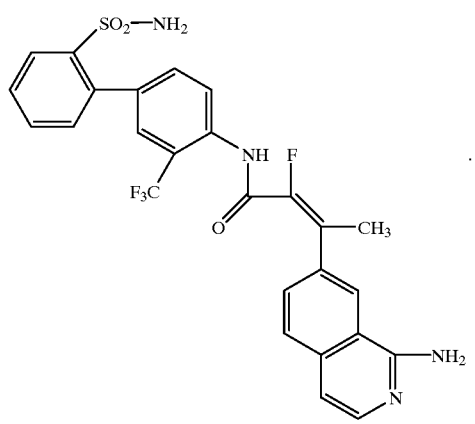
TABLE 14
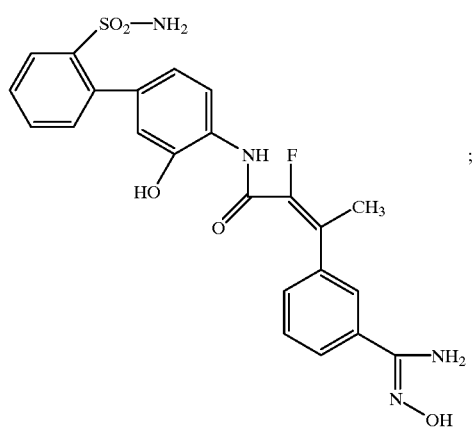
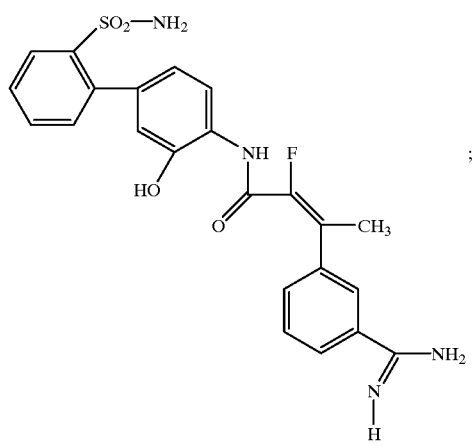

TABLE 14-continued
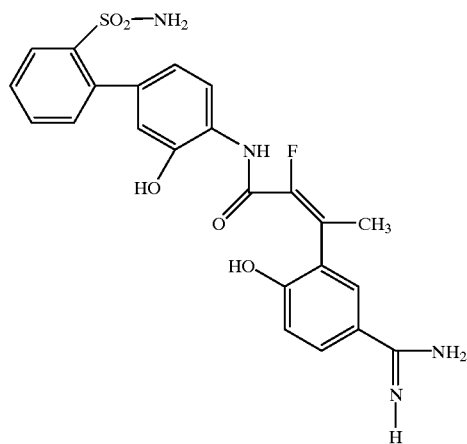
and
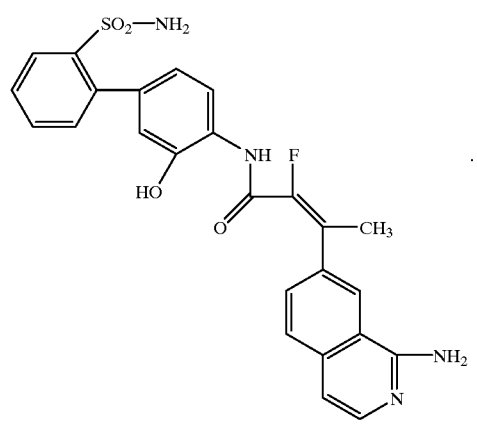
.
TABLE 15
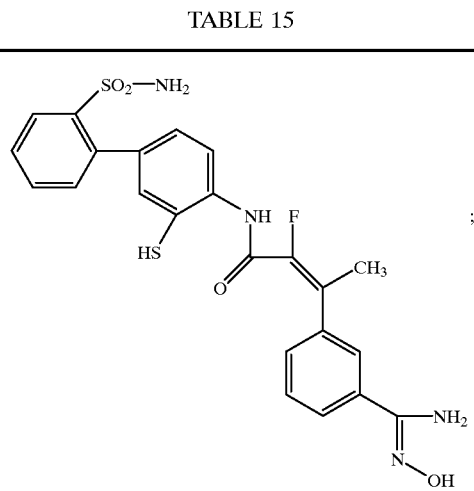
;
TABLE 15-continued
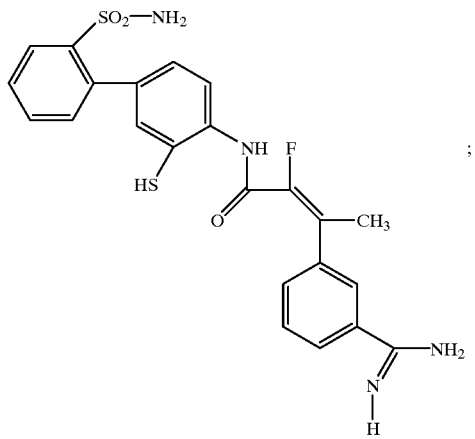
;
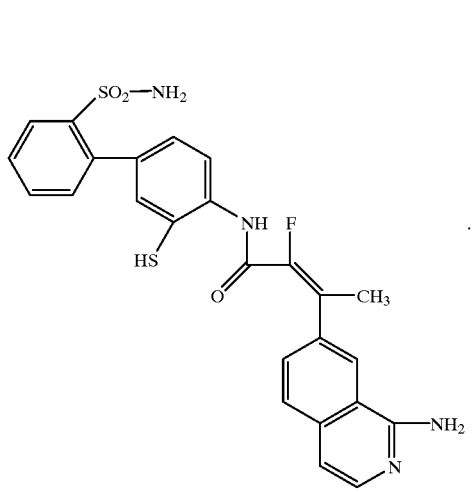
and
.

TABLE 16
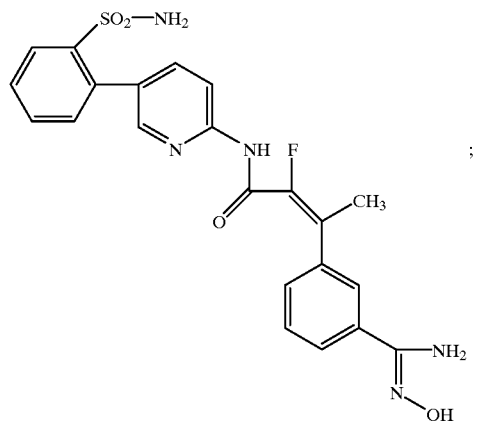
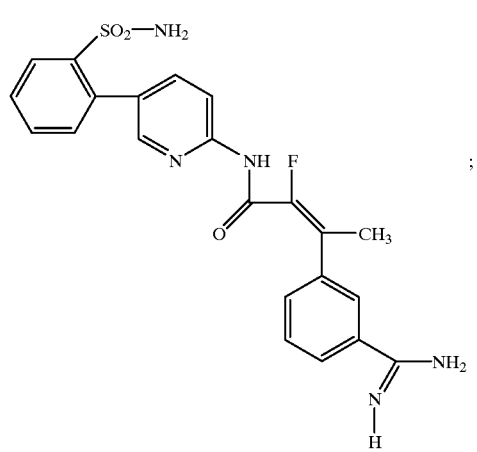
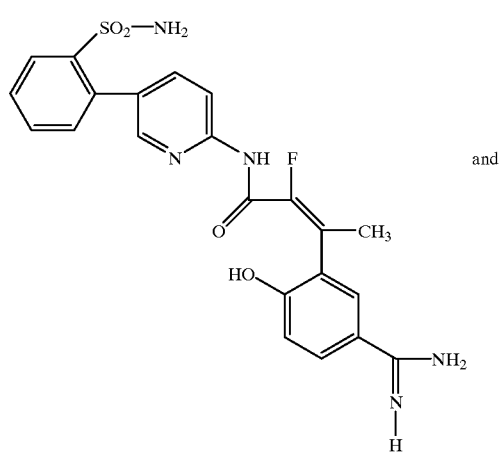
and
TABLE 16-continued
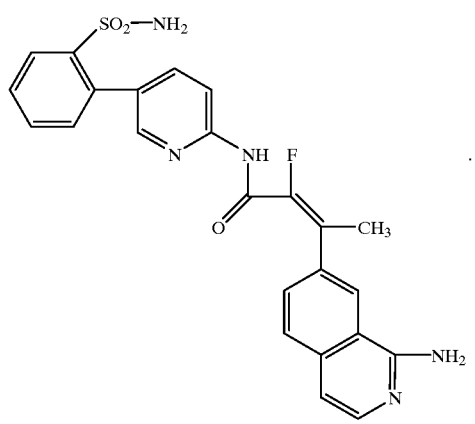
.
TABLE 17
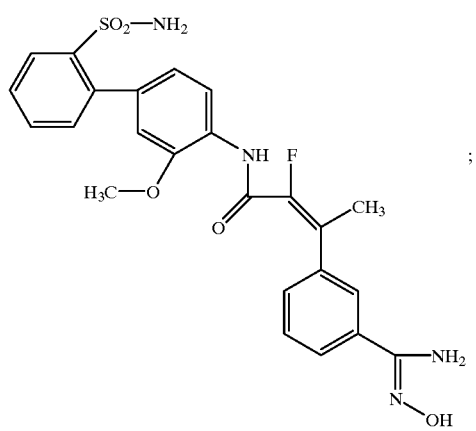
;
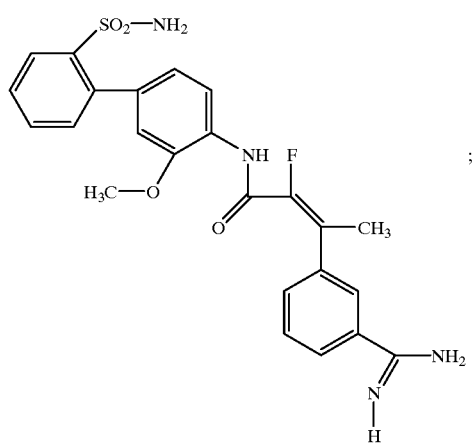
;

TABLE 17-continued
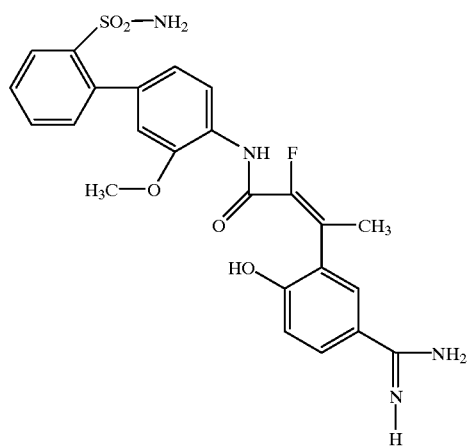
and
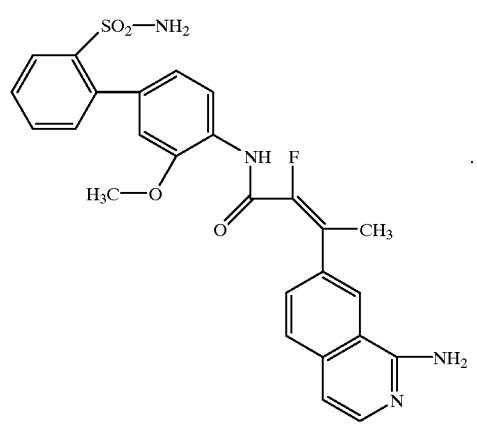
.
TABLE 18
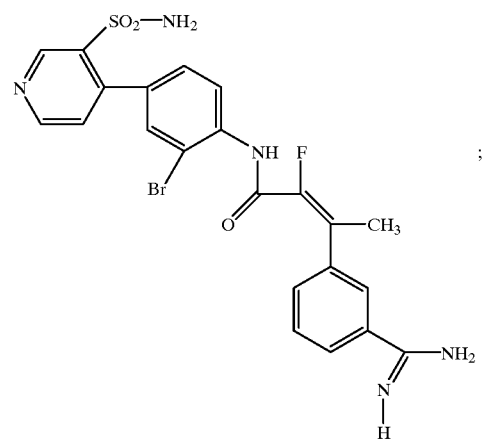
;
TABLE 18-continued
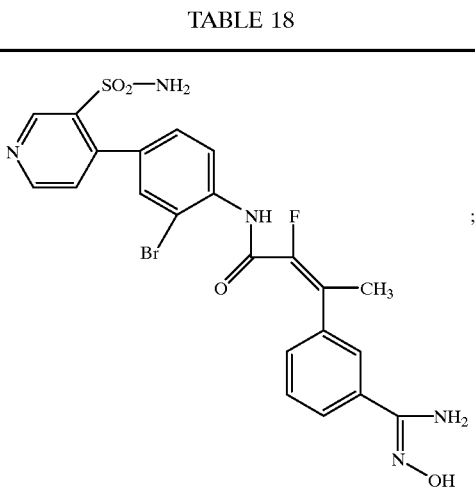
;
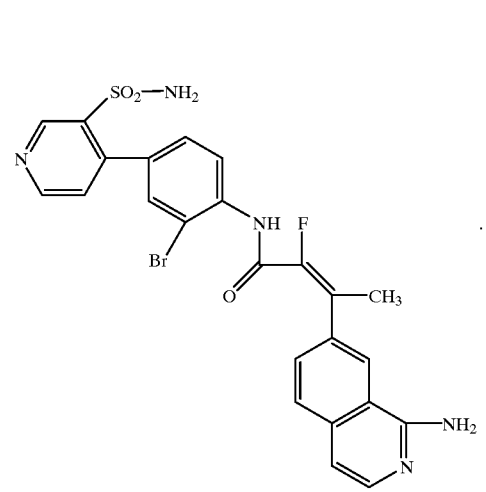
and
.

TABLE 19

[Structure: A—B—phenyl(2-Br)—NH—C(=O)—C(F)=C(CH₃)—isoquinoline-1-amine]

wherein A—B is:

- 2-methylphenyl-SO₂—NH₂
- 2-methylphenyl-SO₂—NH-alkyl
- 2-methylphenyl-SO₂—CH₃
- 2-methylphenyl-CH₂—NH₂
- 2-methylphenyl-C(=O)—NH₂
- 4-pyridyl
- 4-methylpyridin-3-yl-SO₂—NH₂
- 4-methylpyridin-3-yl-SO₂—NH-alkyl
- 4-methylpyridin-3-yl-SO₂—CH₃
- 4-methylpyridin-3-yl-SO₂—NH₂
- pyrrolidin-1-yl-C(=O)—
- pyrrol-1-yl—
- imidazol-1-yl—
- 4-methylpiperazin-1-yl—

TABLE 19-continued

[Structure: A—B—phenyl(2-Br)—NH—C(=O)—C(F)=C(CH₃)—isoquinoline-1-amine]

- 4-methylpiperazin-1-yl (with (  )₂ notation)—N—CH₃
- 4-methylpiperidin-1-yl—C(=NH)—NH₂
- 2-(SO₂—NH₂)phenyl-O—
- 4-methoxypiperidin-1-yl—C(=NH)—CH₃ and

- morpholin-4-yl—SO₂—

TABLE 20

[Structure: A—B—phenyl(2-Br)—NH—C(=O)—C(F)=C(CH₃)—phenyl-C(=N—OH)—NH₂]

wherein A—B is:

- 2-methylphenyl-SO₂—NH₂;
- 2-methylphenyl-SO₂—NH₂—alkyl;
- 2-methylphenyl-SO₂—CH₃;
- 2-methylphenyl-CH₂—NH₂;

TABLE 20-continued
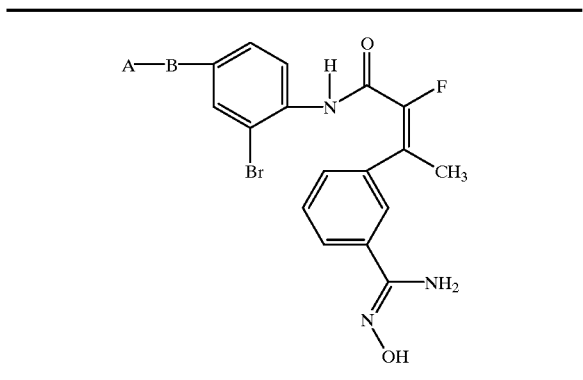
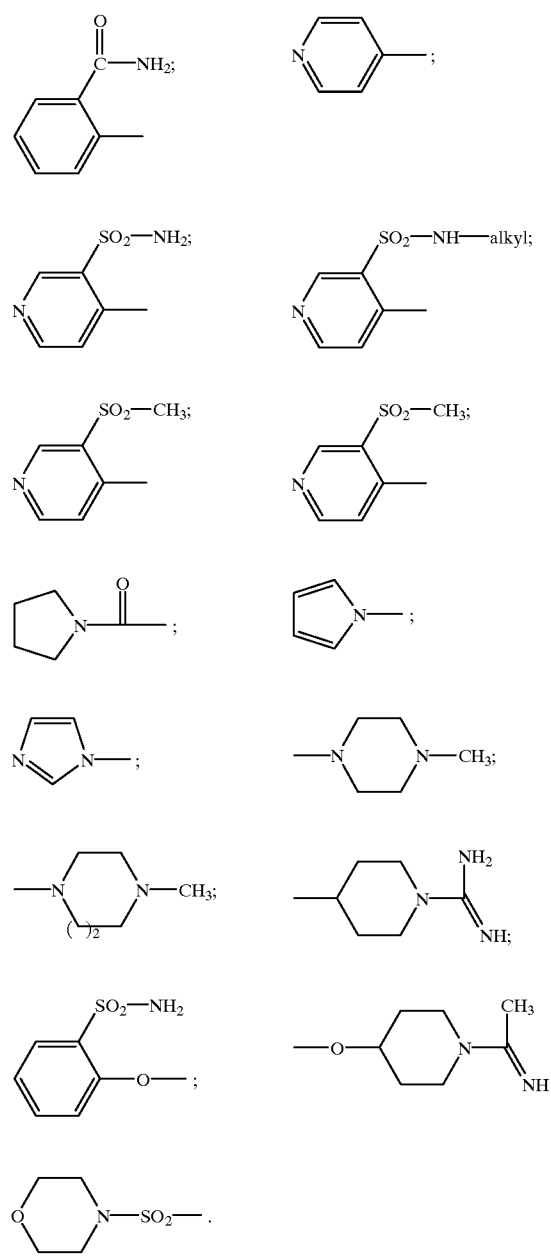
TABLE 21
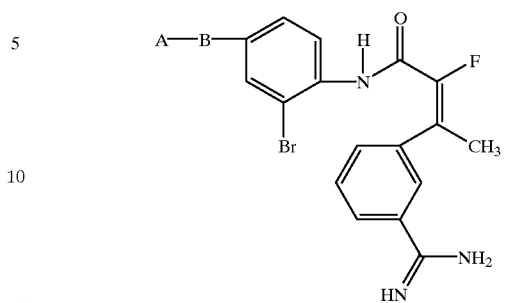
wherein A—B is:

TABLE 21-continued
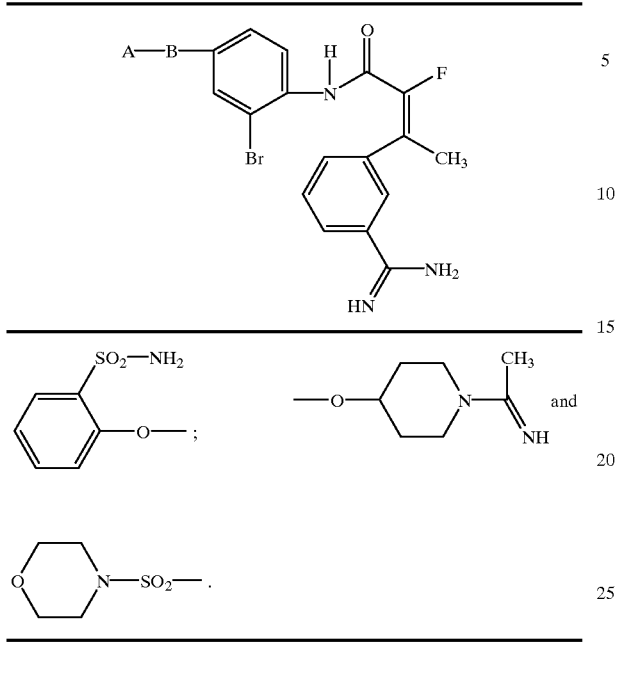
TABLE 22
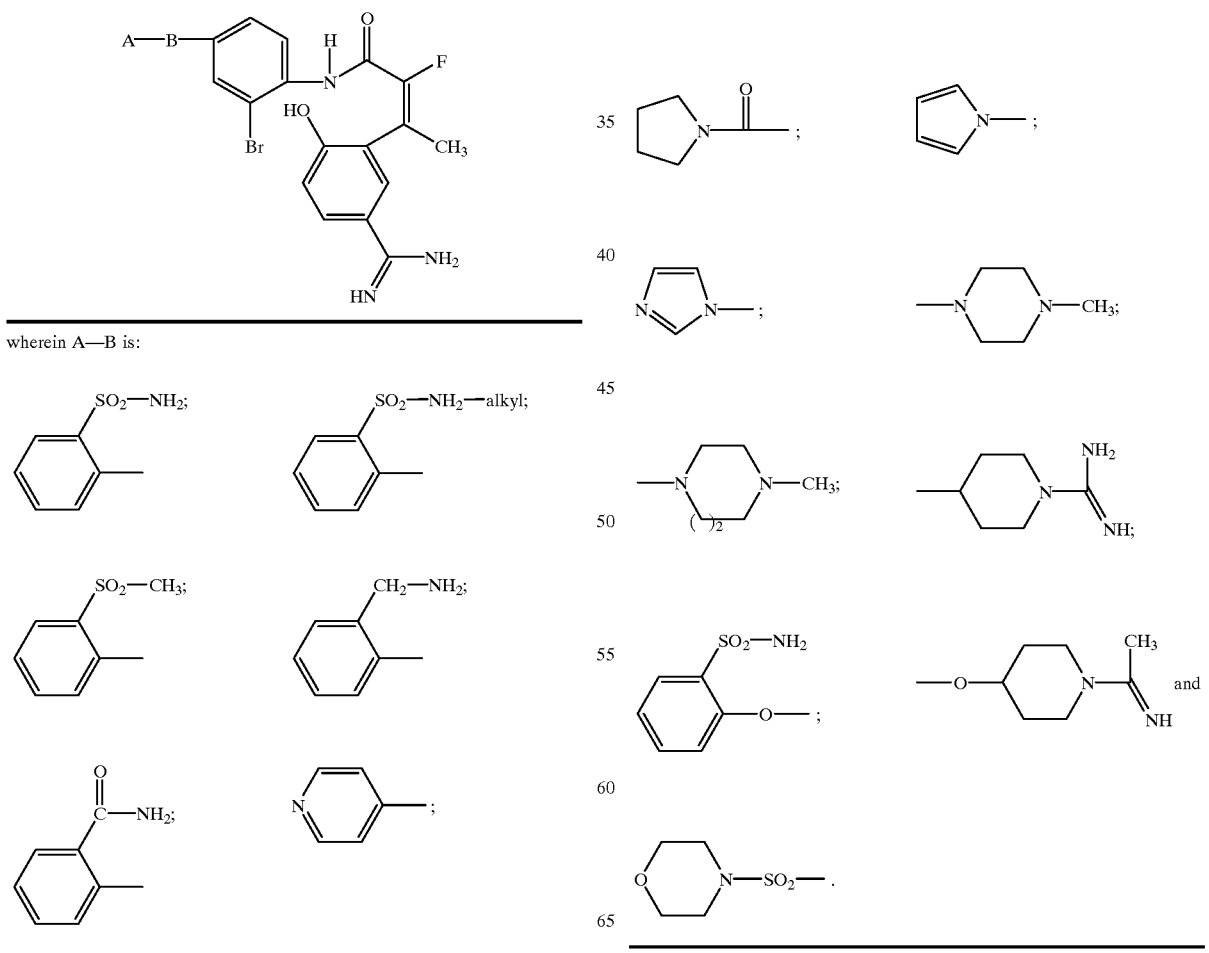

TABLE 23

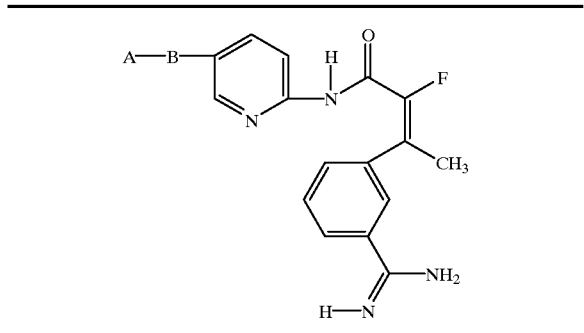

wherein A—B is:

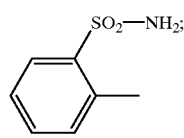 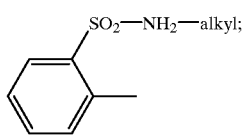

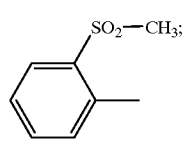 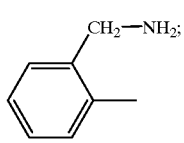

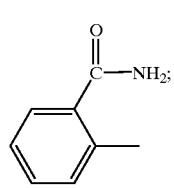 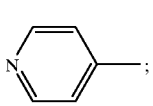

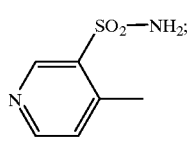 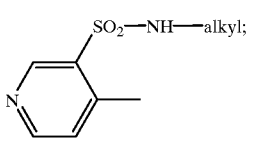

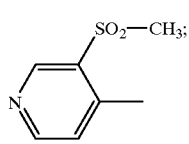 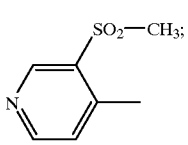

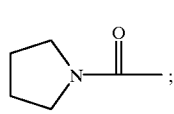 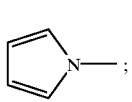

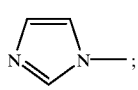 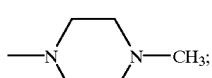

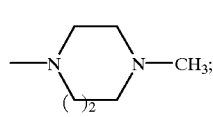 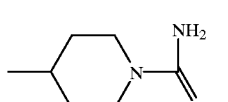

TABLE 23-continued

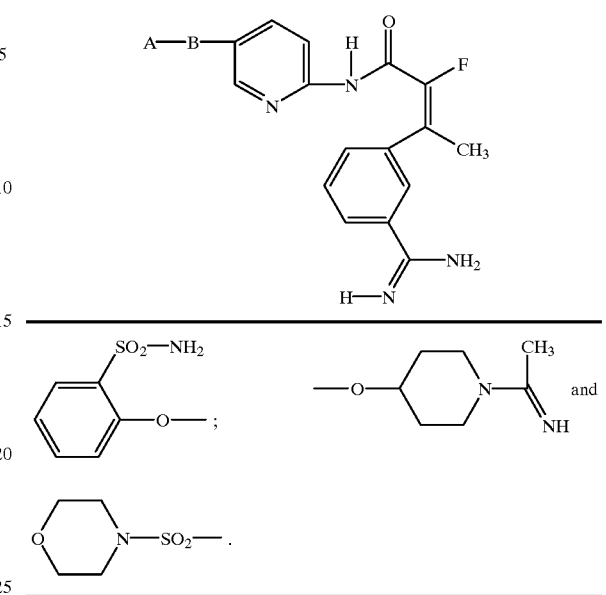

While the above invention shows the ethylene bridge having a "CIS" formation, compounds wherein such substituents are in the trans position are also envisioned. Further, when the above compound examples are shown with the ethylene bridge substituents as —F and —CH$_3$, one should also envision position isomers, halogen homologs, alkyl homologs and trihaloalkyl homologs independently as the ethylene bridge substituents.

This invention also encompasses all pharmaceutically acceptable isomers, salts, hydrates and solvates of the compounds of formulas I–IX, et seq. In addition, the compounds of formulas I–IX, et seq., can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

Compounds of the present invention can be synthesized in many ways known by those skilled in the art of organic synthesis. Preferred methods include, but not limited to, those described below. It will be recognized by those skilled in the art of organic synthesis that functional groups of the molecules should be consistent with the transformation conditions. Sometimes it is necessary that the functional groups need to be protected by protecting groups known by those skilled in the art. Examples of suitable protecting groups and their use are described in "Protective Groups in Organic Synthesis", Wiley and Sons, 1999 (authors Greene and Wuts). It is also understood by those skilled in the art that a successful synthesis sometimes requires a judgement to change the sequence of the synthetic steps in order to obtain the wanted compounds effectively.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

Non-limiting exemplary synthesis Schemes 1–6 are outlined directly below, and specific steps are described in the Examples. The reaction products are isolated and purified by conventional methods, typically by solvent extraction into a compatible solvent. The products may be further purified by column chromatography or other appropriate methods.

Scheme 1

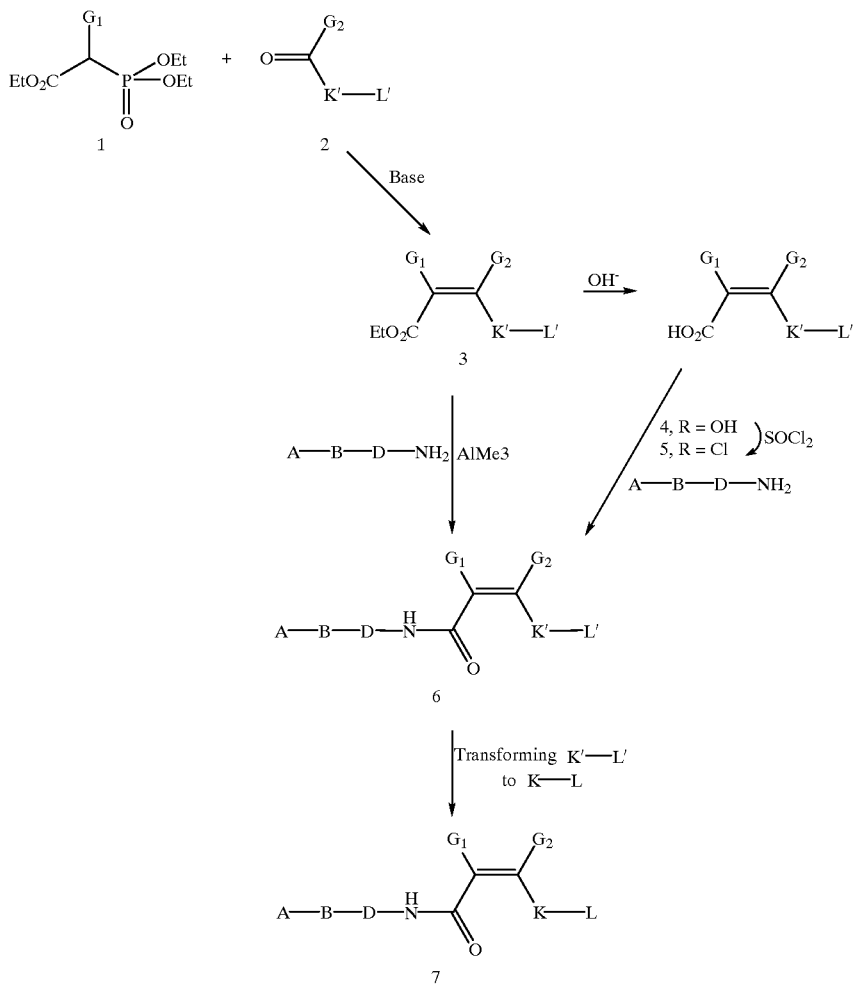

A large number of compounds of the present invention can be prepared by Horner-Wadsworth-Emmons (HWE) reaction and Wittig reaction, as shown in Scheme 1, above. In this method, a phosphonoacetate 1 was condensed with a ketone or aldehyde 2 in the presence of a base such as potassium bis(trimethylsilyl)amide or sodium hydride in an anhydrous aprotic solvent such as tetrahydrofuran at a temperature preferably ranging from −78 C to boiling point of the solvent, to give the acrylate 3. The fragment A—B—D—NH2 could be coupled to the acrylate 3 by using Weinreb conditions to produce acrylamide 6. Alternatively, the acrylate 3 could be hydrolyzed to the acid 4, which was then coupled to A—B—D—NH2 through a choice of coupling reagents such as BOP. Alternatively, the acid 4 could be converted to the corresponding acid chloride 5 by employing reagents used for such transformation, such as thionyl chloride or oxalyl chloride. The acid chloride 5 was then allowed to react with A—B—D—NH2 in the presence of a base to take up HCl generated. If needed, K'—L' in the acrylamide 6 would be transformed to K—L in the final compound 7 (e.g., transforming cyanophenyl to amidinophenyl, or isoquinoline to 1-aminoisoquinoline). Usually, HWE reactions produce both E- and Z-isomers of acrylate 3. To obtain a pure regioisomer of the final product, separation of the isomers may be achieved at either the final step or at intermediate stage wherever the separation could be done more conveniently, by chromatograph or other methods such as recrystallization.

Knoevenagel reaction was one of the useful methods for synthesizing compounds of this invention. As shown in Scheme 2, in this reaction, alpha-G1 acetate 8 (where G1 was usually a stabilizing group such as carbonyl, alkoxycarbonyl, cyano, pyridinyl, sulfonyl) could be condensed with a ketone or aldehyde 2 in the presence of a base such as piperidine, or potassium t-butoxide in solvents such as toluene, ethanol, t-butanol at a temperature preferably ranging from room temperature to the boiling point of the solvent of selection, with removal of generated water, for example by Dean-Stark apparatus, or use of molecular sieves, to produce the acrylate 3, usually as a mixture of E- and Z-isomers. Separation of the isomers could be achieved at either the final step or at intermediate stage wherever the separation could be done more conveniently, by chromatograph or other methods such as recrystallization. Elaboration of intermediate 3 to final product 7 has been described previously in Scheme 1.

Scheme 2

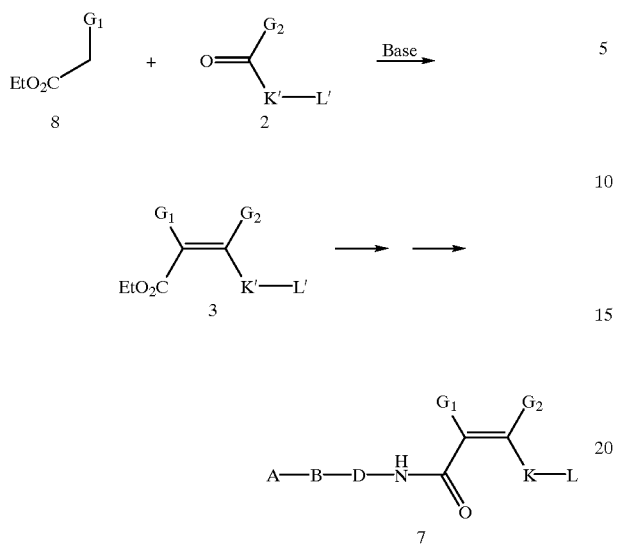

Alternatively, the compounds of this invention could be synthesized by the method outlined in Scheme 3. This method involved palladium catalyzed Suzuki or Stille coupling reaction of a vinyl triflate 9 with an organoboronic acid or an organotin reagent, to generate acrylate 3. The triflate 9 could be readily prepared from a beta-keto ester 10 by treatment of trifluoromethanesulfonic anhydride in the presence of triethylamine. Acrylate 3 could be similarly converted to the product 7 as described previously in Scheme 1.

Scheme 3

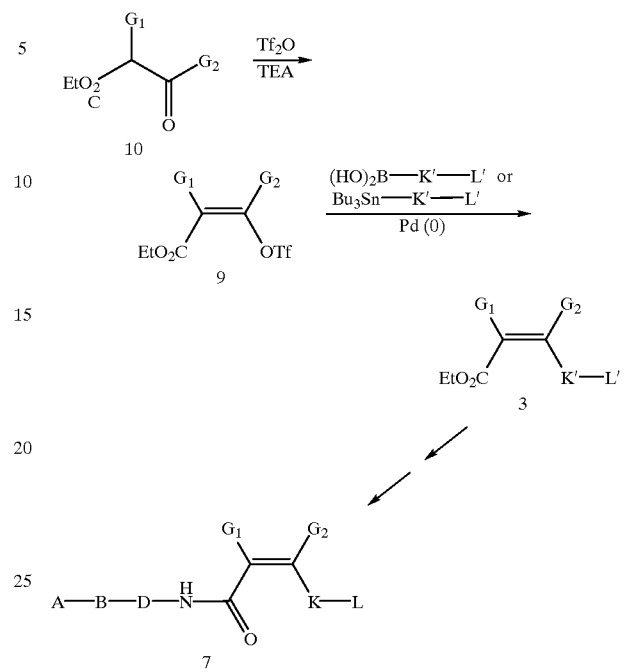

Erlenmeyer azalactone reaction could be used to synthesize compounds of this invention where $G1=NHC(O)R^2$ as shown in Scheme 4. This synthesis involved condensation of an aldehyde or ketone 2 with an N-acylglycine derivative 11 in the presence of acetic anhydride and sodium acetate, to produce the azalactone 12. Weinreb reaction of the azalactone with A—B—D—NH2 would give the acrylamide 13. If needed, K'—L' in the acrylamide 13 would be transformed to K—L in the final compound 14.

Scheme 4

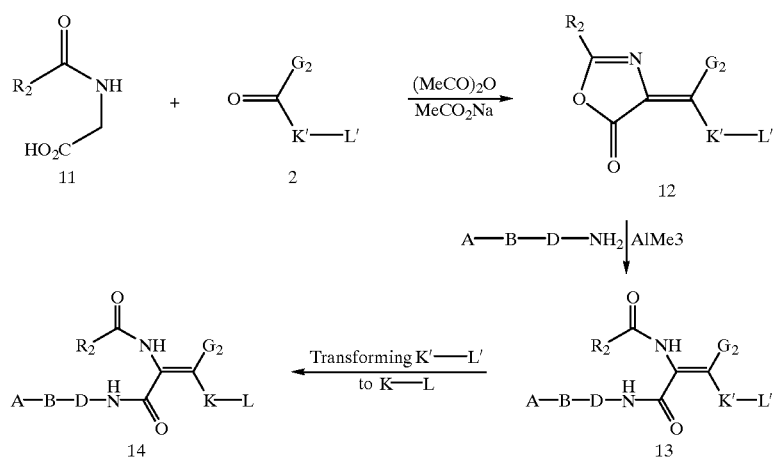

Stobbe reaction could be employed to synthesize compounds of this invention where $G1=CH_2CO_2R^1$ and $CH_2CONR^1R^2$ as shown in Scheme 5. This synthesis involved condensation of an aldehyde or ketone 2 with diethyl succinate in the presence of a base such as potassium t-butoxide in a solvent such as t-butanol at reflux, with removal of generated water, for example by Dean-Stark apparatus, or use of molecular sieves, to produce the intermediate 15. An amine $R_1R_2NH$ could be coupled to the free carboxylic group of 15 by an activating reagent such as BOP to give the amide 16. The fragment A—B—D—NH2 was then coupled to the ester group of 16 through Weinreb reaction to give the acrylamide 17. If needed, K'—L' in the acrylamide 17 would be transformed to K—L in the final compound 18.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an Scheme 5

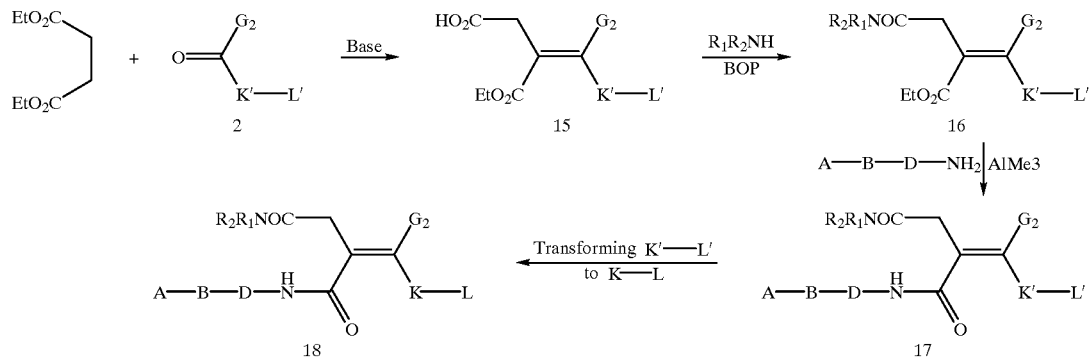

For compounds of this invention where $E=OCH_2$, $NR^5CH_2$, $SCH_2$, $SOCH_2$ and $SO_2CH_2$, the ester group of acrylate 3 (as shown in Scheme 6) could be reduced to hydroxymethyl group by a reducing reagent such as lithium aluminum hydride. Mesylation of the hydroxyl group of 19 followed by nucleophilic substitution of the allylic mesylate 20 by A—B—D—X (X is O, N, S nucleophile) would give the X-linked compound 21. For X=S, the sulfide could be oxidized to corresponding sulfoxide and sulfone, respectively, by an oxidizing reagent such as mCPBA. If needed, K'—L' in compound 21 would be transformed to K—L in the final compound 22.

ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this inven- Scheme 6

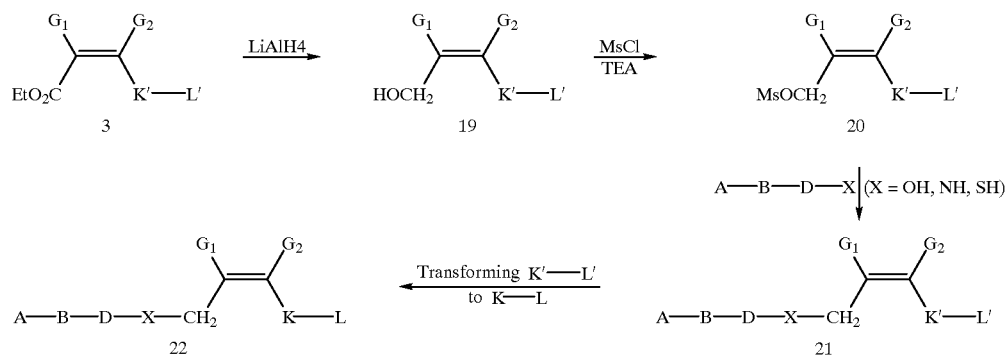

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

tion can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without fuher description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1
Preparation of (2E)-N-{4-[(2-aminosulfonyl)phenyl]phenyl}-3-(3-amidinophenyl)acrylamide

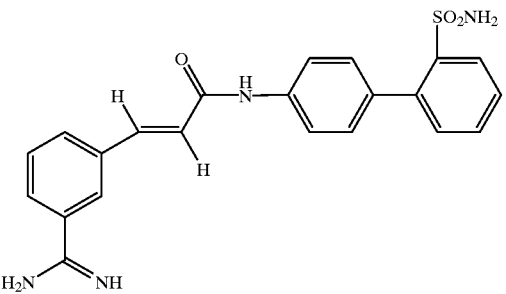

A. Preparation of (tert-butyl)(phenylsulfonyl)amine.

To a solution of benzenesulfonyl chloride (30.00 g, 169.86 mmol) in 100 ml DCM, in an ice bath, was added butyl amine (18 ml, 171.28 mmol), then triethylamine(35 ml, 251.11 mmol), drop wise via addition funnel. This was allowed to warm to room temperature over 3 hr. The mixture was then filtered and the filtrate was concentrated in vacuo. The pale yellow solid (35.03 g, 164.46 mmol, 97%) was then rinsed with minimal amounts of DCM. ES-MS (M+Na)+= 236.

B. Preparation of 2-[(tert-butyl amino)sulfonyl]phenyl boronic acid

To (tert-butyl)(phenylsulfonyl)amine (17.43 g, 81.83 mmol) in 180 ml dry THF in an ice bath was added nBuLi (66 ml, 2.5M in hexanes) via addition funnel. Then triisopropyl borate (33 ml, 143.06 mmol) was added via addition funnel. The mixture was warmed to room temperature and allowed to stir for 4 hr. The reaction mixture was then cooled in an ice bath before HCL (82 ml, 3M) was added dropwise. This was allowed to stir at room temperature for 3 hr. The mixture was then put in the freezer over the weekend. The reaction was then warmed to room temperature and extracted with ether. The aqueous layers were washed twice more with ether. The combined organic layers were washed three times with 5M NaOH aqueous solution. The combined basic layers were acidified to pH=1 with 6M HCL solution. These acidified layers were then extracted three times with ether. These ether layers were then dried over MgSO4, filtered, then concentrated in vacuo to about 50 ml solution. To this solution was added hexanes and a minimal amount of ethyl acetate. A white precipitate is observed and the mixture in stored in the freezer to allow for crystallization. The white solid is then filtered and collected (14.65 g, 57mml, 70%) ES-MS(M+H)+=258.

C. Preparation of {[2-(4-aminophenyl)phenyl]sulfonyl}(tert-butyl)amine

To a solution of 2-[(tert-butyl amino)sulfonyl]phenyl boronic acid (6.00 g, 23.35 mmol) in 120 ml toluene was added water (16 ml), isopropanol (60 ml), and NaOH (40 ml, 5M aqueous solution). To this were added 4-bromoaniline and Pd(Ph3P)4. This heterogeneous mixture is then refluxed for 6 hr, then stirred at room temperature over night before refluxing for another 1.5 hr. The reaction mixture is then extracted with water and ethyl acetate. The aqueous layer is extracted twice with ethyl acetate. The organic layers are then dried over MgSO4, filtered and concentrated in vacuo. The crude residue is purified by silica gel flash chromatography. The desired product can be eluded with 30% ethyl acetate in hexanes and concentrated to an orange solid (5.06 g, 16.65, 71%). ES-MS(M+H)+=305.

D. Preparation of methyl 3-(3-cyanophenyl) acrylate

To a solution of 3-cyanobenzaldehyde(1.00 g, 7.64 mmol) in DCM (30 ml) was added carbomethoxymethylene triphenylphosphorane (2.55 g, 7.63 mmol). The reaction mixture was allowed to stir at room temperature for 2.5 hr before being concentrated. The residue was dissolved in minimal amounts of DCM and filtered over a pad of silica gel with 20% ethyl acetate in hexanes. The filtrate was concentrated to a white powder (1.09 g, yield 76%). ES-MS(M+H)+=188.

E. Preparation of N-{4-[(2-tert-butylaminosulfonyl)phenyl]phenyl}-3-(3-cyanophenylacrylamide To a stirring solution of {[2-(4-aminophenyl)phenyl]sulfonyl}(tert-butyl)amine (80 mg, 0.189 mmol) in DCM(5 ml) was added trimethylaluminum(0.4 ml of 2M solution in hexane, 0.263 mmol) dropwise. This was allowed to stir for 2.5 hr before methyl 3-(3-cyanophenyl) acrylate (51 mg, 0.272 mmol) was added. The reaction was allowed to stir overnight before being quenched with 1N HCl. The aqueous layer was washed twice with EtOAc. The combined organic layers were dried over MgSO4, filtered and concentrated. The residue was purified by Preparatory HPLC to yield product (22.9 mgs, yield 19%).

F. Preparation of (2E)-N-{4-[(2-aminosulfonyl)phenyl]phenyl}-3-(3-amidinophenyl-3-acrylamide To a solution of compound N-{4-[(2-tert-butylaminosulfonyl)phenyl]phenyl}-3-(3-cyanophenylacrylamide (22 mg, 0.049 mmol) in anhydrous MeOH (3 ml) cooled in ice bath, hydrogen chloride gas was bubbled to saturation. The solution was then stirred at room temperature overnight. It was concentrated in vacuo, the residue was dissolved in anhydrous MeOH (2mL). To the solution, NH4OAc (25 mg, 0.325 mmol) was added. The mixture was refluxed for 3.5 hr, then concentrated in vacuo. The residue was purified by HPLC using a gradient of 5% CH3CN in H2O (containing 0.1% TFA) to 95% CH3CN over 60 min. Fractions containing the E-isomer product were pooled, and lyophilized to give a powder (7.4 mg, yield 35%).

Example 2

Preparation of (2Z)-N-{4-[(2-aminosulfonyl)phenyl]phenyl}-3-(3-amidinophenyl)-2-(pyridin-4-yl)acrylamide and (2E)-N-{4-[(2-aminosulfonyl)phenyl]phenyl}-3-(3-amidinophenyl)-2-pyridin-4-yl)acrylamide

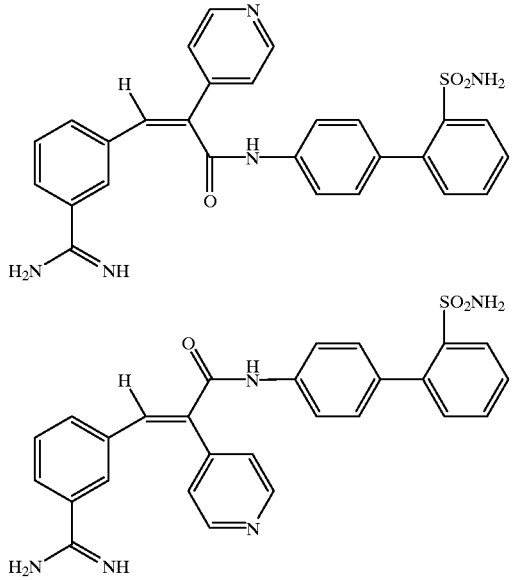

A. Preparation of (tert-butyl)(phenylsulfonyl)amine.

To a solution of benzenesulfonyl chloride (30.00 g, 169.86 mmol) in 100 ml DCM, in an ice bath, was added butyl amine (18 ml, 171.28 mmol), then triethylamine(35 ml, 251.11 mmol), drop wise via addition funnel. This was allowed to warm to room temperature over 3 hr. The mixture was then filtered and the filtrate was concentrated in vacuo. The pale yellow solid (35.03 g, 164.46 mmol, 97%) was then rinsed with minimal amounts of DCM. ES-MS (M+Na)+= 236.

B. Preparation of 2-[(tert-butyl amino)sulfonyl]phenyl boronic acid

To (tert-butyl)(phenylsulfonyl)amine (17.43 g, 81.83 mmol) in 180 ml dry THF in an ice bath was added nBuLi (66 ml, 2.5M in hexanes) via addition funnel. Then triisopropyl borate (33 ml, 143.06 mmol) was added via addition funnel. The mixture was warmed to room temperature and allowed to stir for 4 hr. The reaction mixture was then cooled in an ice bath before HCL (82 ml, 3M) was added dropwise. This was allowed to stir at room temperature for 3 hr. The mixture was then put in the freezer over the weekend. The reaction was then warmed to room temperature and extracted with ether. The aqueous layers were washed twice more with ether. The combined organic layers were washed three times with 5M NaOH aqueous solution. The combined basic layers were acidified to pH=1 with 6M HCL solution. These acidified layers were then extracted three times with ether. These ether layers were then dried over MgSO4, filtered, then concentrated in vacuo to about 50 ml solution. To this solution was added hexanes and a minimal amount of ethyl acetate. A white precipitate is observed and the mixture in stored in the freezer to allow for crystallization. The white solid is then filtered and collected (14.65 g, 57 mml, 70%) ES-MS(M+H)+=258.

C. Preparation of {[2-(4-aminophenyl)phenyl]sulfonyl}(tert-butyl)amine

To a solution of 2-[(tert-butyl amino)sulfonyl]phenyl boronic acid (6.00 g, 23.35 mmol) in 120 ml toluene was added water (16 ml), isopropanol (60 ml), and NaOH (40 ml, 5M aqueous solution). To this were added 4-bromoaniline and Pd(Ph3P)4. This heterogeneous mixture is then refluxed for 6 hr, then stirred at room temperature over night before refluxing for another 1.5 hr. The reaction mixture is then extracted with water and ethyl acetate. The aqueous layer is extracted twice with ethyl acetate. The organic layers are then dried over MgSO4, filtered and concentrated in vacuo. The crude residue is purified by silica gel flash chromatography. The desired product can be eluded with 30% ethyl acetate in hexanes and concentrated to an orange solid (5.06 g, 16.65, 71%). ES-MS(M+H)+=305.

D. Preparation of ethyl 3-(3-cyanophenyl)-2-(pyridin-4-yl)acrylate.

A solution of 3-cyanobenzonitrile (0.794 g, 6.046 mmol), ethyl 4-pyridylacetate (0.66 ml, 6.044 mmol) and ammonium acetate (0.564 g, 7.084 mmol) in acetic acid (4 ml) was refluxed for 4 hr. The reaction was cooled to room temperature and quenched with sat. NaHCO3. The mixture was extracted three times with ethyl acetate. The organic layers were dried over MgSO4, filtered and concentrated in vacuo. The product mixture was purified by a silica gel column. The mixture of isomers was collected (0.983 g, 58% yield).

E. Preparation of (2Z)-N-{4-[(2-aminosulfonyl)phenyl]phenyl}-3-(3-cyanophenyl)-2-(pyridin-4-yl)acrylamide and (2E)-N-{4-[(2-aminosulfonyl)phenyl]phenyl}-3-(3-cyanophenyl)-2-(pyridin-4-yl)acrylamide To a stirring solution of {[2-(4-aminophenyl)phenyl]sulfonyl}(tert-butyl)amine (0.195 g, 0.641 mmol) and ethyl 3-(3-cyanophenyl)-2-(pyridin-4-yl)acrylate (0.177 g, 0.636 mmol) in DCM(6 ml) was added trimethylaluminum (0.95 ml of 2M solution in hexane, 1.9 mmol) dropwise. This was allowed to stir overnight. The reaction was then quenched with 1N HCl to pH=0. The solid was filtered to 109 mg of the E isomer. The filtrate was extracted twice with DCM, dried over MgSO4 then filtered. The residue was purified on silica gel to yield 74 mg of Z isomer and 109 mg of E isomer. (E+Z isomer=183 mg, 54% yield.)

F. Preparation of (2Z)-N-{4-[(2-aminosulfonyl)phenyl]phenyl}-3-(3-amidinophenyl)-2-(pyridin-4-yl)acrylamide.

To a solution of compound (2Z)-N-{4-[(2-aminosulfonyl)phenyl]phenyl}-3-(3-cyanophenyl)-2-(pyridin-4-yl)acrylamide (73.8 mg, 0.137 mmol) in 1:1 anhydrous MeOH:CH2Cl2 (6 ml) cooled in ice bath, hydrogen chloride gas was bubbled to saturation. The solution was then stirred at room temperature overnight. It was concentrated in vacuo, the residue was dissolved in anhydrous MeOH (5mL). To the solution, NH4OAc (68 mg, 0.882 mmol) was added. The mixture was refluxed for 3 hr, then concentrated in vacuo. The residue was purified by HPLC using a gradient of 5% CH3CN in H2O (containing 0.1% TFA) to 95% CH3CN over 60 min. Fractions containing the product were pooled, and lyophilized to give a powder (21.7 mg, yield 32%).

G. Preparation of (2E)-N-{4-[(2-aminosulfonyl)phenyl]phenyl}-3-(3-amidinophenyl)-2-(pyridin-4-yl)acrylamide.

To a solution of compound (2E)-N-{4-[(2-aminosulfonyl)phenyl]phenyl}-3-(3-cyanophenyl)-2-(pyridin-4-yl)acrylamide (109 mg, 0.208 mmol) in 1:1 anhydrous MeOH:CH2Cl2 (6 ml) cooled in ice bath, hydrogen chloride gas was bubbled to saturation. The solution was then stirred at room temperature overnight. It was concentrated in vacuo, the residue was dissolved in anhydrous MeOH (5 mL). To the solution, NH4OAc (97 mg, 1.26 mmol) was added. The mixture was refluxed for 3 hr, then concentrated in vacuo. The residue was purified by HPLC using a gradient of 5% CH3CN in H2O (containing 0.1% TFA) to 95% CH3CN over 60 min. Fractions containing the product were pooled, and lyophilized to give a powder (100 mg, yield 97%).

Example 3

Preparation of (2Z)-N-(4-[(2-aminosulfonyl)phenyl]phenyl)-3-(3-amidinophenyl)-acrylamide.

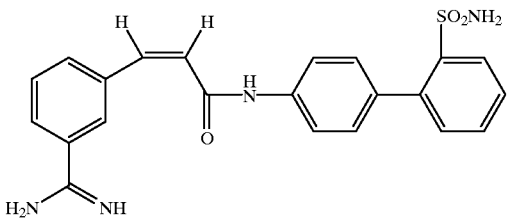

A. Preparation of (Z) methyl 3-cyanocinnamate

To a solution of bis(2,2,2-trifluoroethyl)(methoxycarbonylmethyl) phosphonate (1.00 g, 3.14 mmol) and 18-crown-6 (4.14 g, 15.7 mmol) in THF (50 mL) at −78 C, potassium bis(trimethylsilyl)amide (6.3 mL, 0.5 M in toluene, 3.15 mmol) was added dropwise. After the addition was completed, 3-cyanobenzaldehyde (0.412 g, 3.14 mmol) in THF (8 mL) was added. The mixture was stirred at −78 C for 30 min before it was quenched with aq. NH4Cl. Water and ether were added. Aqueous phase was separated, extracted with ether once more. The combined organic solutions were dried over Na2SO4, concentrated in vacuo to give a solid, which was purified by a silica gel column, first eluted with EtOAc/hexane (5/95), then with EtOAc/hexane (10/90) to give the titled compound (0.40 g) (yield: 68%). $^1$H NMR (CDCl3) 7.85 (s, 1H), 7.77 (d, 1H, J=8 Hz), 7.60 (d, 1H, J=8 Hz), 7.45 (t, 1H, J=8 Hz), 6.91 (d, 1H, J=12 Hz), 6.06 (d, 1H, J=12 Hz).

B. Preparation of (2Z)-N-(4-[(2-tert-butylaminosulfonyl)phenyl]phenyl)-3-(3-cyanophenyl)-acrylamide.

To a solution of 4-(2-tert-butylaminosulfonylphenyl)aniline (80 mg, 0.263 mmol) in CH2Cl2 (4 mL) at room temperature, trimethylaluminum (0.39 mL, 2.0 M in hexane, 0.78 mmol) was added dropwise. After the solution was stirred for 30 min at room temperature, compound (Z) methyl 3-cyanocinnamate (50 mg, 0.267 mmol) was added. The mixture was stirred at room temperature for 2 days. The solution was neutralized with 1N HCl (10 mL) to pH=1–2. Water and CH2Cl2 were added, and organic phase was separated, dried over Na2SO4, concentrated in vacuo to give a yellowish solid (120 mg) (yield: 98%), which was sufficiently pure to be used in the next reaction. MS 482 (M+Na)

C. Preparation of (2Z)-N-(4-[(2-aminosulfonyl)phenyl]phenyl)-3-(3-amidinophenyl)-Acrylamide.

To a solution of compound (2Z)-N-(4-[(2-tert-butylaminosulfonyl)phenyl]phenyl)-3-(3-cyanophenyl)-acrylamide (120 mg, 0.261 mmol) in anhydrous MeOH (10 mL) cooled in ice bath, hydrogen chloride gas was bubbled to saturation. The solution was then stirred at room temperature overnight. It was concentrated in vacuo, the residue was dissolved in anhydrous MeOH (4 mL). To the solution, NH4OAc (120 mg, 1.56 mmol) was added. The mixture was heated to reflux for 0.5 h. It was concentrated in vacuo. The residue was purified by HPLC using a gradient of 5% CH3CN in H2O (containing 0.1% TFA) to 80% CH3CN over 60 min. Fractions containing the desired product were pooled, and lyophilized to give a powder (50 mg, yield: 46%). MS 421 (M+H). $^1$H NMR (CD3OD) 8.13–8.05 (m, 2H), 7.91 (d, 1H, J=8 Hz), 7.72 (d, 1H, J=8 Hz), 7.64–7.56 (m, 4H), 7.52 (t, 1H, J=8 Hz), 7.39 (d, 2H, J=8 Hz), 7.33 (d, 1H, J=8 Hz), 7.02 (d, 1H, J=12 Hz), 6.37 (d, 1H, J=12 Hz).

Example 4
Preparation of N-(4-[(2-aminosulfonyl)phenyl]phenyl)-2-methoxycarbonyl-3-(3-amidinophenyl)-acrylamide.

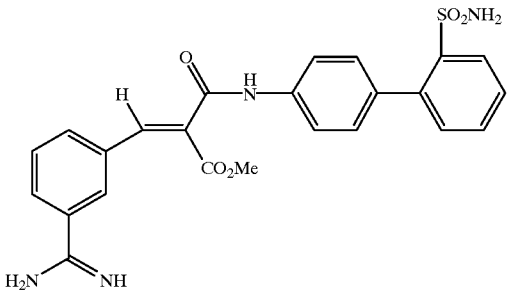

A. Preparation of tert-butyl 2-methoxycarbonyl-3-(3-cyanophenyl)-acrylate.

To a solution of 3-cyanobenzaldehyde (0.700 g, 5.34 mmol) and t-butyl methyl malonate (0.845 mL, 5.00 mmol) in toluene (40 mL), piperidine (0.500 mL, 5.06 mmol) was added. The mixture was heated to reflux overnight. Dean-Stark apparatus was used to remove generated water. Ethyl acetate (50 mL) and 0.5 N HCl (50 mL) were added. Organic phase was separated, washed with saturated aq. NaHCO3, dried over Na2SO4, concentrated in vacuo to give an oil. The oil was dry-packed onto a silica gel column, eluted with hexane first, then with 5% to 10% EtOAc in hexane gradually to give the desired product as a mixture of E and Z isomers (0.44 g) (yield: 31%). $^1$H NMR (CDCl3) 7.78–7.57 (m, 3H), 7.57–7.43 (m, 1H), 3.88 (s, 3H, minor isomer), 3.85 (s, 3H, major isomer), 1.53 (br. s, 9H).

B. Preparation of N-(4-[(2-tert-butylaminosulfonyl)phenyl]phenyl)-2-methoxycarbonyl-3-(3-cyanophenyl)-acrylamide.

Compound tert-butyl 2-methoxycarbonyl-3-(3-cyanophenyl)-acrylate (0.220 g, 0.767 mmol) was dissolved in TFA (6 mL). It was allowed to stand at room temperature for 2 h. TFA was removed in vacuo to give a solid. The solid was dissolved in anhydrous DMF (7 mL). To the solution, 4-(2'-tert-butylaminosulfonylphenyl)aniline (0.242 g, 0.796 mmol) and triethylamine (0.200 mL, 1.44 mmol) were added, followed by addition of BOP (0.416 g, 0.940 mmol). The mixture was then stirred room temperature overnight. Water and ethyl acetate were added. Organic phase was separated, washed with saturated aq. NaHCO3, dried over Na2SO4, concentrated in vacuo to give a solid (0.391 g) (yield: 99%). It was sufficiently pure to be used in the next reaction.

C. Preparation of N-(4-[(2-aminosulfonyl)phenyl]phenyl)-2-methoxycarbonyl-3-(3-amidinophenyl)-acrylamide.

To a solution of compound N-(4-[(2-tert-butylaminosulfonyl)phenyl]phenyl)-2-methoxycarbonyl-3-(3-cyanophenyl)-acrylamide (0.390 g, 0.750 mmol) in anhydrous MeOH cooled in ice bath, hydrogen chloride gas was bubbled to saturation. The solution was then stirred at room temperature overnight. It was concentrated in vacuo, the residue was dissolved in anhydrous MeOH (6 mL). To the solution, NH4OAc (0.450 g, 5.84 mmol) was added. The mixture was heated to reflux for 0.5 h. It was concentrated in vacuo. The residue was purified by HPLC using a gradient of 5% CH3CN in H2O (containing 0.1% TFA) to 95% CH3CN over 90 min. Fractions containing the desired product were pooled, and lyophilized to give a powder (60 mg) (yield: 17%). MS 479 (M+H). $^1$H NMR (CD3OD) 8.07 (d, 1H, J=8 Hz), 7.94 (s, 1H), 7.90 (d, 1H, J=8 Hz), 7.82 (d, 1H, J=8 Hz), 7.68 (t, 1H, J=8 Hz), 7.58 (t, 1H, J=8 Hz), 7.50 (t, 1H, J=8 Hz), 7.34 (s, 4H), 7.27 (d, 1H, J=8 Hz), 3.83 (s, 3H).

Example 5
Preparation of (2E)-N-{4-[(2-aminosulfonyl)phenyl]phenyl}-3-(3-amidinophenyl)-2-fluoro-3-methylacrylamide, (2Z)-N-{4-[(2-aminosulfony)phenyl]phenyl}-3-(3-amidinophenyl)-2-fluoro-3-methylacrylamide and (2E)-N-{4-[(2-aminosulfonyl)phenyl]phenyl}-3-(3-aminocarbonylphenyl)-2-fluoro-3-methylacrylamide

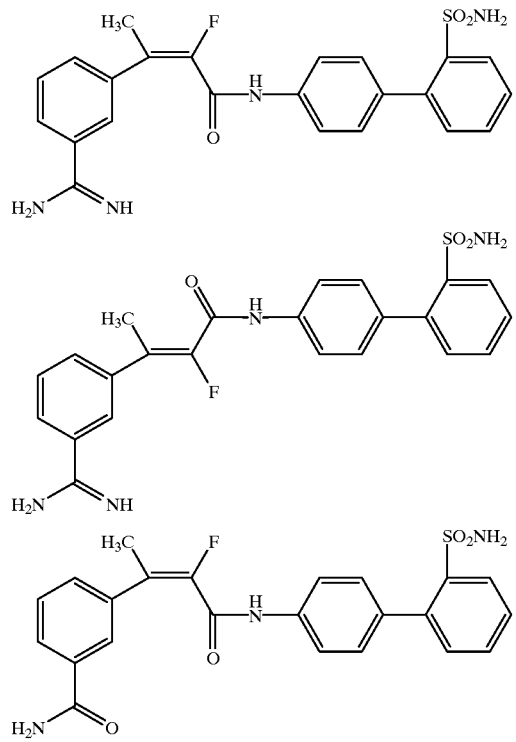

A. Preparation of ethyl 3-(3-cyanophenyl)-2-fluoro-3-methylacrylate.

To a solution of triethyl 2-fluoro-2-phosphonoacetate (0.838 mL, 4.13 mmol) in anhydrous THF (25 mL) at −78 C, potassium bis(trimethylsilyl)amide (0.5 M in toluene, 10.0 mL, 5.00 mmol) was added dropwise. After 10 min following the addition, a solution of 3-acetylbenzonitrile (0.600 g, 4.14 mmol) in THF (8 mL) was added dropwise. The reaction mixture was stirred at −78 C for 30 min, then removed to room temperature, and stirred at the temperature overnight. Aqueous NH4Cl and EtOAc were added. Organic phase was separated, washed with sat. NaCl, dried over Na2SO4, concentrated in vacuo to give an oil as a mixture of E- and Z-isomers in a ratio of 5:1 (0.920 g, yield: 95%), which was pure enough to be used in the next reaction. MS 234 (M+H).

B. Preparation of N-{4-[(2-tert-butylaminosulfonyl)phenyl]phenyl}-3-(3-cyanophenyl)-2-fluoro-3-methylacrylamide.

To the solution of 4-(2'-tert-butylaminosulfonylphenyl)aniline (0.195 g, 0.641 mmol) in CH2Cl2 (8 mL) at room temperature, trimethylaluminum (2.0 M in hexane, 0.96 mL, 1.92 mmol) was added dropwise. The reaction mixture was stirred for 15 min. A solution of ethyl 3-(3-cyanophenyl)-2-fluoro-3-methylacrylate (0.149 g, 0.639 mmol) in CH2Cl2 (5 mL) was added. It was stirred overnight. 1N HCl was added to neutralize the solution to pH 2–3. Water and CH2Cl2 were added. Organic phase was separated, dried over Na2SO4, concentrated in vacuo to give a solid (0.290 g, yield: 92%), which was pure enough to be used in the next reaction. MS 436 (M+H-$^t$Bu) and 514 (M+Na).

C. Preparation of (2E)-N-{4-[(2-aminosulfonyl)phenyl]phenyl}-3-(3-amidinophenyl)-2-fluoro-3-methylacrylamide, and (2Z)-N-{4-[(2-aminosulfonyl)phenyl]phenyl}-3-(3-amidinophenyl)-2-fluoro-3-methylacrylamide.

To a solution of compound N-{4-[(2-tert-butylaminosulfonyl)phenyl]phenyl}-3-(3-cyanophenyl)-2-fluoro-3-methylacrylamide (0.200 g, 0.406 mmol) in anhydrous MeOH cooled in ice bath, hydrogen chloride gas was bubbled to saturation. The solution was then stirred at room temperature overnight. It was concentrated in vacuo, the residue was dissolved in anhydrous MeOH (6 mL). To the solution, NH4OAc (0.216 g, 2.80 mmol) was added. The mixture was stirred at room temperature overnight. It was concentrated in vacuo. The residue was purified by HPLC using a gradient of 5% CH3CN in H2O (containing 0.1% TFA) to 95% CH3CN over 80 min. Fractions containing the E-isomer product were pooled, and lyophilized to give a powder (90 mg, yield: 49%). Fractions containing the Z-isomer product gave rise to a powder (8 mg, 4%). Fractions containing the E-isomer of hydrolyzed amide product gave rise to a powder (10 mg, 5%). For E-amidine compound, MS 453 (M+H). $^1$H NMR (CD3OD) 8.06 (d, 1H, J=8 Hz), 7.74–7.54 (m, 5H), 7.52–7.46 (m, 3H), 7.35 (d, 2H, J=8 Hz), 7.28 (d, 1H, J=8 Hz), 2.22 (d, 3H, J=3 Hz). For Z-amidine compound, MS 453 (M+H). $^1$H NMR (CD3OD) 8.10 (d, 1H, J=8 Hz), 7.90–7.75 (m, 2H), 7.75–7.56 (m, 5H), 7.56–7.47 (m, 1H), 7.43 (d, 2H, J=8 Hz), 7.34 (d, 1H, J=8 Hz), 2.55 (d, 3H, J=3 Hz). For E-amide compound, MS 454 (M+H) and 476 (M+Na). $^1$H NMR (CD3OD) 8.08 (d, 1H, J=8 Hz), 7.85–7.78 (m, 2H), 7.60 (t, 1H, J=6 Hz), 7.54–7.40 (m, 5H), 7.34 (d, 2H, J=8 Hz), 7.29 (d, 1H, J=8 Hz), 2.20 (d, 3H, J=4 Hz).

Example 6

Preparation of (2E)-N-{4-[(2-aminosulfonyl)phenyl]phenyl}-3-[3-(N-hydroxyamidinophenyl)]-2-fluoro-3-methylacrylamide.

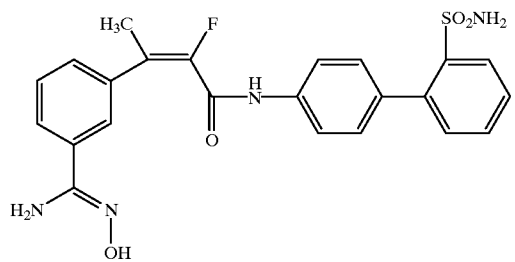

To a solution of compound N-{4-[(2-tert-butylaminosulfonyl)phenyl]phenyl}-3-(3-cyanophenyl)-2-fluoro-3-methylacrylamide (29 mg, 58 mol) in anhydrous MeOH (3 mL) cooled in ice bath, hydrogen chloride gas was bubbled to saturation. The solution was then stirred at room temperature overnight. It was concentrated in vacuo, the residue was dissolved in anhydrous MeOH (2 mL). To the solution, triethylamine (40 L, 287 mol) was added, followed by addition of hydroxyamine hydrochloride (12 mg, 173 mol). The mixture was stirred at room temperature overnight. It was concentrated in vacuo. The residue was purified by HPLC using a gradient of 5% CH3CN in H2O (containing 0.1% TFA) to 90% CH3CN over 80 min. Fractions containing the E-isomer product were pooled, and lyophilized to give a powder (14 mg, yield: 51%). MS 469 (M+H) and 491 (M+Na). $^1$H NMR (CD3OD) 8.07 (d, 1H, J=8 Hz), 7.67–7.55 (m, 5H), 7.55–7.48 (m, 3H), 7.36 (d, 2H, J=8 Hz), 7.30 (d, 1H, J=8 Hz), 2.22 (d, 3H, J=4 Hz).

Example 7

Preparation of (2E)-N-(4-isopropoxyphenyl)-3-(3-amidinophenyl)-2-fluoro-3-methylacrylamide.

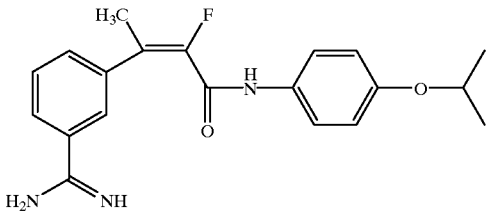

A. Preparation of N-(4-isopropoxyphenyl)-3-(3-cyanophenyl)-2-fluoro-3-methylacrylamide.

To the solution of 4-isopropoxylaniline (117 mg, 0.775 mmol) in CH2Cl2 (8 mL) at room temperature, trimethylaluminum (2.0 M in hexane, 1.20 mL, 2.40 mmol) was added dropwise. The reaction mixture was stirred for 15 min. A solution of ethyl 3-(3-cyanophenyl)-2-fluoro-3-methylacrylate (0.149 g, 0.639 mmol) in CH2Cl2 (5 mL) was added. It was stirred overnight. 1N HCl was added to neutralize the solution to pH 2–3. Water and CH2Cl2 were added. Organic phase was separated, dried over Na2SO4, concentrated in vacuo to give a solid (190 mg, yield: 76%), which was pure enough to be used in the next reaction. MS 339 (M+H) and 361 (M+Na).

B. Preparation of (2E)-N-(4-isopropoxyphenyl)-3-(3-amidinophenyl)-2-fluoro-3-methylacrylamide.

To a solution of compound N-(4-isopropoxyphenyl)-3-(3-cyanophenyl)-2-fluoro-3-methylacrylamide (184 mg, 0.544 mmol) in anhydrous MeOH (4 mL) and CHCl3 (1 mL) cooled in ice bath, hydrogen chloride gas was bubbled to saturation. The solution was then stirred at room temperature overnight. It was concentrated in vacuo, the residue was dissolved in anhydrous MeOH (5 mL). To the solution, NH4OAc (293 mg, 3.80 mmol) was added. The mixture was stirred at room temperature overnight. It was concentrated in vacuo. The residue was purified by HPLC using a gradient of 5% CH3CN in H2O (containing 0.1% TFA) to 95% CH3CN over 65 min. Fractions containing the E-isomer product were pooled, and lyophilized to give a powder (87 mg, yield: 45%). MS 356 (M+H) and 711 (2M+H). $^1$H NMR (CD3OD) 7.72–7.54 (m, 4H), 7.30 (d, 2H, J=8 Hz), 6.80 (d, 2H, J=8 Hz), 4.50 (p, 1H, J=6 Hz), 2.18 (d, 3H, J=4 Hz), 1.24 (d, 6H, J=6 Hz).

Example 8
Preparation of (2E)-N-{4-[(2-aminosulfonyl)phenyl]phenyl}-3-(3-amidino-4-fluorophenyl)-2-fluoro-3-methylacrylamide.

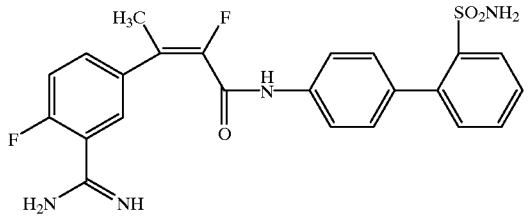

A. Preparation of 3-cyano-4-fluoroacetophenone.

A solution of 3-bromo-4-fluoroacetophenone (1.09 g, 5.00 mmol) and copper(I) cyanide (0.90 g, 10.0 mmol) in anhydrous DMF (15 mL) was heated at 120 C overnight. Water and EtOAc were added. The solution was filtered. Organic phase was separated, washed with sat. NaCl, dried over Na2SO4, concentrated in vacuo to give an oil, which was purified by a silica gel column using a gradient of 0–20% EtOAc in hexane as solvents, to give the titled compound (0.242 g, yield: 30%). MS 164 (M+H).

B: Preparation of ethyl 3-(3-cyano-4-fluorophenyl)-2-fluoro-3-methylacrylate.

To a solution of triethyl 2-fluoro-2-phosphonoacetate (0.294 mL, 1.45 mmol) in anhydrous THF (10 mL) at −78 C, potassium bis(trimethylsilyl)amide (0.5 M in toluene, 3.5 mL, 1.75 mmol) was added dropwise. After 10 min following the addition, a solution of 3-cyano-4-fluoroacetophenone (0.236 g, 1.45 mmol) in THF (5 mL) was added dropwise. The reaction mixture was stirred at −78 C for 30 min, then removed to room temperature, and stirred at the temperature overnight. Aqueous NH4Cl and EtOAc were added. Organic phase was separated, washed with sat. NaCl, dried over Na2SO4, concentrated in vacuo to give an oil as a mixture of E- and Z-isomers in a ratio of 5:1 (0.360 g, yield: 99%), which was pure enough to be used in the next reaction. MS 252 (M+H).

C. Preparation of N-{4-[(2-tert-butylaminosulfonyl)phenyl]phenyl}-3-(3-cyano-4-fluorophenyl)-2-fluoro-3-methylacrylamide.

To the solution of 4-(2'-tert-butylaminosulfonylphenyl)aniline (0.424 g, 1.39 mmol) in CH2Cl2 (15 mL) at room temperature, trimethylaluminum (2.0 M in hexane, 2.10 mL, 4.20 mmol) was added dropwise. The reaction mixture was stirred for 15 min. A solution of ethyl 3-(3-cyano-4-fluorophenyl)-2-fluoro-3-methylacrylate (0.350 g, 1.39 mmol) in CH2Cl2 (8 mL) was added. It was stirred overnight. 1N HCl was added to neutralize the solution to pH 2–3. Water and CH2Cl2 were added. Organic phase was separated, dried over Na2SO4, concentrated in vacuo to give a solid (0.610 g, yield: 86%), which was pure enough to be used in the next reaction. MS 454 (M+H-$^t$Bu) and 532 (M+Na).

D. Preparation of (2E)-N-{4-[(2-aminosulfonyl)phenyl]phenyl}-3-(3-amidino-4-fluorophenyl)-2-fluoro-3-methylacrylamide.

To a solution of compound N-{4-[(2-tert-butylaminosulfonyl)phenyl]phenyl}-3-(3-cyano-4-fluorophenyl)-2-fluoro-3-methylacrylamide (97 mg, 0.19 mmol) in anhydrous MeOH (3 mL) cooled in ice bath, hydrogen chloride gas was bubbled to saturation. The solution was then stirred at room temperature overnight. It was concentrated in vacuo, the residue was dissolved in anhydrous MeOH (5 mL). To the solution, NH4OAc (103 mg, 1.34 mmol) was added. The mixture was stirred at room temperature overnight. It was concentrated in vacuo. The residue was purified by HPLC using a gradient of 5% CH3CN in H2O (containing 0.1% TFA) to 95% CH3CN over 75 min. Fractions containing the E-isomer product were pooled, and lyophilized to give a powder (36 mg, yield: 40%). MS 471 (M+H). $^1$H NMR (CD3OD) 8.06 (d, 1H, J=8 Hz), 7.60–7.48 (m, 7H), 7.36 (d, 2H, J=8 Hz), 7.29 (d, 1H, J=8 Hz), 2.20 (d, 3H, J=4 Hz).

Example 9
Preparation of (2E)-N-{4-[(2-aminosulfonyl)phenyl]phenyl}-3-(3-aminoindazol-5-yl)-2-fluoro-3-methylacrylamide.

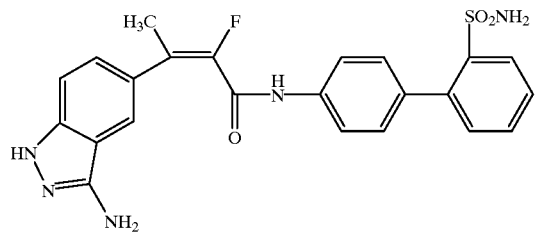

To a solution of N-{4-[(2-tert-butylaminosulfonyl)phenyl]phenyl}-3-(3-cyano-4-fluorophenyl)-2-fluoro-3-methylacrylamide (107 mg, 0.210 mmol) in anhydrous EtOH (7 mL), hydrazine hydrate (91 L, 1.87 mmol) was added. The suspension was heated to reflux overnight, during which time the solution became clear. More hydrazine hydrate (60 L, 1.23 mmol) was added. The mixture was continually heated at reflux for another day. Water and EtOAc were added. Organic phase was separated, dried over Na2SO4, concentrated in vacuo to give a solid.

The solid residue was then dissolved in trifluoroacetic acid (5 mL). It was allowed to stand at room temperature overnight. Trifluoroacetic acid was removed in vacuo. The residue was purified by HPLC using a gradient of 5% CH3CN in H2O (containing 0.1% TFA) to 95% CH3CN over 75 min. Fractions containing the E-isomer product were pooled, and lyophilized to give a powder (44 mg, yield: 45%). MS 522 (M+H) and 544 (M+Na). $^1$H NMR (CD3OD) 8.06 (d, 1H, J=8 Hz), 7.82 (s, 1H), 7.60–7.52 (m, 2H), 7.52–7.45 (m, 3H), 7.39 (d, 1H, J=8 Hz), 7.31 (d, 2H, J=8 Hz), 7.26 (d, 1H, J=8 Hz), 2.22 (d, 3H, J=4 Hz).

Example 10
Preparation of (2E)-N-{4-[(2-aminosulfonyl)phenyl]phenyl}-3-(4-aminoquinazolin-6-yl)-2-fluoro-3-methylacrylamide.

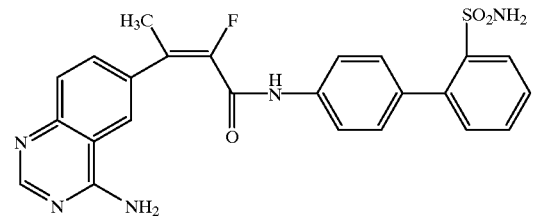

A solution of N-{4-[(2-tert-butylaminosulfonyl)phenyl]phenyl}-3-(3-cyano-4-fluorophenyl)-2-fluoro-3-methylacrylamide (56 mg, 0.11 mmol) and formamidine acetate (68 mg, 0.65 mmol) in anhydrous dimethylacetamide (3 mL) was heated at 160 C overnight. The solvent was removed in vacuo. The residue was then dissolved in trifluoroacetic acid (4 mL). It was allowed to stand at room temperature overnight. Trifluoroacetic acid was removed in vacuo. The residue was purified by HPLC using a gradient of 5% CH3CN in H2O (containing 0.1% TFA) to 95% CH3CN over 70 min. Fractions containing E and Z-isomers (ratio 3:5) were pooled, and lyophilized to give a powder (8 mg, yield: 15%). MS 478 (M+H).

Example 11

Preparation of (2E)-N-{4-[(2-aminosulfonyl)phenyl]-2-fluorophenyl}-3-(1-aminoisoquinol-7-yl)-2-fluoro-3-methylacrylamide.

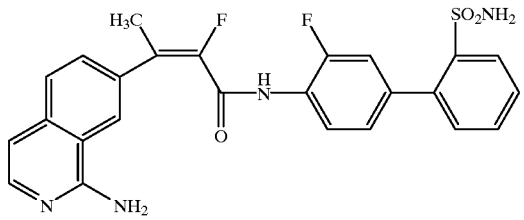

A. Preparation of 7-acetyl-isoquinoline.

A solution of a mixture of 7-bromo and 5-bromo-isoquinoline (in a ratio of 6:4, prepared according to Tyson in J. Am. Chem. Soc. 1939, 61, 183–185) (5.00 g, 24.0 mmol) and tributyl(ethoxyvinyl) tin (8.68 g, 24.0 mmol) in toluene (200 mL) was degassed with a stream of argon for 10 min. Then, Pd(Ph3P)4 (1.00 g, 0.87 mmol) was added. The solution was heated to reflux overnight. It was cooled down, filtered. The filtrate was washed with water, sat. NaCl, dried over Na2SO4, concentrated in vacuo to give an oil.

The oil was dissolved in THF (100 mL), 2N aq. HCl (45 mL) was added. The solution was stirred at room temperature overnight. Water and EtOAc were added. The aqueous phase was separated, neutralized to pH 7–8 with 5M aq. NaOH. The product was extracted with EtOAc. The EtOAc extract was dried over Na2SO4, concentrated in vacuo. The residue was purified by a silica gel column using a gradient of 30% to 50% EtOAc in hexane as solvents. The fractions containing pure 7-bromo-isoquinoline were pooled, and concentrated in vacuo to give a solid (1.46 g). $^1$H NMR (CDCl3) 9.39 (s, 1H), 8.63 (d, 1H, J=4 Hz), 8.60 (s, 1H), 8.27 (d, 1H, J=7 Hz), 7.90 (d, 1H, J=7 Hz), 7.72 (d, 1H, J=4 Hz), 2.74 (s, 3H).

B: Preparation of (2E) ethyl 3-(isoquinolin-7-yl)-2-fluoro-3-methylacrylate.

To a solution of triethyl 2-fluoro-2-phosphonoacetate (1.19 mL, 5.86 mmol) in anhydrous THF (20 mL) at −78 C, potassium bis(trimethylsilyl)amide (0.5 M in toluene, 14 mL, 7.0 mmol) was added dropwise. After 30 min following the addition, a solution of 7-acetyl-isoquinoline (0.500 g, 2.92 mmol) in THF (7 mL) was added dropwise. The reaction mixture was stirred at −78 C for 30 min, then removed to room temperature, and stirred at the temperature overnight. Aqueous NH4Cl and EtOAc were added. Organic phase was separated, washed with sat. NaCl, dried over Na2SO4, concentrated in vacuo to give an oil, which was purified by a silica gel column using a gradient of 20% to 40% EtOAc in hexane as solvents. The fractions containing the E-isomer product were pooled, and concentrated in vacuo to give an oil (0.460 g, yield: 61%). MS 260 (M+H).

C. Preparation of (2E) N-{4-[(2-tert-butylaminosulfonyl)phenyl]-2-fluorophenyl}-3-(isoquinolin-7-yl)-2-fluoro-3-methylacrylamide.

To the solution of 4-(2'-tert-butylaminosulfonylphenyl)-2-fluoroaniline (166 mg, 0.516 mmol) in CH2Cl2 (6 mL) at room temperature, trimethylaluminum (2.0 M in hexane, 0.77 mL, 1.54 mmol) was added dropwise. The reaction mixture was stirred for 15 min. A solution of (2E) ethyl 3-(isoquinolin-7-yl)-2-fluoro-3-methylacrylate (119 mg, 0.459 mmol) in CH2Cl2 (5 mL) was added. It was stirred at room temperature for 2 hours. 1N HCl was added to neutralize the solution to pH 5–6. Water and CH2Cl2 were added. Organic phase was separated, dried over Na2SO4, concentrated in vacuo to give a solid, which was purified by a silica gel column using a gradient of 30% to 50% EtOAc in hexane as solvents. The fractions containing the product were pooled, and concentrated in vacuo to give solid (150 mg, yield: 61%). MS 536 (M+H).

D. Preparation of (2E)-N-{4-[(2-aminosulfonyl)phenyl]-2-fluorophenyl}-3-(1-aminoisoquinol-7-yl)-2-fluoro-3-methylacrylamide.

To a solution of (2E) N-{4-[(2-tert-butylaminosulfonyl)phenyl]-2-fluorophenyl}-3-(isoquinolin-7-yl)-2-fluoro-3-methylacrylamide (140 mg, 0.262 mmol) in acetone (6 mL) at room temperature, m-chloroperbenzoic acid (85 mg, ~70%, 0.345 mmol) was added. The mixture was stirred at room temperature overnight. The solvent was removed in vacuo. The residue was partitioned between EtOAc and sat. NaHCO3. The organic phase was separated, dried over Na2SO4, concentrated in vacuo to give a solid.

The solid was dissolved in anhydrous pyridine (4 mL). To the solution, toluenesulfonyl chloride (62 mg, 0.325 mmol) was added. It was stirred at room temperature for 5 min. The solvent was removed in vacuo to give an oil.

The oil was dissolved in ethanolamine (5 mL). The solution was stirred at room temperature for 3 hours. Water and EtOAc were added. The organic phase was separated. The aqueous phase was extracted with EtOAc twice. The combined organic phases were dried over Na2SO4, concentrated in vacuo to give an oil.

The oil was dissolved in TFA (10 mL). The solution was allowed to stand at room temperature overnight. TFA was removed in vacuo. The residue was purified by HPLC using a gradient of 5% CH3CN in H2O (containing 0.1% TFA) to 95% CH3CN over 65 min. Fractions containing the product were pooled, and lyophilized to give a powder (40 mg, yield: 31%). MS 495 (M+H). $^1$H NMR(CD3OD) 8.38 (s, 1H), 8.07 (d, 1H, J=8 Hz), 7.88 (s, 2H), 7.60–7.48 (m, 4H), 7.28 (d, 1H, J=8 Hz), 7.21 (t, 2H, J=8 Hz), 7.14 (d, 1H, J=8 Hz), 2.29 (d, 3H, J=4 Hz).

Example 12

Preparation of (2E)-N-{5-[(2-aminosulfonyl)phenyl]-pyridin-2yl}-3-(1-aminoisoquinol-7-yl)-2-fluoro-3-methylacrylamide.

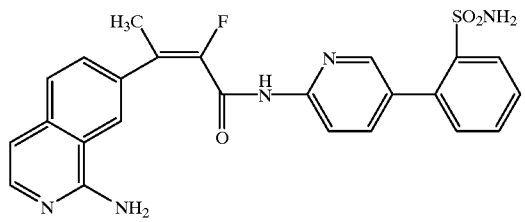

A. Preparation of (2E) 3-(isoquinolin-7-yl)-2-fluoro-3-methylacrylic acid.

A solution of (2E) ethyl 3-(isoquinolin-7-yl)-2-fluoro-3-methylacrylate (210 mg, 0.811 mmol) in MeOH and 1N NaOH (5 mL) was stirred at room temperature for 3 hours. The solution was neutralized with acetic acid. The product was extracted with EtOAc three times. The combined organic phases were dried over Na2SO4, concentrated in vacuo to give a solid (124 mg, yield: 66%). The material is pure enough for the next reaction.

B. Preparation of (2E) N-{5-[(2-tert-butylaminosulfonyl)phenyl]-pyridin-2yl}-3-(isoquinolin-7-yl)-2-fluoro-3-methylacrylamide.

To a solution of (2E) 3-(isoquinolin-7-yl)-2-fluoro-3-methylacrylic acid (119 mg, 0.515 mmol), 2-amino-5-[(2-tert-butylaminosulfonyl)phenyl]-pyridine (254 mg, 0.833 mmol) and dimethylaminopyridine (104 mg, 0.852 mmol) in anhydrous pyridine (4 mL) at 0 C, POCl3 (78 L, 0.837 mmol) was added dropwise. It was then stirred at room temperature overnight. Water and EtOAc were added. The organic phase was separated, dried over Na2SO4, concentrated in vacuo. The residue was purified by a silica gel column using a gradient of 40% to 60% EtOAc in hexane as solvents, to give the titled compound (80 mg, yield: 30%). MS 519 (M+H).

C. Preparation of (2E)-N-{5-[(2-aminosulfonyl)phenyl]-pyridin-2yl}-3-(1-aminoisoquinol-7-yl)-2-fluoro-3-methylacrylamide.

To a solution of (2E) N-{5-[(2-tert-butylaminosulfonyl)phenyl]-pyridin-2yl}-3-(isoquinolin-7-yl)-2-fluoro-3-methylacrylamide (77 mg, 0.15 mmol) in acetone (5 mL) at room temperature, m-chloroperbenzoic acid (42 mg, ~70%, 0.17 mmol) was added. The mixture was stirred at room temperature overnight. The solvent was removed in vacuo. The residue was partitioned between EtOAc and sat. NaHCO3. The organic phase was separated, dried over Na2SO4, concentrated in vacuo to give a solid.

The solid was dissolved in anhydrous pyridine (3 mL). To the solution, toluenesulfonyl chloride (36 mg, 0.19 mmol) was added. It was stirred at room temperature for 5 min. The solvent was removed in vacuo to give an oil.

The oil was dissolved in ethanolamine (5 mL). The solution was stirred at room temperature overnight. Water and EtOAc were added. The organic phase was separated. The aqueous phase was extracted with EtOAc twice. The combined organic phases were dried over Na2SO4, concentrated in vacuo to give an oil.

The oil was dissolved in TFA (4 mL). The solution was allowed to stand at room temperature overnight. TFA was removed in vacuo. The residue was purified by HPLC using a gradient of 5% CH3CN in H2O (containing 0.1% TFA) to 95% CH3CN over 70 min. Fractions containing the product were pooled, and lyophilized to give a powder (14 mg, yield: 20%). MS 478 (M+H). $^1$HNMR (CD3OD) 8.40 (s, 1H), 8.31 (s, 1H), 8.10 (d, 1H, J=8 Hz), 7.95–7.86 (m, 3H), 7.80 (d, 1H, J=8 Hz), 7.66–7.53 (m, 3H), 7.33 (d, 1H, J=8 Hz), 7.25 (d=1H, J=8 Hz), 2.30 (d, 3H, J=4 Hz).

Example 13

Preparation of (2E)-N-{4-[(2-aminosulfonyl)phenyl]-2-chlorophenyl}-3-(1-aminoisoquinol-7-yl)-2-fluoro-3-methylacrylamide.

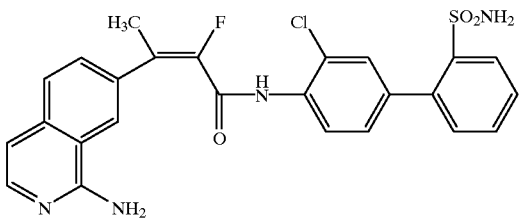

The compound was prepared by analogous procedures as described previously for compound (2E)-N-{4-[(2-aminosulfonyl)phenyl]-2-fluorophenyl}-3-(1-aminoisoquinol-7-yl)-2-fluoro-3-methylacrylamide in Example 11, except that 4-(2'-tert-butylaminosulfonylphenyl)-2-chloroaniline was used in the place of 4-(2'-tert-butylaminosulfonylphenyl)-2-fluoroaniline. MS 511 and 513 (M+H). $^1$H NMR (CD3OD) 8.39 (s, 1H), 8.06 (d, 1H, J=8 Hz), 7.90 (s, 2H), 7.64 (d, 1H, J=8 Hz), 7.60–7.47 (m, 4H), 7.27 (t, 2H, J=8 Hz), 7.20 (d, 1H, J=8 Hz), 2.30 (d, 3H, J=4 Hz).

Example 14

Preparation of (2E)-N-{4-[(2-aminosulfonyl)phenyl]phenyl}-3-(1-aminoisoquinol-7-yl)-2-fluoro-3-methylacrylamide.

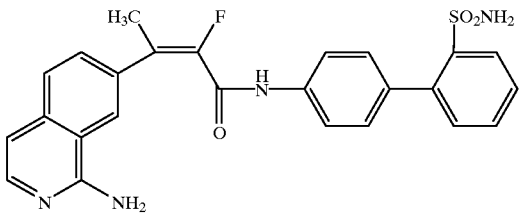

The compound was prepared by analogous procedures as described previously for compound (2E)-N-{4-[(2-aminosulfonyl)phenyl]-2-fluorophenyl}-3-(1-aminoisoquinol-7-yl)-2-fluoro-3-methylacrylamide in Example 11, except that 4-(2'-tert-butylaminosulfonylphenyl)aniline was used in the place of 4-(2'-tert-butylaminosulfonylphenyl)-2-fluoroaniline. MS 477 (M+H) and 499 (M+Na). $^1$H NMR (CD3OD) 8.38 (s, 1H), 8.06 (d, 1H, J=8 Hz), 7.90 (s, 2H), 7.60–7.45 (m, 5H), 7.33 (d, 2H, J=8 Hz), 7.27 (d, 1H, J=8 Hz), 7.21 (d, 1H, J=8 Hz), 2.27 (d, 3H, J=4 Hz).

Example 15

(2Z)-N-{4-[(2-aminosulfonyl)phenyl]phenyl}-3-(3-amidinophenyl)-2-methylacrylamide

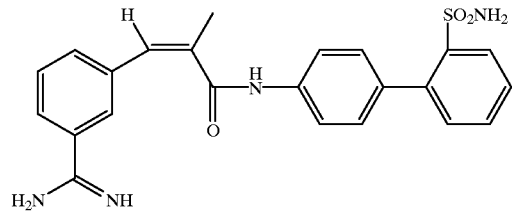

Part A. Ethyl (Z)-3-(3-cyanophenyl)-2-methyl-2-butenoate

A solution of 1.00 g (3.0 mmol) of ethyl 2-[bis(2,2,2-trifluoroethyl)phosphono]-propionate (*Synth. Comm.*, 1991, 21, 2391) and 3.9 g (5 eq) of 18-crown-6 in 25 mL of anhydrous THF was cooled with a dry ice-acetone bath, and 7.0 mL of a 0.5 M solution of potassium bis(trimethylsilyl) amide in toluene were added. The solution was stirred in the cold for 20 min, then a solution of 400 mg (3.05 mmol) of 3-cyanobenzaldehyde in 10 of anhydrous THF was added dropwise over a few minutes. The reaction was stirred in the cold for 1 hr, then allowed to warm to room temperature over 3 hr, quenched by the addition of 10 mL of saturated aqueous ammonium chloride, and extracted with 2×50 mL of ether. The organic layer was washed with 50 mL of water, followed by 50 mL of saturated NaCl, then dried over $MgSO_4$. Filtration and concentration gave 1 g of a light yellow oil, which was washed through a plug of silica gel with 200 mL of $CH_2Cl_2$. Concentration then gave 586 mg (97%) of the desired product as a light yellow oil, which was >90% the desired (Z)-isomer by $^1H$ NMR.

Part B. (2Z)-N-[4-(2{[(N-1,1-dimethylethyl)amino]sulfonyl}phenyl)phenyl]-3-(3-cyanophenyl)-2-methylacrylamide To a solution of 103 mg (0.34 mmol) of 4'-amino-N-(1,1-dimethylethyl)-[1,1'-biphenyl]-2-sulfonamide in 5 mL of anhydrous $CH_2Cl_2$ was added 0.5 mL of a 2.0 M solution of trimethylaluminum in hexanes, and the solution was stirred at room temperature for 30 minutes. A solution of 103 mg of ethyl (Z)-3-(3-cyanophenyl)-2-methyl-2-butenoate in 5 mL of anhydrous $CH_2Cl_2$ was then added dropwise over a few minutes, and the reaction was stirred at room temperature overnight. The reaction was then carefully quenched by the addition of 10 mL of 1N HCl, and the reaction mixture was then partitioned between 100 mL of $CH_2Cl_2$ and 50 mL of $H_2O$. The organic layer was dried over $MgSO_4$, filtered and concentrated to give a solid residue, which was subjected to flash column chromatography on silica gel using 10% EtOAc in hexanes to give 104 mg (65%) of the desired product as a white solid.

Part C. (2Z)-N-{4-[(2-aminosulfonyl)phenyl]phenyl}-3-(3-amidinophenyl)-2-methylacrylamide A suspension of 50 mg of the above nitrile in 10 mL of anhydrous methanol was cooled with an ice-water bath, and HCl gas was bubbled into the solution at a moderate rate for 10 min. The reaction was then closed with a rubber septum and stirred at room temperature overnight. The reaction was concentrated to give a semisolid residue, which was taken up in 5 mL of anhydrous methanol, and 41 mg of vacuum dried ammonium acetate were added. The solution was heated at gentle reflux for 1.5 hr, then concentrated to give a white solid. Preparative HPLC (gradient elution with water:acetonitrile each containing 0.1% TFA on C18) then afforded 44 mg of the desired product as a white solid.

Part D. (2Z)-N-{4-[(2-aminosulfonyl)phenyl]phenyl}-3-(3-amidinophenyl)-2-methylpropanamide A solution of 14 mg of the alkene from Part C and 5 drops of triethylamine in 5 mL of methanol, together with 10 mg of 10% Pd/C was placed under a balloon of hydrogen and stirred overnight. The reaction was filtered and concentrated, and the residue was subjected to preparative HPLC (gradient elution with water:acetonitrile each containing 0.1% TFA on C18) to give 7 mg of the desired product as a white solid.

Example 16
(2E)-N-{4-[(2-aminosulfonyl)phenyl]phenyl}-3-(3-amidinophenyl)-2-methylacrylamide.

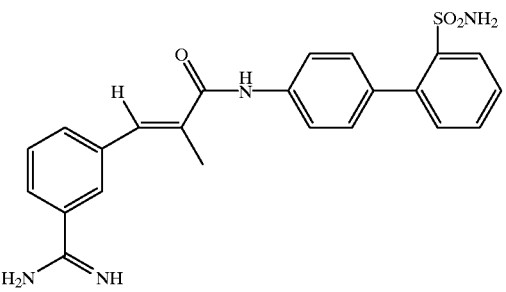

Part A. Ethyl (Z)-3-(3-cyanophenyl)-2-methyl-2-butenoate

A solution of 900 Mg (3.8 mmol) of triethyl 2-phosphonopropionate in 25 mL of anhydrous THF was cooled with a dry ice-acetone bath, and 8.0 mL of a 0.5 M solution of potassium bis(trimethylsilyl)amide in toluene were added dropwise. The solution was stirred in the cold for 20 min, then a solution of 500 mg (3.78 mmol) of 3-cyanobenzaldehyde in 10 of anhydrous THF was added dropwise over a few minutes. The reaction was stirred in the cold for 1 hr, then allowed to warm to room temperature over 1 hr. The reaction was quenched by the addition of 10 mL of saturated aqueous ammonium chloride, and extracted with 2×100 mL of ether. The organic layer was washed with 50 mL of saturated NaCl, then dried over $MgSO_4$. Filtration and concentration gave 1 g of a light yellow oil, which was washed through a plug of silica gel with 200 mL of $CH_2Cl_2$. Concentration then gave 730 mg (96%) of the desired product as a light yellow oil, which was exclusively the desired (E)-isomer by $^1H$ NMR.

Part B. (2E)-N-[4-(2{[(N-1,1-dimethylethyl)amino]sulfonyl}phenyl)phenyl]-3-(3-cyanophenyl)-2-methylacrylamide To a solution of 76 mg (0.29 mmol) of 4'-amino-N-(1,1-dimethylethyl)-[1,1'-biphenyl]-2-sulfonamide in 5 mL of anhydrous $CH_2Cl_2$ was added 0.4 mL of a 2.0 M solution of trimethylaluminum in hexanes, and the solution was stirred at room temperature for 20 minutes. A solution of 59 mg of ethyl (E)-3-(3-cyanophenyl)-2-methyl-2-butenoate in 5 mL of anhydrous $CH_2Cl_2$ was then added dropwise over a few minutes, and the reaction was stirred at room temperature overnight. The reaction was then carefully quenched by the addition of 10 mL of 1N $NH_4Cl$, and the reaction mixture was then partitioned between 100 mL of $CH_2Cl_2$ and 50 mL of $H_2O$. The organic layer was dried over MgSO4, filtered and concentrated to give a light yellow solid, which was subjected to flash column chromatography on silica gel using first 5%, and then 10% EtOAc in $CH_2Cl_2$ to give 98 mg (83%) of the desired product as a white solid.

Part C. (2E)-N-{4-[(2-aminosulfonyl)phenyl]phenyl}-3-(3-amidinophenyl)-2-methylacrylamide A suspension of 98 mg of the nitrile from Part B in 10 mL of ethyl acetate was treated with 100 L of anhydrous methanol, cooled with an ice-methanol bath, and HCl gas was bubbled into the solution at a moderate rate for 10 min. The reaction was then closed with a rubber septum and stirred at room temperature overnight. The reaction was concentrated to give a yellow solid, which was taken up in 5 mL of anhydrous methanol, and 80 mg of vacuum dried ammonium acetate were added. The solution was heated at gentle reflux for 1.5 hr, then concentrated to give a yellow oil. This oil was taken up in 5 mL of TFA and stirred at room temperature overnight to complete the removal of the t-butyl group. Preparative HPLC (gradient elution with water:acetonitrile each containing 0.1% TFA on C18) then afforded 66 mg of the desired product as a white solid.

Example 17
(2Z)-N-{4-[(2-aminosulfonyl)phenyl]phenyl}-3-(1-aminoisoquinolin-7-yl)-acrylamide

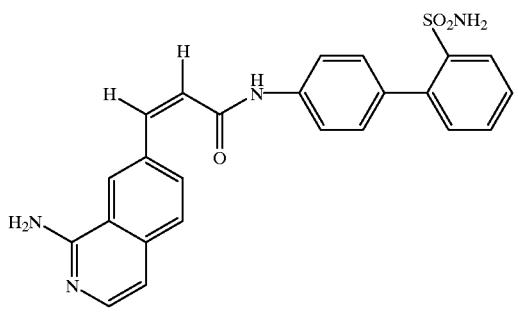

Part A. 7-Bromoisoquinoline

This compound was prepared as a 60:40 mixture with 5-bromoisoquinoline as in *J. Am. Chem. Soc.*, 1939, 61, 183.

Part B. 7-Bromoisoquinoline N-oxide hydrochloride

This compound was prepared by a procedure analogous to that for 6-bromoisoquinoline N-oxide hydrochloride as in PCT WO 98/47876. A solution of 7.8 g (37.5 mmol) of a 60:40 mixture of 7-bromo and 5-bromoisoquinoline in 125 mL of $CH_2Cl_2$ was treated portionwise with 9.7 g (39.4 mmol) of 3-chloroperoxybenzoic acid (~70% purity). The solution, which was initially homogeneous, deposited a voluminous precipitate over 1 hr. Then 100 mL of methanol were added, and the reaction was concentrated to a volume of about 100 mL. Gaseous HCl was then bubbled through the solution for about 10 min, during which time the solution became warm and all of the precipitate dissolved. A few minutes later, another voluminous precipitate began to form. To this solution was added 100 mL of ether, and the mixture was stirred in an ice-water bath for 20 minutes. The resulting product was isolated by filtration, washed thoroughly with ether, and air-dried to give 8.07 g (83%) of the desired compound as a white solid, which was still a 60:40 mixture of the 7- and 5-bromo isomers.

Part C. 7-Bromo-1-chloroisoquinoline

This compound was prepared by a procedure analogous to that for 6-bromo-1-chloroisoquinoline as in PCT WO 98/47876. A solution of 8.07 g (31 mmol) of the mixture from Part B was taken up in 50 mL of $POCl_3$, and the mixture was heated at 90° C. for 2 hr. The reaction mixture was concentrated to remove most of the $POCl_3$, and the residue was taken up in 100 mL of $CH_2Cl_2$. The solution was carefully basified to pH 10 by the slow addition of 1N NaOH, and the organic layer was washed with 100 mL of $H_2O$, 100 mL of sat. NaCl, and dried over $MgSO_4$. Filtration and concentration gave a light yellow solid, which was subjected to flash column chromatography on silica gel first with 5% and then with 10% EtOAc in hexanes. A total of 3.62 g (48%) of the desired 7-bromo-1-chloroisoquinoline was isolated from this chromatography free of the 5-bromo isomer.

Part D. 7-Bromo-1-phenoxyisoquinoline

A solution of 3.60 g (14.8 mmol) of 7-bromo-1-chloroisoquinoline and 1.5 g of solid KOH in 11.2 g of phenol was heated at 140° C. for 2 hr. The reaction was cooled to room temperature, then partitioned between 100 mL of $CH_2Cl_2$ and 100 mL of 3N NaOH. The organic layer was washed with another 2×100 mL of 3N NaOH, then with 100 mL of $H_2O$, and dried over $MgSO_4$. Filtration and concentration gave a yellow oil, which was subjected to flash column chromatography on silica gel 30% $CH_2Cl_2$ in hexanes, giving 3.42 g (77%) of the desired product as a light yellow solid.

Part E. 1-Amino-7-bromoisoquinoline

A mixture of 3.40 g (11.3 mmol) of 1-amino-7-bromoisoquinoline and 7.65 g of ammonium acetate was heated at 150° C. for 15 hr. The reaction was cooled, and the residue was partitioned between 200 mL of EtOAc and 200 mL of 3N NaOH. The organic layer was extracted with 2×100 mL of 2N HCl, and the combined aqueous extracts were basified to pH 10 using 50% NaOH. This solution was extracted with 2×100 mL of EtOAc, and the organics were then washed with 100 mL of sat. NaCl and dried over MgSO4. Filtration and concentration gave 1.68 g (66%) of the desired amino compound as a yellow solid.

Part F. 1-[Bis(t-butoxycarbonyl)amino]-7-bromoisoquinoline

A solution of 740 mg (3.32 mmol) of 1-amino-7-bromoisoquinoline in 50 mL of acetonitrile was treated with 1.4 mL of N,N-diiospropylethylamine and 100 mg of 4-(N,N-dimethylamino)pyridine, followed by 3.0 g (4.1 eq) of di-t-butyldicarbonate, and the reaction was stirred at 40° C. for 1 hr. By HPLC analysis, there was still some starting amino compound that remained, so another 1.0 g of di-t-butyldicarbonate were added, and the reaction was stirred at 40° C. for another 30 min. The reaction mixture was concentrated to give a dark oil, which was subjected to flash column chromatography on silica gel with 20% EtOAc in hexanes to give 736 mg of the desired product as a light yellow solid. Also isolated were 156 mg of product as a somewhat less pure light yellow solid, making the total yield 64%.

Part G. 1-[Bis(t-butoxycarbonyl)amino]isoquinoline-7-carboxaldehyde

A solution of 400 mg (0.95 mmol) of 1-[bis(t-butoxycarbonyl)amino]-7-bromoisoquinoline in 50 mL of anhydrous THF was cooled with a liquid nitrogen/methanol slush bath (−98° C.), and 0.55 mL of a 2.43 M solution of n-BuLi in hexanes (1.3 eq) was added dropwise over 1 min. The solution was stirred in the cold for 5 min, then a solution of 5 mL of anhydrous DMF in 10 mL of anhydrous THF was added rapidly. The solution was allowed to warm to about 0° C., then poured into 50 mL of 0.5 N HCl, and 50 mL of EtOAc were added. The aqueous layer was brought to pH 6 with 1N NaOH, 25 mL of sat. NaCl were added, and the layers were shaken and separated. The organic layer was dried over $MgSO_4$, filtered, and concentrated to give an oily residue. This residue was subjected to flash column chromatography on silica gel with 20% EtOAc in hexanes to give 190 mg (54%) of the desired aldehyde as a yellow semisolid.

Part H. (2Z)-3-{[1-bis(t-butoxycarbonyl)amino]isoquinolin-7-yl}acrylic acid, 2-(trimethylsilyl)ethyl ester A solution of 117 mg (0.29 mmol) of [bis(2,2,2-trifluoroethoxy)phosphinyl]acetic acid, 2-(trimethylsilyl) ethyl ester (*J. Org. Chem.*, 1991, 56, 4204) and 400 mg of 18-crown-6 in 25 mL of anhydrous THF was cooled with a dry ice-acetone bath under Ar, and 0.75 mL of a 0.5 M solution of potassium bis(trimethylsilyl)amide in toluene were added dropwise over 2 min. The reaction was stirred in the cold for 15 min, then a solution of 100 mg (0.27 mmol) of 1-[bis(t-butoxycarbonyl)amino]isoquinoline-7-carboxaldehyde in 25 mL of anhydrous THF was added dropwise over 10 min. The reaction was then allowed to warm to room temperature overnight, then partitioned between 100 mL of CH₂Cl₂ and 50 mL of H₂O. The organics were washed with aqueous NaCl, and dried over MgSO₄. Filtration and concentration gave an oily residue, which was subjected to flash column chromatography on silica gel with 25% EtOAc in hexanes to give 33 mg of the desired product as a clear, colorless oil.

Part I. (2Z)-N-[4-(2{[(N-1,1-dimethylethyl)amino]sulfonyl}phenyl)phenyl]-3-{[1-bis(t-butoxycarbonyl)amino]isoquinolin-7-yl}acrylamide A solution of 63 mg (0.12 mmol) of (2Z)-3-{[1-bis(t-butoxycarbonyl)amino]isoquinolin-7-yl}acrylic acid, 2-(trimethylsilyl)ethyl ester in 1 mL of DMF was treated at room temperature with 150 L of 1.0 M tetrabutylammonium fluoride in THF overnight. The reaction mixture was directly subjected to preparative HPLC (gradient elution with water:acetonitrile each containing 0.1% TFA on C18) to give, after lyophilization, 21 mg of the desired acid as a white solid. A solution of this acid and 18 mg of 4'-amino-N-(1,1-dimethylethyl)-[1,1'-biphenyl]-2-sulfonamide in 2 mL of anhydrous DMF, together with 40 L of N,N-diisopropylethylamine, was treated at room temperature with 25 mg (1.3 eq) of HATU, and the reaction was stirred at room temperature for 1 hr. The reaction mixture was dissolved in 100 mL of CH₂Cl₂, washed with 2×25 mL of sat. NaHCO₃, and dried over MgSO₄. Filtration and concentration gave 53 mg of the desired product as a yellow oily residue, which was used in the next reaction without further purification.

Part J. (2Z)-N-{4-[(2-aminosulfonyl)phenyl]phenyl}-3-(1-aminoisoquinolin-7-yl)-acrylamide A solution of the yellow oil from Part I in 2 mL of TFA was stirred first in an ice-water bath, and then at room temperature overnight. The reaction mixture was concentrated and directly subjected to preparative HPLC (gradient elution with water:acetonitrile each containing 0.1% TFA on C18) to give 10 mg of the desired product as an off-white solid.

Example 18
(2Z)-N-{4-[(2-aminosulfonyl)phenyl]-2-bromophenyl}-3-(1-aminoisoquinolin-7-yl)-acrylamide

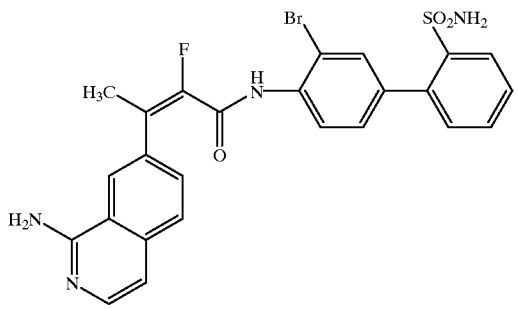

Part A. 2-Bromo-4-iodoaniline

This compound was prepared by a modification of the procedure found in *J. Chem. Soc.* (C), 1970, 2106. A mixture of 1.61 g (9.36 mmol) of 2-bromoaniline and 10 mL of H₂O, together with 750 mg of solid sodium bicarbonate was heated gently with a heat gun to melt the aniline, and 2.58 g (10.2 mmol) of powdered iodine were added portionwise over a few minutes. The reaction mixture was stirred at room temperature for 2 hr. The resulting dark solid was recovered by filtration, washed with H2O, and air-dried to give a dark solid was still slightly wet. Th product was purified directly by flash column chromatography on silica gel first with hexanes, and then with 5% EtOAc in hexanes to give 2.53 g (91%) of the desired iodo compound as a light pink solid.

Part B. 4-(2'-tert-butylaminosulfonylphenyl)-2-bromoaniline

Into a 1 L 4-necked round bottom flask equipped with mechanical stirrer, thermometer, condenser and argon sweep was charged 4-iodo-2-bromoaniline (25 g, 0,084 mol) followed by toluene (250 mL), water (150 mL), n-butanol (50 mL) and solid cesium carbonate (82 g, 0.25 mol, 3.0 eq.). The biphasic solution was purged with argon for several minutes after which time tetrakis(triphenylphosphine)palladium(0) (2.3 g, 0.002 mol) and 2-(t-butylsulfonamido)benzene boronic acid (23.7 g, 0.092 mol, 1.1 eq.) were charged. The solution was heated to 65–70° C. under an argon atmosphere and maintained at this temperature for 3–4 hours until reaction completion was determined by HPLC analysis. The solution was cooled to room temperature and the layers were separated. The aqueous layer was discarded and the organic layer was evaporated under reduced pressure to 100 mL. This organic solution was added in a thin stream to 800 mL of rapidly stirring diisopropyl ether. A tan solid precipitated, which was removed by filtration through celite, and the filter cake was washed with additional diisopropyl ether (2×50 ml). The resulting clear brown filtrate was evaporated to 100 mL and cooled to room temperature, where it was seeded with pure 4-amino-3-bromo-2'-(t-butylsulfonamide)biphenyl, then further cooled to −20° C. and allowed to stand overnight. The resulting off-white crystalline solid was recovered by filtration and washed with cold diisopropyl ether. Drying overnight under high vacuum at room temperature gave 19.9 g (62%) of the biphenyl compound as an off-white solid. HPLC and mass spectral analysis confirmed the product identity.

Part C. (2E)-N-{4-[(2-aminosulfonyl)phenyl]-2-fluorophenyl}-3-(1-aminoisoquinol-7-yl)-2-fluoro-3-methylacrylamide.

The compound was prepared by analogous procedures as described previously for compound (2E)-N-{4-[(2-aminosulfonyl)phenyl]-2-fluorophenyl}-3-(1-aminoisoquinol-7-yl)-2-fluoro-3-methylacrylamide in Example 11, except that 4-(2'-tert-butylaminosulfonylphenyl)-2-bromoaniline was used in place of 4-(2'-tert-butylaminosulfonylphenyl)-2-fluoroaniline.

Example 19
3-((1E)-1-Methyl-2-{N-[4-(2-sulfamoylphenyl)phenyl]carbamoyl}vinyl)benzene-carboxamidine

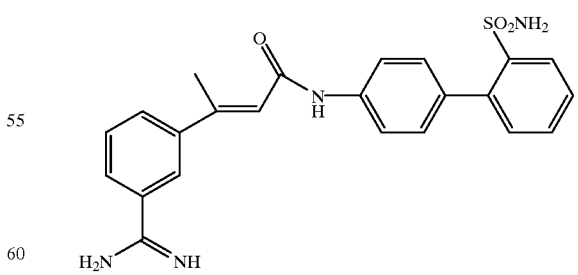

Part A. Ethyl (E)-3-{[(trifluoromethyl)sulfonyl]-oxy}-2-propenoate and) ethyl (Z)-3-{[(trifluoromethyl)-sulfonyl]oxy}-2-propenoate To a solution of ethyl acetoacetate (1.3 g, 10 mmol) in 10 ml anhydrous dichloromethane was added triethylamine (1.46 ml, 10.5 mmol). The reaction was cooled to −78° C. under argon to which trifluoromethanesulfonic anhydride (2.96 g, 10.5 mmol) was added dropwise via syringe over 5 minutes. Reaction was allowed to warm to room temperature and stirred over night. Next morning the reaction was diluted with 25 ml dichloromethane, organic was washed with 2×50 ml water, 2×50 ml 1N HCl, dried over magnesium sulfate, filtered and concentrated. Crude oil was chromatographed on silica gel using 5% EtOAc in hexane as the eluent to give 1) ethyl (E)-3-{[(trifluoromethyl)sulfonyl]-oxy}-2-propenoate (800 mg, 60%) as a clear oil: H$^1$NMR (CDCl$_3$): 1.247–1.282 (t, 3H); 2.471 (s, H); 4.155–4.209 (m, 2H); 5.912 (s, H); and 2) ethyl (Z)-3-{[(trifluoromethyl)sulfonyl]-oxy}-2-propenoate (450 mg, 30%) as a clear oil: H$^1$NMR (CDCl$_3$): 1.247–1.283 (t, 3H); 2.131 (s, 3H); 4.18–4.233 (m, 2H); 5.736 (s, H)

Part B. Ethyl (E) 3-(3-cyanophenyl)-2-propenoate

To a solution of ethyl (E)-3-{[(trifluoromethyl)sulfonyl]-oxy}-2-propenoate (390 mg, 1.49 mmol) in 5 ml anhydrous dioxane was added potassium phosphate (474 mg, 2.24 mmol), 3-cyanophenyl boronic acid (217 mg, 1.49 mmol), and tetrakis (triphenylphosphine)palladium(0) (43 mg, 0.038 mmol). Reaction mixture was heated to reflux and stirred overnight. Mixture was filtered through a pad of Celite, diluted with 50 ml ethyl acetate, washed with 2×50 ml water, 2×50 ml saturated brine solution, dried over magnesium sulfate, filtered and concentrated in vacuo. Residue was chromatographed on silica gel using 5% EtOAc in hexane as the eluent to give ethyl (E) 3-(3-cyanophenyl)-2-propenoate (240 mg, 71%) as a clear yellow oil after drying. H$^1$NMR (CDCl$_3$): 1.2–1.32 (t, 3H); 2.547 (s, 3H); 4.18–4.24 (m, 2H); 6.113 (s, H); 7.47–7.725 (m, 4H). NOE confirmed stereo orientation.

Part C. Ethyl (Z) 3-(3-cyanophenyl)-2-propenoate

To a solution of ethyl (Z)-3-{[(trifluoromethyl)sulfonyl]-oxy}-2-propenoate (330 mg, 1.25 mmol) in 5 ml anhydrous dioxane was added potassium phosphate (398 mg, 1.88 mmol), 3-cyanophenyl boronic acid (185 mg, 1.25 mmol), and tetrakis (triphenylphosphine)palladium(0) (36 mg, 0.031 mmol). Reaction mixture was heated to reflux and stirred overnight. Mixture was filtered through a pad of Celite, diluted with 50 ml ethyl acetate, washed with 2×50 ml water, 2×50 ml saturated brine solution, dried over magnesium sulfate, filtered and concentrated in vacuo. Residue was chromatographed on silica gel using 5% EtOAc in hexane as the eluent to give ethyl (Z) 3-(3-cyanophenyl)-2-propenoate (240 mg, 71%) as a clear oil after drying. ES-MS (M+H$^+$): 216.05

Part D. 3-((1E)-1-methyl-2-{N-[4-(2-sulfamoylphenyl)phenyl]carbamoyl}vinyl)benzene-carboxamidine To a solution of 2'-tert-butylaminosulfonyl-4-amino-[1,1']-biphenyl (79 mg, 0.26 mmol) in 4 ml anhydrous dichloromethane was added a solution of 2M trimethylaluminum in hexane (0.39 ml, 0.78 mmol). Reaction was stirred at room temperature for 20 minutes to which a solution of ethyl (E) 3-(3-cyanophenyl)-2-propenoate (56 mg, 0.26 mmol) in 1 ml anhydrous dichloromethane was added. Reaction was stirred at room temperature overnight. Reaction was quenched with 5 ml 1N HCl after which an additional 10 ml dichloromethane was added. Organic layer was washed with 2×20 ml water, dried over magnesium sulfate, filtered and concentrated to give the (2E)-N-[4-(2-{[(tert-butyl)amino]sulfonyl}phenyl)phenyl]-3-(3-cyanophenyl)but-2-enamide (90 mg, 72%) as an off-white powder which was sufficiently pure to be used without further purification.

To a solution of (2E)-N-[4-(2-{[(tert-butyl)amino]sulfonyl}phenyl)phenyl]-3-(3-cyanophenyl)but-2-enamide (90 mg, 0.19 mmol) in 5 ml anhydrous methanol cooled in an ice bath was bubbled HCl gas until saturation was achieved. Reaction was allowed to warm to room temperature and stirred overnight. The reaction was then concentrated in vacuo and dried under hi vacuum. The dried residue was dissolved in 5 ml anhydrous methanol to which ammonium acetate (77 mg, 1 mmol) was added and the reaction heated to reflux for 2 hours. The reaction was concentrated and purified on a 2×25 cm Vydac C$_{18}$ HPLC column to give 3-((1E)-1-methyl-2-{N-[4-(2-sulfamoylphenyl)phenyl]carbamoyl}vinyl)benzene-carboxamidine (15 mg, 20%) as a fluffy white powder after lyophilization. ES-MS (M+E$^+$): 435.1

Example 20

3-((1Z)-1-Methyl-2-{N-[4-(2-sulfamoylphenyl)phenyl]carbamoyl}vinyl)-benzenecarboxamidine

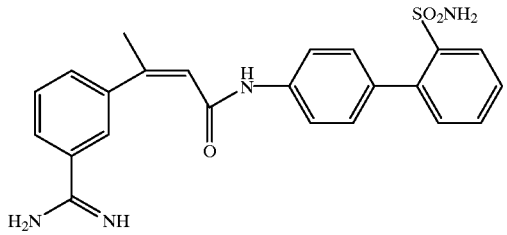

To a solution of 2'-tert-butylaminosulfonyl-4-amino-[1,1']-biphenyl (198 mg, 0.65 mmol) in 5 ml anhydrous dichloromethane was added a solution of 2M trimethylaluminum in hexane (0.98 ml, 1.95 mmol). Reaction was stirred at room temperature for 20 minutes to which a solution of ethyl (Z) 3-(3-cyanophenyl)-2-propenoate (140 mg, 0.65 mmol) in 1 ml anhydrous dichloromethane was added. Reaction was stirred at room temperature overnight. Reaction was quenched with 5 ml 1N HCl after which an additional 20 ml dichloromethane was added. Organic was washed with 2×25 ml water, dried over magnesium sulfate and concentrated to give (2Z)-N-[4-(2-{[(tert-butyl)amino]sulfonyl}phenyl)phenyl]-3-(3-cyanophenyl)but-2-enamide (200 mg, 65%) as a light brown residue which was sufficiently pure to be used without further purification.

To a solution of (2Z)-N-[4-(2-{[(tert-butyl)amino]sulfonyl}phenyl)phenyl]-3-(3-cyanophenyl)but-2-enamide (90 mg, 0.19 mmol) in 5 ml anhydrous methanol cooled in an ice bath was bubbled HCl gas until saturation was achieved. Reaction was allowed to warm to room temperature and stirred overnight. The reaction was then concentrated in vacuo and dried under hi vacuum. The dried residue was dissolved in 5 ml anhydrous methanol to which ammonium acetate (144 mg, 2 mmol) was added and the reaction heated to reflux for 2 hours. The reaction was concentrated and purified on a 2×25 cm Vydac C$_{18}$ HPLC column to give 3-((1Z)-1-methyl-2-{N-[4-(2-sulfamoylphenyl)phenyl]carbamoyl}vinyl)-benzenecarboxamidine (35 mg, 20%) as a fluffy white powder after lyophilization. ES-MS (M+H$^+$): 435.1

Example 21
3-((1E)-2-{N-[4-(2-Sulfamoylphenyl)phenyl]carbamoyl}-1-(trifluoromethyl)vinyl)benzenecarboxamidine

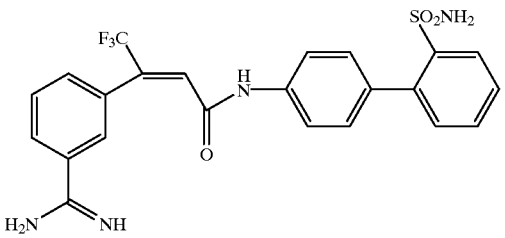

Part A. Ethyl (Z)-4,4,4-trifluoro-3-{[(trifluoromethyl)sulfonyl]-oxy}-2-butenoate To a solution of ethyl trifluoroacetoacetate (5 g, 27.2 mmol) in 20 ml anhydrous dichloromethane was added triethylamine (5.7 ml, 40.7 mmol). Reaction was cooled under argon to −78° C. to which trifluoromethanesulfonic anhydride (11.5 g, 10.5 mmol) was added dropwise via syringe over 5 minutes. Reaction was allowed to warm to room temperature and stirred over night. Next morning the reaction was diluted with 25 ml dichloromethane, organic was washed with 2×50 ml water, 2×50 ml 1N HCl, dried over magnesium sulfate, filtered and concentrated in vacuo. Crude oil was chromatographed on silica gel using 5% EtOAc in hexane as the eluent to give ethyl (Z)-4,4,4-trifluoro-3-{[(trifluoromethyl)sulfonyl]-oxy}-2-butenoate (7.7 g, 90%) as a clear light yellow oil after drying. $H^1$NMR (CDCl$_3$): 1.31–1.35 (t, 3H); 4.33–4.35 (m, 2H); 6.535 (s, H).

Part B. Ethyl (2E)-3-(3-cyanophenyl)-4,4,4-trifluorobut-2-enoate

To a solution of ethyl (Z)-4,4,4-trifluoro-3-{[(trifluoromethyl)sulfonyl]-oxy}-2-butenoate (250 mg, 0.79 mmol) in 5 ml anhydrous dioxane was added potassium phosphate (251 mg, 1.19 mmol), 3-cyanophenyl boronic acid (116 mg, 0.79 mmol), and tetrakis (triphenylphosphine) palladium(0) (23 mg, 0.02 mmol). Reaction mixture was heated to reflux and stirred overnight. Mixture was filtered through a pad of Celite, diluted with 50 ml ethyl acetate, washed with 2×50 ml water, 2×50 ml saturated brine solution, dried over magnesium sulfate, filtered and concentrated in vacuo. Residue was chromatographed on silica gel using 20% EtOAc in hexane as the eluent to give ethyl (2E)-3-(3-cyanophenyl)-4,4,4-trifluorobut-2-enoate (150 mg, 79%) as a yellow residue after drying. $H^1$NMR (CDCl$_3$) 1.107–1.142 (t, 3H); 4.04–4.107 (m, 2H); 6.684 (s, H); 7.38–7.72 (m, 4H).

Part C. 3-((1E)-2-{N-[4-(2-Sulfamoylphenyl)phenyl]carbamoyl}-1-(trifluoromethyl)vinyl)benzenecarboxamidine To a solution of 2'-tert-butylaminosulfonyl-4-amino-[1,1']-biphenyl (79 mg, 0.26 mmol) in 5 ml anhydrous dichloromethane was added a solution of 2M trimethylaluminum in hexane (0.39 ml, 0.78 mmol). Reaction was stirred at room temperature for 20 minutes to which a solution of ethyl (Z) 3-(3-cyanophenyl)-4,4,4-trifluoro-2-butenoate (70 mg, 0.26 mmol) in 1 ml anhydrous dichloromethane was added. Reaction was stirred at room temperature overnight. Reaction was quenched with 5 ml 1N HCl after which an additional 20 ml dichloromethane was added. Organic was washed with 2×25 ml water, dried over magnesium sulfate, filtered and concentrated to give (2E)-N-[4-(2-{[(tert-butyl)aamino]sulfonyl}phenyl)phenyl]-3-(3-cyanophenyl)-4,4,4-trifluorobut-2-enamide (120 mg, 88%) as a yellow foam which was sufficiently pure to be used without further purification.

To a solution of (2E)-N-[4-(2-{[(tert-butyl)amino]sulfonyl}phenyl)phenyl]-3-(3-cyanophenyl)-4,4,4-trifluorobut-2-enamide (90 mg, 0.19 mmol) in 10 ml 1:1 ethyl acetate:anhydrous methanol cooled to −78° C. was bubbled HCl gas until saturation was achieved. Reaction was placed in the refrigerator at 0° C. over the weekend. The reaction was then concentrated in vacuo and dried under hi vacuum. The dried methyl imidate residue was dissolved in 5 ml anhydrous methanol to which ammonium acetate (144 mg, 2 mmol) was added and the reaction heated to reflux for 2 hours. The reaction was concentrated then treated with 10 ml trifluoroacetic acid for 2 hrs, concentrated and purified on a 2×25 cm Vydac C$_{18}$ HPLC column to give 3-((1E)-2-{N-[4-(2-sulfamoylphenyl)phenyl]carbamoyl}-1-(trifluoromethyl)vinyl)benzenecarboxamidine (57 mg, 47%) as a fluffy white powder after lyophilization. ES-MS (M+H$^+$): 489.15

Example 22
3-((1Z)-1-(pyrazolylmethyl)-2-{N-[4-(2-sulfamoylphenyl)phenyl]-carbamoyl}vinyl)benzenecarboxamidine

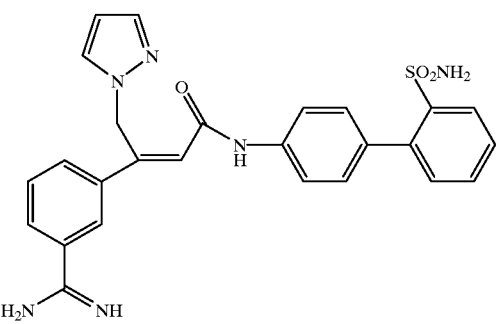

Part A. Ethyl (Z) 3-(3-cyanophenyl)-4-bromo-2-butenoate

To a solution of ethyl (Z) 3-(3-cyanophenyl)-2-butenoate (2 g, 9.3 mmol) in 50 ml carbon tetrachloride was added N-bromosuccinimide (1.74 g, 9.77 mmol) and benzoyl peroxide (40 mg, 0.165 mmol). Reaction mixture was heated to reflux and stirred over night. Reaction was allowed to cool to room temperature to which 50 ml dichloromethane was added. Organic was washed with 2×50 ml water, dried over magnesium sulfate, filtered and concentrated in vacuo. Crude residue was chromatographed on silica gel using 2.5% EtOAc in hexane as the eluent to give ethyl (Z) 3-(3-cyanophenyl)-4-bromo-2-butenoate (0.77 g, 29%) as a clear oil (note: NOE experiment showed compound isomerized during bromination). $H^1$NMR (CDCl$_3$) 1.311–1.347 (t, 3H); 4.239–4.292 (m, 2H); 4.92 (s, 2H); 6.18 (s, H); 7.514–7.801 (m, 4H). ES-MS (M+H$^+$): 293.95 and 296.0

Part B. Ethyl (Z)-3-(3-cyanophenyl)-4-(1H-1-pyrazolyl)-2-butenoate

To a solution of ethyl (Z) 3-(3-cyanophenyl)-4-bromo-2-butenoate (103 mg, 0.35 mmol) in 5 ml anhydrous di-methylformamide was added pyrazole (24 mg, 0.35 mmol) and cesium carbonate (228 mg, 0.7 mmol). Reaction mixture was stirred for 1.5 hours at room temperature after which 25 ml ethyl acetate was added. Organic was washed with 3×25 ml water, 3×50 ml saturated brine solution, dried over magnesium sulfate, filtered and concentrated to give ethyl (Z)-3-(3-cyanophenyl)-4-(1H-1-pyrazolyl)-2-butenoate (70 mg, 71%) as a brown residue which was sufficiently pure to be used without further purification. ES-MS (M+H$^+$): 282.1

Part C. 3-((1Z)-1-(Pyrazolylmethyl)-2-{N-[4-(2-sulfamoylphenyl)phenyl]carbamoyl}vinyl)-benzenecarboxamidine To a solution of 2'-tert-butylaminosulfonyl-4-amino-[1,1']-biphenyl (76 mg, 0.25 mmol) in 4 ml anhydrous dichloromethane was added a solution of 2M trimethylaluminum in hexane (0.38 ml, 0.75 mmol). Reaction was stirred at room temperature for 20 minutes to which a solution of ethyl (Z)-3-(3-cyanophenyl)-4-(1H-1-pyrazolyl)-2-butenoate (70 mg, 0.25 mmol) in 1 ml anhydrous dichloromethane was added. Reaction was stirred at room temperature overnight. Reaction was quenched with 5 ml 1N HCl after which an additional 20 ml dichloromethane was added. Organic was washed with 2×20 ml water, dried over magnesium sulfate and concentrated to give the tButyl nitrile of the title compound (120 mg, 89%) as a brown foam, which was sufficiently pure to use in the next step.

To a solution of the above nitrile compound (120 mg, 0.22 mmol) in 10 ml 1:1 ethyl acetate:anhydrous methanol cooled to −78° C. was bubbled HCl gas until saturation was achieved. Reaction was allowed to warm to room temperature and stirred overnight. The reaction was then concentrated in vacuo and dried under hi vacuum. The dried methyl imidate residue was dissolved in 5 ml anhydrous methanol to which ammonium acetate (77 mg, 1 mmol) was added and the reaction heated to reflux for 2 hours. The reaction was concentrated, then treated with trifluoroacetic acid (10 ml) for 2 hours, concentrated and purified on a 2×25 cm Vydac $C_{18}$ HPLC column to give 3-((1Z)-1-(pyrazolylmethyl)-2-{N-[4-(2-sulfamoylphenyl)phenyl]-carbamoyl}vinyl) benzenecarboxamidine (10 mg, 9%) as a fluffy white powder after lyophilization. ES-MS (M+H$^+$): 501.1

Example 23

3-((1E)-1-(Pyrazolylmethyl)-2-{N-[4-(2-sulfamoylphenyl) phenyl]carbamoyl}vinyl)benzenecarboxamidine.

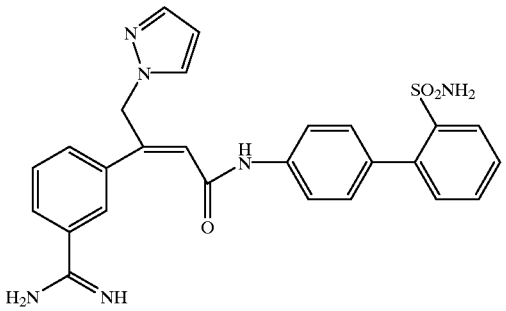

Part A. 3-(2-bromoacetyl) benzonitrile

To a solution of 3-acetobenzonitrile (5 g, 0.0344 mol) in 45 ml glacial acetic acid was added pyridinium tribromide (11.3 g, 0.0355 mol). Reaction was stirred at room temperature under argon overnight. Reaction was then quenched with a saturated sodium sulfite solution (20 ml) and extracted with 3×25 ml dichloromethane. Combined organic phases were washed with 2×25 ml water, dried over magnesium sulfate, filtered and concentrated in vacuo. Crude oil was chromatographed on silica gel using 5% EtOAc in hexane as the eluent to give 3-(2-bromoacetyl) benzonitrile (4.5 g, 58%) as a white solid. H$^1$NMR (CDCl$_3$) 4.371–4.403 (s, 2H); 7.613–7.664 (m, H); 7.838–7.888 (m, H); 8.192–8.261 (m, 2H)

Part B. 3-[2-(1H-1-Pyrazolyl)acetyl]benzonitrile

To a solution of 3-(2-bromoacetyl)benzonitrile (500 mg, 2.23 mmol) in 5 ml dichloromethane was added pyrazole (304 mg, 4.46 mmol) and triethylamine (0.31 ml, 2.23 mmol). Reaction was stirred at room temperature over night. Reaction was then diluted with 20 ml dichloromethane, washed with 2×25 ml water, 2×25 ml 1N HCl, dried over magnesium sulfate, filtered and concentrated in vacuo. Crude residue was chromatographed on silica gel using 2.5% EtOAc in hexane to give 3-[2-(1H-1-pyrazolyl)acetyl] benzonitrile (330 mg, 70%) as a clear oil after drying. ES-MS (M+H$^+$): 212.05

Part C. Methyl (E)-3-(3-cyanophenyl)-4-(1H-1-pyrazolyl)-2-butenoate

To a solution of bis(2,2,2-trifluoroethyl)(methoxycarbonylmethyl)phosphonate (0.39 ml, 1.87 mmol) in 5 ml anhydrous tetrahydrofuran was added a solution of 18-crown-6 (2 g, 7.8 mmol) in 5 ml anhydrous tetrahydrofuran. Reaction was cooled to −78° C. to which a 0.5M solution of potassium bis(trimethylsilyl)amide in toluene (0.93 ml, 1.87 mmol) was added all at once. The reaction mixture was stirred at −78° C. for 20 minutes after which a solution of 3-[2-(1H-1-pyrazolyl)acetyl]-benzonitrile (330 mg, 1.56 mmol) in 5 ml anhydrous tetrahydrofuran was added dropwise over several minutes. Reaction was gradually allowed to warm to room temperature and stirred for 5 hours. Reaction was then quenched with a saturated ammonium chloride solution (10 ml) and extracted with 2×25 ml diethyl ether. Combined organic layers were washed with 2×25 ml water, 2×25 ml saturated brine solution, dried over magnesium sulfate, filtered and concentrated to a brown residue. Crude residue was chromatographed on silica gel using a gradient of 5% EtOAc in hexane containing 0.1% triethylamine to 20% EtOAc in hexane containing 0.1% triethylamine to give methyl (E)-3-(3-cyanophenyl)-4-(1H-1-pyrazolyl)-2-butenoate (135 mg, 32%) as a clear oil after drying. H$^1$NMR (CDCl$_3$) 3.521 (s, #H); 4.98 (s, 2H); 5.694 (s, H); 6.237–6.247 (t, H); 7.296–7.593 (m, 6H). NOE experiment confirmed the stereochemical configuration.

Part D. 3-((1E)-1-(Pyrazolylmethyl)-2-{N-[4-(2-sulfamoylphenyl)phenyl]carbamoyl}vinyl)-benzenecarboxamidine To a solution of 2'-tert-butylaminosulfonyl-4-amino-[1,1']-biphenyl (105 mg, 0.34 mmol) in 4 ml anhydrous dichloromethane was added a solution of 2M trimethylaluminum in hexane (0.5 ml, 1.02 mmol). Reaction was stirred at room temperature for 20 minutes to which a solution of methyl (E)-3-(3-cyanophenyl)-4-(1H-1-pyrazolyl)-2-butenoate (90 mg, 0.34 mmol) in 1 ml anhydrous dichloromethane was added. Reaction was stirred at room temperature overnight. Reaction was quenched with 5 ml 1N HCl after which an additional 20 ml dichloromethane was added. Organic was washed with 2×20 ml water, dried over magnesium sulfate, filtered and concentrated to give (2E)-N-[4-(2-{[(tert-butyl) amino]sulfonyl}phenyl)phenyl]-3-(3-cyanophenyl)but-2-enamide (155 mg, 85%) as an off-white foam which was sufficiently pure to be used without further purification.

To a solution of (2E)-N-[4-(2-{[(tert-butyl)amino] sulfonyl}phenyl)phenyl]-3-(3-cyanophenyl)but-2-enamide (155 mg, 0.287 mmol) in 10 ml 1:1 ethyl acetate:anhydrous methanol cooled to −78° C. was bubbled HCl gas until saturation was achieved. Reaction was allowed to warm to room temperature and stirred overnight. The reaction was then concentrated in vacuo and dried under hi vacuum. The dried methyl imidate residue was dissolved in 5 ml anhydrous methanol to which ammonium acetate (77 mg, 1 mmol) was added and the reaction heated to reflux for 2 hours. The reaction was concentrated, treated with trifluoroacetic acid (10 ml) for 2 hrs, concentrated and purified on a 2×25 cm Vydac $C_{18}$ HPLC column to give 3-((1E)-1-

Example 24
3-((1E)-1-(2-Furyl)-2-{N-[4-(2-sulfamoylphenyl)phenyl]carbamoyl}vinyl)benzenecarboxamidine

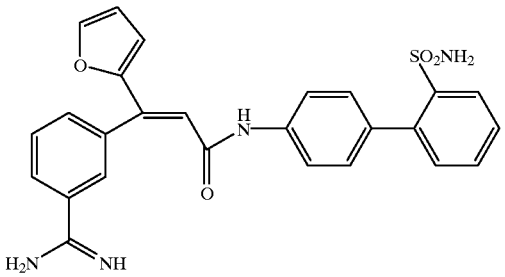

Part A. Ethyl (Z)-3-(2-furyl)-3-{[(trifluoromethyl)sulfonyl]-oxy}-2-propenoate

To a solution of ethyl B-oxo-3-furanpropionate (1 g, 5.49 mmol) in 5 ml anhydrous dichloromethane was added triethylamine (0.847 ml, 6.04 mmol). Reaction was cooled under argon to −78° C. to which trifluoromethanesulfonic anhydride (1.02 ml, 6.04 mmol) was added dropwise via syringe over 5 minutes. Reaction was allowed to warm to room temperature and stirred over night. Next morning the reaction was diluted with 25 ml dichloromethane, organic was washed with 2×50 ml water, 2×50 ml 1N HCl, dried over magnesium sulfate, filtered and concentrated in vacuo. The crude oil was chromatographed on silica gel using 20% EtOAc in hexane as the eluent to give ethyl (Z)-3-(2-furyl)-3-{[(trifluoromethyl)sulfonyl]-oxy}-2-propenoate (1.6 g, 93%) as a light brown solid after drying. $H^1$NMR (CDCl$_3$) 1.31–1.35 (t, 3H); 4.26–4.314 (m, 2H); 6.065 (s, H); 6.522 (s, H); 7.47 (s, H); 7.76 (s, H).

Part B. Ethyl (E) 3-(3-cyanophenyl)-3-(2-furyl)-2-propenoate

To a solution of ethyl (Z)-3-(2-furyl)-3-{[(trifluoromethyl)sulfonyl]-oxy}-2-propenoate (500 mg, 1.59 mmol) in 7 ml anhydrous dioxane was added potassium phosphate (506 mg, 2.4 mmol), 3-cyanophenyl boronic acid (234 mg, 1.59 mmol), and tetrakis (triphenylphosphine) palladium(0) (46 mg, 0.04 mmol). Reaction mixture was heated to reflux and stirred overnight. Mixture was filtered through a pad of Celite, diluted with 50 ml ethyl acetate, washed with 2×50 ml water, 2×50 ml saturated brine solution, dried over magnesium sulfate, filtered and concentrated in vacuo. The crude residue was chromatographed on silica gel using a gradient from 5% EtOAc in hexane to 10% EtOAc in hexane as the eluent to give ethyl (E) 3-(3-cyanophenyl)-3-(2-furyl)-2-propenoate (100 mg, 24%) as a clear yellow oil after drying. $H^1$NMR (CDCl$_3$) 1.1–1.14 (t, 3H); 4.016–4.035 (m, 2H); 5.293 (s, H); 7.45–7.549 (m, 3H); 7.669 (m, H). ES-MS (M+H$^+$): 268.05

Part C. 3-((1E)-1-(2-Furyl)-2-{N-[4-(2-sulfamoylphenyl)phenyl]carbamoyl}vinyl)benzenecarboxamidine To a solution of 2'-tButylaminosulfonyl-4-amino-[1,1']-biphenyl (102 mg, 0.336 mmol) in 4 ml anhydrous dichloromethane was added a solution of 2M trimethylaluminum in hexane (0.5 ml, 1.0 mmol). Reaction was stirred at room temperature for 20 minutes to which a solution of ethyl (E) 3-(3-cyanophenyl)-3-(2-furyl)-2-propenoate (90 mg, 0.336 mmol) in 1 ml anhydrous dichloromethane was added. Reaction was stirred at room temperature overnight. Reaction was quenched with 5 ml 1N HCl after which an additional 20 ml dichloromethane was added. Organic was washed with 2×20 ml water, dried over magnesium sulfate and concentrated to give (2E)-N-[4-(2-{[(tert-butyl)amino]sulfonyl}phenyl)phenyl]-3-(3-cyanophenyl)-3-(2-furyl)prop-2-enamide (200 mg, 112%) as a brown foam which was sufficiently pure to be used without further purification.

To a solution of (2E)-N-[4-(2-{[(tert-butyl)amino]sulfonyl}phenyl)phenyl]-3-(3-cyanophenyl)-3-(2-furyl)prop-2-enamide (176 mg, 0.336 mmol) in 10 ml 1:1 ethyl acetate:anhydrous methanol cooled to −78° C. was bubbled HCl gas until saturation was achieved. Reaction was allowed to warm to room temperature and stirred overnight. The reaction was then concentrated in vacuo and dried under hi vacuum. The dried methyl imidate residue was dissolved in 5 ml anhydrous methanol to which ammonium acetate (144 mg, 2 mmol) was added and the reaction heated to reflux for 2 hours. The reaction was concentrated, treated with trifluoroacetic acid (10 ml) for 2 hrs, concentrated and purified on a 2×25 cm Vydac C$_{18}$ HPLC column to give 3-((1E)-1-(2-furyl)-2-{N-[4-(2-sulfamoylphenyl)phenyl]carbamoyl}vinyl)benzenecarboxamidine (60 mg, (37%) as a fluffy off-white powder after lyophilization. ES-MS (MA+H$^+$): 487.15

Example 25
1-((1E)-1-(Methoxymethyl)-2-{N-[4-(2-sulfamoylphenyl)phenyl]carbamoyl}vinyl)benzenecarboxamidine

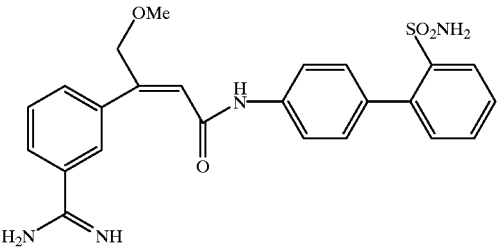

Part A. Methyl (Z)-4-methoxy-3-{[(trifluoromethyl)sulfonyl]-oxy}-2-butenoate

To a solution of methyl 4-methoxy-3-oxobutanoate (5 g, 34.2 mmol) in 20 ml anhydrous dichloromethane was added triethylamine (5.24 ml, 37.6 mmol). Reaction was cooled under argon to −78° C. to which trifluoromethanesulfonic anhydride (10.6 gml, 37.6 mmol) was added dropwise via syringe over 5 minutes. Reaction was allowed to warm to room temperature and stirred over night. Next morning the reaction was diluted with 25 ml dichloromethane, organic was washed with 2×50 ml water, 2×50 ml 1N HCl, dried over magnesium sulfate, filtered and concentrated in vacuo. The crude oil was chromatographed on silica gel using a gradient of 5% EtOAc in hexane to 10% EtOAc in hexane as the eluent to give methyl (Z)-4-methoxy-3-{[(trifluoromethyl)sulfonyl]-oxy}-2-butenoate (5.1 g, 54%) as a clear colorless oil after drying. $H^1$NMR (CDCl$_3$) 3.342 (s, 3H); 3.711 (s, 3H); 3.99 (s, H); 6.02 (s, H).

Part B. Methyl (E)-3-(3-cyanophenyl)-4-methoxy-2-butenoate

To a solution of methyl (Z)-4-methoxy-3-{[(trifluoromethyl)sulfonyl]-oxy}-2-butenoate (246 mg, 1.0

145 mmol) in 5 ml anhydrous dioxane was added potassium phosphate (318 mg, 1.5 mmol), 3-cyanophenyl boronic acid (162 mg, 1.0 mmol), and tetrakis (triphenylphosphine) palladium(0) (29 mg, 0.0251 mmol). Reaction mixture was heated to reflux and stirred overnight. Mixture was filtered through a pad of Celite, diluted with 20 ml ethyl acetate. Organic was washed with 2×20 ml water, 2×20 ml saturated brine solution, dried over magnesium sulfate, filtered and concentrated in vacuo to give methyl (E)-3-(3-cyanophenyl)-4-ethoxy-2-butenoate (220 mg, 75%) as a clear brown oil which was sufficiently pure to be used without further purification. ES-MS (M+H$^+$): 232.1

Part C. 3-((1E)-1-(Methoxymethyl)-2-{N-[4-(2-sulfamoylphenyl)phenyl]carbamoyl}vinyl) benzenecarboxamidine To a solution of 2'-tButylaminosulfonyl-4-amino-[1,1']-biphenyl (105 mg, 0.35 mmol) in 4 ml anhydrous dichloromethane was added a solution of 2M trimethylaluminum in hexane (0.53 ml, 1.05 mmol). Reaction was stirred at room temperature for 20 minutes to which a solution of methyl (E) 3-(3-cyanophenyl)-4-methoxy-2-butenoate (80 mg, 0.35 mmol) in 1 ml anhydrous dichloromethane was added. Reaction was stirred at room temperature overnight. Reaction was quenched with 5 ml 1N HCl after which an additional 20 ml dichloromethane was added. Organic was washed with 2×20 ml water, dried over magnesium sulfate and concentrated to give (2E)-N-[4-(2-{[(tert-butyl)amino] sulfonyl}phenyl)phenyl]-3-(3-cyanophenyl)-4-methoxybut-2-enamide (150 mg, 85%) as a white foam after drying which was sufficiently pure to be used without further purification.

To a solution of (2E)-N-[4-(2-{[(tert-butyl)amino] sulfonyl}phenyl)phenyl]-3-(3-cyanophenyl)-4-methoxybut-2-enamide (150 mg, 0.298 mmol) in 10 ml 1:1 ethyl acetate:anhydrous methanol cooled to −78° C. was bubbled HCl gas until saturation was achieved. Reaction was allowed to warm to room temperature and stirred overnight. The reaction was then concentrated in vacuo and dried under hi vacuum. The dried methyl imidate residue was dissolved in 5 ml anhydrous methanol to which ammonium acetate (77 mg, 1 mmol) was added, and the reaction heated to reflux for 2 hours. The reaction was concentrated, treated with trifluoroacetic acid (10 ml) for 2 hrs, concentrated and purified on a 2×25 cm Vydac C$_{18}$ HPLC column to give 3-((1E)-1-(methoxymethyl)-2-{N-[4-(2-sulfamoylphenyl)phenyl] carbamoyl}vinyl)benzenecarboxamidine (34 mg, (25%) as a fluffy off-white powder after lyophilization. ES-MS (M+H$^+$): 465.15

To a solution of 3-((1E)-1-(methoxymethyl)-2-{N-[4-(2-sulfamoylphenyl)phenyl]carbamoyl}vinyl)-benzenecarboxamidine (5 mg, 0.01 mmol) in 4 ml methanol was added 10% Pd on carbon (1 mg). Mixture was treated with hydrogen at 1 atmosphere under balloon for 1 hr. Reaction was filtered through a pad of Celite, concentrated and lyophilized to give 3-(1-(methoxymethyl)-2-{N-[4-(2-sulfamoylphenyl)phenyl]carbamoyl}-ethyl) benzenecarboxamidine (5 mg, 100%) as a fluffy white powder. ES-MS (M+H$^+$): 467.15

146

Example 26

Preparation of (2E)-N-{4-[(2-aminosulfonyl)phenyl] phenyl}-N-(carboxylmethyl)-3-(3-amidinophenyl)-2-fluoro-3-methylacrylamide.

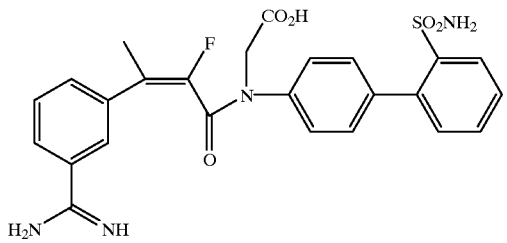

A. Preparation of (2E)-N-{4-[(2-tert-butylaminosulfonyl) phenyl]phenyl}-N-(methoxycarbonylmethyl)-3-(3-cyanophenyl)-2-fluoro-3-methylacrylamide To a solution of (2E)-N-[4-(2-{[(tert-butyl)amino] sulfonyl}phenyl)phenyl]-3-(3-cyanophenyl)-2-fluorobut-2-enamide (230 mg, 0.47 mmol) in 15 ml DMF was added cesium carbonate (460 mg, 1.41 mmol) and bromomethyl acetate (355 mg, 2.35 mmol). The reaction mixture was stirred at room temperature for 4 hours then diluted with 25 ml of ethyl acetate. Organic was washed with 3×25 ml water, 3×25 ml saturated brine solution, dried over magnesium sulfate, filtered and concentrated in vacuo to give methyl 2-{(2E)-N-[4-(2-{[(tert-butyl)amino]-sulfonyl}phenyl) phenyl]-3-(3-cyanophenyl)-2-fluorobut-2-enoylamino}acetate (230 mg, 86%) as yellow foam. ES-MS (M+H$^+$): 563.2.

B. Preparation of (2E)-N-{4-[(2-aminosulfonyl)phenyl] phenyl}-N-(methoxycarbonylmethyl)-3-(3-amidinophenyl)-2-fluoro-3-methylacrylamide To a solution methyl 2-{(2E)-N-[4-(2-}[(tert-butyl) amino]-sulfonyl}phenyl)phenyl]-3-(3-cyanophenyl)-2-fluorobut-2-enoylamino acetate (230 mg, 0.408 mmol) in 10 ml 1:1 ethyl acetate:anhydrous methanol cooled to −78° C. was bubbled HCl gas until saturation was achieved. Reaction was allowed to warm to room temperature and stirred 18 hours. The reaction was then concentrated in vacuo and dried under hi vacuum. The dried methyl imidate residue was dissolved in 5 ml anhydrous methanol to which ammonium acetate (11 mg, 1.5 mmol) was added and the reaction heated to reflux for 2 hours. The reaction was then concentrated and purified on a 2×25 cm Vydac C$_{18}$ HPLC column to give methyl 2-{(2E)-3-(3-amidinophenyl)-2-fluoro-N-[4-(2-sulfamoylphenyl)phenyl]but-2-enoylamino}acetate (150 mg, 70%) as a fluffy white powder after lyophilization. ES-MS (M+H$^+$): 525.2.

C. Preparation of (2E)-N-{4-[(2-aminosulfonyl)phenyl] phenyl}-N-(carboxylmethyl)-3-(3-amidinophenyl)-2-fluoro-3-methylacrylamide To a solution of methyl 2-{(2E)-3-(3-amidinophenyl)-2-fluoro-N-[4-(2-sulfamoylphenyl)phenyl]but-2-enoylamino}acetate (100 mg, 0.19 mmol) in 5 ml methanol was added a 0.5N lithium hydroxide solution (1 ml, 0.5 mmol). The reaction was stirred at room temperature for 4 hours then concentrated and purified on a 2×25 cm Vydac C$_{18}$ HPLC column to give 2-{(2E)-3-(3-amidinophenyl)-2-fluoro-N-[4-(2-sulfamoylphenyl)phenyl]but-2-enoylamino}acetic acid (70 mg, 71%) as a fluffy white powder after lyophilization. ES-MS (M+H$^+$): 511.1.

Example 27
Preparation of (2Z)-N-{4-[(2-aminosulfonyl)phenyl]phenyl}-3-(3-amidinophenyl)-3-isopropylacrylamide

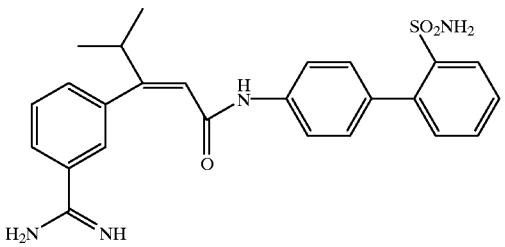

A. Preparation of 3-(2-methylpropanoyl)benzenecarbonitrile.

To a mixture prepared by adding copper cyanide (940 mg, 10.5 mmol) to a cooled solution of lithium bromide (1.82 g 21 mmol) in tetrahydrofurn at −25° C. under argon atmosphere was added a solution of 0.5M 3-cyanophenyl zinc iodide (20 ml, 10 mmol) in tetrahydrofuran. The reaction mixture was allowed to warm to 0° C. for 30 minutes then cooled down to −25° C. to which neat isobutyryl chloride (1.06 ml, 10.1 mmol) was added all at once. The reaction was kept at −25° C. for 30 minutes then quenched by adding 20 ml of a saturated solution of ammonium chloride. The mixture was extracted with 2×25 ml diethyl ether. The combined organic layers were dried over magnesium sulfate, filtered and concentrated in vacuo to an oil. The crude oil was flushed through a silica plug using 10% ethyl acetate in hexane to give 3-(2-methylpropanoyl)benzenecarbonitrile (1.25 g, 72%) as a clear oil. $H^1$NMR ($CDCl_3$): 2.2–2.25 (d, H); 4.499–4.568 (m, H); 8.614–8.655 (m, 2H); 8.831–8.857 (m, H); 9.172–9.238 (m, H). ES-M ($M+H^+$): 174.1.

B. Preparation of (2Z)-methyl 3-(cyanophenyl)-3-isopropylacrylate

To a solution of bis(2,2,2-trifluoromethyl)(methoxy carbonylmethyl)phosphonate (0.38 ml, 1.8 mmol) in 2.5 ml anhydrous tetrahydrofuran was added a solution of 18-Crown-6 (1.9 g, 7.5 mmol) in 2.5 ml anhydrous tetrahydrofuran. The reaction mixture was cooled to −78° C. under argon to which was added a solution of 0.5M bis(trimethylsilyl)amide in toluene (3.6 ml, 1.8 mmol). The reaction was stirred at −78° C. for 15 minutes to which was added a solution of 3-(2-methylpropanoyl)benzenecarbonitrile in 2.5 ml anhydrous tetrahydrofuran. The reaction was allowed to warm to room temperature and stirred for 48 hours. The reaction was quenched by the addition of 20 ml of a saturated ammonium chloride solution followed by extraction with 2×25 ml diethyl ether. Combined organic layers were washed with 2×25 ml water, 2×25 ml saturated brine solution, dried over magnesium sulfate, filtered and concentrated to give a 9:1 mixture of methyl (2Z)-3-(3-cyanophenyl)-4-methylpent-2-enoate and methyl (2E)-3-(3-cyanophenyl)-4-methylpent-2-enoate (420 mg, 120%) as a clear oil which was sufficiently pure to use without further purification. ES-MS ($M+H^+$): 230.1.

C. Preparation of (2Z)-N-{4-[(2-tert-butylaminosulfonyl)phenyl]phenyl}-3-(3-cyanophenyl)-3-isopropylacrylamide To a solution of 2'-tert-butylaminosulfonyl-4-amino-[1,1']-biphenyl (139 mg, 0.46 mmol) in 4 ml anhydrous dichloromethane was added a solution of 2M trimethylaluminum in hexane (0.69 ml, 1.38 mmol). Reaction was stirred at room temperature for 20 minutes to which a solution of crude methyl (2Z)-3-(3-cyanophenyl)-4-methylpent-2-enoate (105 mg, 0.46 mmol) in 2 ml anhydrous dichloromethane was added. Reaction was stirred at room temperature overnight. Reaction was quenched with 5 ml 1N HCl after which an additional 20 ml dichloromethane was added. Organic was washed with 2×20 ml water, dried over magnesium sulfate, filtered and concentrated to give (2Z)-N-[4-(2-{[(tert-butyl)amino]sulfonyl}phenyl)phenyl]-3-(3-cyanophenyl)-4-methylpent-2-enamide (190 mg, 82%) as an off-white foam which was sufficiently pure to be used without further purification. ES-MS ($M^{+H}$): 501.2.

D. Preparation of (2Z)-N-{4-[(2-aminosulfonyl)phenyl]phenyl}-3-(3-amidinophenyl)-3-isopropylacrylamide To a solution of crude (2Z)-N-[4-(2-{[(tert-butyl)amino]sulfonyl}phenyl)phenyl]-3-(3-cyanophenyl)-4-methylpent-2-enamide (190 mg, 0.379 mmol) in 10 ml 1:1 ethyl acetate-:anhydrous methanol cooled to −78° C. was bubbled HCl gas until saturation was achieved. Reaction was allowed to warm to room temperature and stirred overnight. The reaction was then concentrated in vacuo and dried under hi vacuum. The dried methyl imidate residue was dissolved in 5 ml anhydrous methanol to which ammonium acetate (115 mg, 1.5 mmol) was added and the reaction heated to reflux for 2 hours. The reaction was concentrated and purified on a 2×25 cm Vydac $C_{18}$ HPLC column to give 3-((1Z)-1-(methylethyl)-2-{N-[4-(2-sulfamoylphenyl)phenyl]carbamoyl}vinyl)benzene carboxamidine (75 mg, 43%) as a fluffy white powder after lyophilization. ES-MS ($M+H^+$): 463.2.

Example 28
3-(2-{N-[4-(2-Sulfamoylphenyl)phenyl]carbamoyl}cyclopent-1-enyl)benzenecarboxamidine

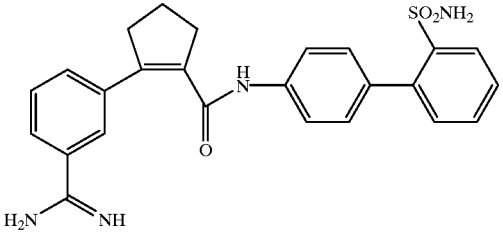

A. Preparation of Ethyl 2-{[(trifluoromethyl)sulfonyl]oxy}-1-cyclopentene-1-carboxylate To a solution of ethyl 2-oxocyclopentane carboxylate (1.56 g, 10 mmol) in 20 ml anhydrous dichloromethane was added triethylamine (1.06 g, 10.5 mmol). Reaction was cooled under argon to −78° C. to which trifluoromethanesulfonic anhydride (2.96 g, 10.5 mmol) was added dropwise via syringe over 5 minutes. Reaction was allowed to warm to room temperature and stirred over night. Next morning the reaction was diluted with 25 ml dichloromethane, organic was washed with 2×50 ml water, 2×50 ml 1N HCl, dried over magnesium sulfate, filtered and concentrated to give ethyl 2-{[(trifluoromethyl)sulfonyl]oxy}-1-cyclopentene-1-carboxylate (2.8 g, 97%) as a light brown oil after drying. $H^1$NMR ($CDCl_3$) δ 1.27–1.56 (t, 3H); 1.97–2.01 (m, 2H); 2.6–2.74 (m, 4H); 4.21–4.26 (m, 2H).

Part B Preparation of Ethyl 2-(3-cyanophenyl)-1-cyclopentene-1-carboxylate

To a solution of ethyl 2-{[(trifluoromethyl)sulfonyl]oxy}-1-cyclopentene-1-carboxylate (1.2 g, 4.16 mmol) in 10 ml anhydrous dioxane was added potassium phosphate (1.32 g, 6.2 mmol), 3-cyanophenyl boronic acid (0.612 g, 4.16 mmol), and tetrakis(triphenylphosphine)palladium(0) (0.12 g, 0.10 mmol). Reaction mixture was heated to reflux and stirred overnight. Mixture was filtered through a pad of Celite, diluted with 50 ml ethyl acetate, washed with 2×50 ml water, 2×50 ml saturated brine solution, dried over magnesium sulfate, filtered and concentrated in vacuo. Residue was chromatographed on silica gel using 5% EtOAc in hexane as the eluent to give ethyl 2-(3-cyanophenyl)-1-cyclopentene-1-carboxylate (0.7 g, 71%) as a light yellow oil after drying. ES-MS (M+H$^+$): 242.15. H$^1$NMR (CDCl$_3$) δ: 1.09–1.13 (t, 3H); 1.96–2.01 (m, 2H); 2.80–2.84 (m, 4H); 7.39–7.59 (m, 4H).

Part C Preparation of 3-(2-{N-[4-(2-Sulfamoylphenyl)phenyl]carbamoyl}cyclopent-1-enyl)benzenecarboxamidine To a solution of 2'-tert-butylaminosulfonyl-4-amino-[1,1']-biphenyl (60 mg, 0.197 mmol) in 4 ml anhydrous dichloromethane was added a solution of 2M trimethylaluminum in hexane (0.3 ml, 0.59 mmol). Reaction was stirred at room temperature for 20 minutes to which a solution of ethyl 2-(3-cyanophenyl)-1-cyclopentene-1-carboxylate (48 mg, 0.197 mmol) in 1ml anhydrous dichloromethane. Reaction was stirred at room temperature overnight. Reaction was quenched with 15 ml 1N HCl after which an additional 10 ml dichloromethane was added. Organic was washed with 2×20 ml water, dried over magnesium sulfate and concentrated to give N-[4-(2-{[(tert-butyl)amino]sulfonyl}phenyl)phenyl][2-(3-cyanophenyl)cyclopent-1-enyl]carboxamide (80 mg, 80%) as a white powder which was sufficiently pure to be used without further purification.

To a solution of N-[4-(2-{[(tert-butyl)amino]sulfonyl}phenyl)phenyl][2-(3-cyanophenyl)cyclopent-1-enyl]carboxamide (70 mg, 0.137 mmol) in 5 ml anhydrous methanol cooled in an ice bath was bubbled HCl gas until saturation was achieved. Reaction was allowed to warm to room temperature and stirred overnight. The reaction was then concentrated in vacuo and dried under hi vacuum. The dried residue was dissolved in 5 ml anhydrous methanol to which ammonium acetate (77 mg, 1 mmol) was added and the reaction heated to reflux for 2 hours. The reaction was concentrated and purified on a 2×25 cm Vydac C$_{18}$ HPLC column to give 3-(2-{N-[4-(2-sulfamoylphenyl)phenyl]carbamoyl}cyclopent-1-enyl)benzenecarboxamidine (40 mg, 63%) as a fluffy white powder after lyophilization. ES-MS (M+H$^+$): 461.15

BIOLOGICAL ACTIVTY EXAMPLES

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 μM. In the assays for thrombin, prothrombinase and factor Xa, a synthetic chromogenic substrate is added to a solution containing test compound and the enzyme of interest and the residual catalytic activity of that enzyme is determined spectrophotometrically. The IC$_{50}$ of a compound is determined from the substrate turnover. The IC$_{50}$ is the concentration of test compound giving 50% inhibition of the substrate turnover. The compounds of the present invention desirably have an IC$_{50}$ of less than 500 nM in the factor Xa assay, preferably less than 200 nM, and more preferred compounds have an IC$_{50}$ of about 100 nM or less in the factor Xa assay. The compounds of the present invention desirably have an IC$_{50}$ of less than 4.0 μM in the prothrombinase assay, preferably less than 200 nM, and more preferred compounds have an IC$_{50}$ of about 10 nM or less in the prothrombinase assay. The compounds of the present invention desirably have an IC$_{50}$ of greater than 1.0 μM in the thrombin assay, preferably greater than 10.0 μM, and more preferred compounds have an IC$_{50}$ of greater than 100.0 μM in the thrombin assay.

Amidolytic Assays for Determining Protease Inhibition Activity

The factor Xa and thrombin assays are performed at room temperature, in 0.02 M Tris.HCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al, Thromb. Res., 75, 427–436 (1994). Specifically, the activity of the prothrombinase complex is determined by measuring the time course of thrombin generation using the p-nitroanilide substrate Chromozym TH. The assay consists of preincubation (5 minutes) of selected compounds to be tested as inhibitors with the complex formed from factor Xa (0.5 nM), factor Va (2 nM), phosphatidyl serine:phosphatidyl choline (25:75, 20 μM) in 20 mM Tris.HCl buffer, pH 7.5, containing 0.15 M NaCl, 5 mM CaCl$_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis Model

Administration of compounds in the rabbit venous thrombosis model demonstrates antithrombotic efficacy at the higher doses evaluated. There are no significant effects of the compound on the aPTT and PT prolongation with the highest dose (100 μg/kg+2.57 μg/kg/min). Compounds have no significant effects on hematological parameters as compared to saline controls. All measurements are an average of all samples after steady state administration of vehicle or (D)-Arg-Gly-Arg-thiazole. Values are expressed as mean±SD.

Without further description, it is believed that one of ordinary skill in the art can, using the preceding description and the following illustrative examples, make and utilize the compounds of the present invention and practice the claimed methods.

What is claimed is:

1. A compound of the formula:

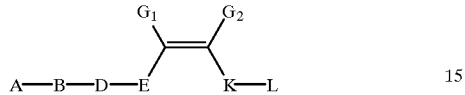

wherein:

A is selected from:
(a) phenyl, which is independently substituted with 0–2 R substituents;
(b) naphthyl, which is independently substituted with 0–2 R substituents; and
(c) an aromatic or non-aromatic monocyclic heterocyclic ring system having from 5 to 8 ring atoms, wherein 1–4 ring atoms of the ring system are selected from N, O and S, and wherein the ring system may be substituted with 0–2 R substituents;

R is selected from:
halo, —$C_{1-4}$alkyl substituted by up to 4 of the same or different halogen atoms selected independently from the group consisting of chlorine, bromine, iodine and fluorine atoms, —$C_{1-4}$alkyl, —$C_{1-4}$alkyl-phenyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_m NR^1 R^2$, —$SO_2NR^1R^2$, —$SO_2R^1$, —C(=O)—$NR^1R^2$, —$CF_3$, —$OR^1$, and a 5–6 membered aromatic heterocyclic system containing from 1–4 heteroatoms selected from N, O and S, wherein from 1–4 hydrogen ring atoms on the aromatic heterocyclic system, or on the phenyl portion of the —$C_{1-4}$alkyl-phenyl group, may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$NH_2$; —N(—$C_{1-4}$alkyl, —$C_{0-4}$alkyl), and —$NO_2$;

$R^1$ and $R^2$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —C(=O)—OH, —C(=O)—O—$C_{1-6}$alkyl, —C(=O)—$NH_2$, —C(=O)—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$NH_2$; —N(—$C_{1-4}$alkyl, —$C_{0-4}$alkyl), and —$NO_2$;

m is an integer of 0–2;

B is a direct link;

$R^3$, $R^{3a}$ and $R^{3b}$ are each independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$ cycloalkyl, —CN, and —$NO_2$;

D is a member selected from the group consisting of:
(a) phenyl, which is independently substituted with 0–2 $R^a$ substituents; and
(b) an aromatic six-membered heterocyclic ring having from 1–2 ring nitrogen atoms, and wherein the ring atoms may be substituted with 0–2 $R^a$ substituents;

$R^a$ is selected from:
halo, —$C_{1-4}$alkyl, —$C_{2-6}$alkenyl, —C2-6alkynyl, —$C_{3-8}$cycloalkyl, —$C_{0-4}$alkyl$C_{3-8}$cycloalkyl, —CN, —$NO_2$, —$(CH_2)_n NR^{1a}R^{2a}$, —$SO_2NR^{1a}R^{2a}$, —$SO_2R^{1a}$, —$CF_3$, —$SR^{1a}$, —$OR^{1a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN and —$NO_2$;

n is an integer of 0–2;

$R^{1a}$ and $R^{2a}$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

$G^1$ and $G^2$ are each independently a member selected from the group consisting of:
hydrogen, halo, —$C_{1-6}$alkyl, haloalkyl, —CN, —NO2, —$C_{2-6}$alkenyl, —$C_{2-6}$alkynyl, —$C_{3-8}$cycloalkyl, —$C_{0-4}$alkyl—$C_{3-8}$-cycloalkyl, —$C_{0-4}$alkyl-CN, —$C_{0-4}$alkyl-$NO_2$, —$C_{0-4}$alkyl-O—$R^4$, —$C_{0-4}$alkyl-S—$R^4$, —$C_{0-4}$alkyl-S(=O)—$R^4$, —$C_{0-4}$alkyl-S(O)—$R^4$, —$C_{0-4}$alkyl-C(=O)—$OR^4$, —$C_{0-4}$alkyl-C(=O)—N($R^{4a}$,$R^{4b}$), —$C_{0-4}$alkyl-C(=O)—$R^4$, —$C_{0-4}$alkyl-N($R^{4a}$,$R^{4b}$), —$C_{0-4}$alkyl-N(—$R^{4a}$)—C(=O)—$R^{4b}$), —$C_{0-4}$alkyl-N(—$R^{4a}$)—C(=O)—$R^{4b}$, —$C_{0-4}$alkyl-N(—$R^{4a}$)—C(=O)—N(—$R^{4b}$), —$C_{0-4}$alkyl-N(—$R^{4a}$)—S(=O)$_2$—$R^{4b}$, —$C_{0-4}$ alkyl-S(=O)$_2$—N(R$^{4a}$,R$^{4b}$),
—C$_{0-4}$alkyl-S(=O)$_2$—R$^4$, —C$_{0-4}$alkyl-P(=O)(—OR$^{4a}$)(—OR$^{4b}$), —C$_{0-4}$alkyl-N(—R$^4$)-P(=O)(—OR$^{4a}$)(—OR$^{4b}$), —C$_{0-4}$alkyl-phenyl, —C$_{0-4}$alkyl-naphthyl, —C$_{0-4}$alkyl-heterocyclic ring system containing from 1–4 heteroatoms selected from the group consisting of O, N and S, wherein the heterocyclic ring system is a 5–6 membered monocyclic ring or a 8–12 membered bicyclic ring, and wherein 0–4 hydrogen atoms of the phenyl ring, the naphthyl ring carbon and the heterocyclic ring system are replaced by a member selected from the group consisting of —C$_{1-4}$alkyl, haloalkyl, halo, —CN, —NO$_2$, —OR$^{4c}$, —SR$^{4c}$, —S(O)R$^{4c}$, —C(=O)—OR$^{4c}$, —C(=O)—N(—R$^{4c}$,R$^{4d}$), —C(=O)—R$^{4c}$, —N(R$^{4c}$,R$^{4d}$), —N(—R$^{4c}$)—C(=O)—R$^{4d}$, —N(—R$^{4c}$)—C(=O)—OR$^{4d}$, —N(—R$^{4c}$)—C(=O)—N(—H,R$^{4d}$), —N(—R$^{4c}$)—SO$_2$—R$^{4d}$, —SO$_2$—N(—R$^{4c}$,—R$^{4d}$), —SO$_2$—R$^{4c}$; or G1 and a nitrogen on the E group can combine to form a 5–7 membered heterocyclic ring containing a 0–3 additional heteroatoms selected from the group consisting of O, N and S;

R$^4$, R$^{4a}$, R$^{4b}$, R$^{4c}$ and R$^{4d}$ are each independently a member selected from the group consisting of:

H, halo —C$_{1-6}$alkyl, —C$_{2-6}$alkenyl, —C$_{2-6}$alkynyl, —C$_{3-8}$cycloalkyl, —C$_{0-4}$alkyl-C$_{3-8}$cycloalkyl, —CH$_2$CH$_2$OH, —CH$_2$CH$_2$—O—CH$_3$, —C$_{0-4}$alkylphenyl, —C$_{0-4}$alkylheterocycle wherein the heterocycle may be a 5-6 membered ring, and wherein from 0–4 hydrogen atoms from the ring atoms of the phenyl and heterocycle groups may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkyl-C$_{3-8}$cycloalkyl, —CN, —NO$_2$, —C(=O)—OH, —C(=O)—O—C$_{1-4}$alkyl, —C(=O)—NH$_2$, —C(=O)—N(—H, —C1–4alkyl), and —C(=O)—N(—C$_{1-4}$alkyl, —C$_{1-4}$alkyl);

alternatively, R$^{4a}$ taken with R$^{4b}$ or R$^{4c}$ taken with R$^{4d}$ when either pair of groups is attached to the same nitrogen atom may combine with that nitrogen atom to form a 5–8 membered saturated, partially saturated or unsaturated ring which contains from 0–1 additional heteroatoms selected from a group consisting of —N, —O, S, wherein any S ring atom may be present as a —S—, —S(=O)— or —S(=O)$_2$— group;

E is —N(R$^5$)—C(=O)—;

wherein R$^5$, R$^6$, R$^{5a}$, R$^{6a}$, R$^{5b}$ R$^{6b}$, R$^{5c}$ and R$^{6c}$ are each independently selected from:

H, —OH, —O—C$_{1-4}$alkyl, —C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl, C$_{0-4}$alkylnaphthyl, C$_{0-4}$alkylheteroaryl, C$_{1-4}$alkylCOOH and C$_{1-4}$alkylCOOC$_{1-4}$alkyl, wherein from 0–4 hydrogen atoms on the ring atoms of the phenyl, naphthyl and heteroaryl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{-04}$alkylC$_{3-8}$cycloalkyl, —OH, —O—C$_{1-4}$alkyl, —SH, —S—C$_{1-4}$ alkyl, —CN and —NO$_2$;

K is a member selected from the group consisting of:
(a) phenyl, which is independently substituted with 0–2 R$^b$ substituents;
(b) naphthyl, which is independently substituted with 0–2 R$^b$ substituents; and
(c) a monocyclic or used bicyclic heterocyclic ring system having from 5 to 10 ring atoms, wherein 1–4 ring atoms of the ring system are selected from N, O and S, and wherein the ring system may be substituted with 0–2 R$^b$ substituents;

R$^b$ is a member selected from the group consisting of:

halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN, NR$^{1b}$R$^{2b}$, SO$_2$NR$^{1b}$R$^{2b}$, SO$_2$R$^{1b}$, CF$_3$, OR$^{1b}$, O—CH$_2$—CH$_2$—OR$^{1b}$, O—CH$_2$—COOR$^{1b}$, N(R$^{1b}$)—CH$_2$—CH$_2$—OR$^{1b}$, N(—CH$_2$—CH$_2$—OR$^{1b}$)$_2$, N(R$^{1b}$)—C(=O)R$^{2b}$, N(R$^{1b}$)—SO$_2$—R$^{2b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

R$^{1b}$ and R$^{2b}$ are independently selected from the group consisting of:

H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

L is selected from:

H, —CN, C(=O)NR$^{12}$R$^{13}$, (CH$_2$)$_n$NR$^{12}$R$^{13}$, —C(=NR$^{12}$)NR$^{12}$R$^{13}$, —CH=N—N(—R$^{12}$)—C(=NR$^{12a}$, —N(—R$^{12b}$,—R$^{12c}$), —OR$^{12}$, —NR$^{12}$C(=NR$^{12}$)NR$^{12}$R$^{13}$, and NR$^{12}$C(=NR$^{12}$)—R$^{13}$;

R$^{12}$, R$^{12a}$, R$^{12b}$, R$^{12c}$ and R$^{13}$ are independently selected from:

hydrogen, —OR$^{14}$, —NR$^{14}$R$^{15}$, C$_{1-4}$alkyl, C$_{0-4}$alkylphenyl, C$_{0-4}$alkylnaphthyl, COOC$_{1-4}$alkyl, COO—C$_{0-4}$alkylphenyl and COO—C$_{0-4}$alkylnaphthyl, wherein from 1–4 hydrogen atoms on the ring atoms of the phenyl and naphthyl moieties may be independently replaced with a member selected from the group consisting of halo, —OH, —O—C$_{1-4}$alkyl, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN, and —NO$_2$;

R$^{14}$ and R$^{15}$ are independently selected from:

H, C$_{1-4}$alkyl, —C(=O)—O—C$_{0-6}$alkyl, —C(=O)—NH$_2$, —C(=O)—N(—H, —C$_{1-6}$alkyl) —C(=O)—N(—C$_{1-6}$alkyl, —C$_{1-6}$alkyl), —C(=O)—N(—H, —C$_{1-6}$alkyl-N(—C$_{1-6}$alkyl, —C$_{1-6}$alkyl)), —C(=O)—N(—C$_{1-6}$ alkyl, —C$_{1-6}$alkyl-N(—C$_{1-6}$alkyl, —C$_{1-6}$alkyl)), —C(=O)—([N,N]-piperazino-C$_{1-6}$ alkyl), —C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, and —COO—$C_{0-4}$alkyl;

and all pharmaceutically acceptable isomers, salts, hydrates, solvates and prodrug derivatives thereof.

2. A compound according to claim 1 of the formula:

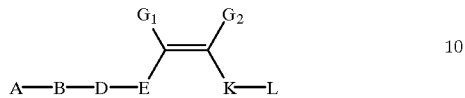

wherein:
A is selected from:
  (a) phenyl, which is independently substituted with 0–2 R substituents;
  (b) naphthyl, which is independently substituted with 0–2 R substituents; and
  (c) an aromatic or non-aromatic monocyclic heterocyclic ring system having from 5 to 8 ring atoms, wherein 1–4 ring atoms of the ring system are selected from N, O and S, and wherein the ring system may be substituted with 0–2 R substituents;
R is selected from:
  halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_m NR^1 R^2$, —$SO_2 NR^1 R^2$, —C(=O)—$NR^1 R^2$, —$SO_2 R^1$, —$CF_3$, —$OR^1$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl and —$NO_2$;
$R^1$ and $R^2$ are independently selected from the group consisting of:
  H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —C(=O)—OH, —C(=O)—O—$C_{1-6}$alkyl, —C(=O)—$NH_2$, —C(=O)—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$–$C_4$-alkyl, —CN, —$C_{1-4}$alkyl, —$C_{2-6}$alkenyl, —$C_{2-6}$ alkynyl, —$C_{3-8}$cycloalkyl, —$C_{0-4}$alkyl$C_{3-8}$ cycloalkyl, —$NH_2$; —N(—$C_{1-4}$alkyl, —$C_{0-4}$ alkyl), and —$NO_2$;
m is an integer of 0–2;
B is a direct link;

D is a member selected from the group consisting of:
  (a) phenyl, which is independently substituted with 0–2 $R^a$ substituents; and
  (b) an aromatic six-membered heterocyclic ring having from 1–2 ring nitrogen atoms, and wherein the ring atoms may be substituted with 0–2 $R^a$ substituents;
$R^a$ is selected from:
  halo, —$CF_3$, —$CHF_2$, —$CH_2$—F, —$SR^{1a}$ and —$OR^{1a}$;
  $R^{1a}$, in each occurrence, is independently selected from the group consisting of:
    H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;
$G^1$ and $G^2$ are each independently selected from hydrogen or $R^{1a}$;
$R^4$ is independently a member selected from the group consisting of:
  F; Br; Cl; —CN; —$NO_2$; —$C_{1-6}$alkyl; —O—$C_{1-6}$alkyl; —$C_{1-4}$alkyl substituted by up to 4 of the same or different halogen atoms independently selected from the group consisting of F, Br, and Cl; —$C_{3-8}$ cycloalkyl substituted by up to 6 of the same or different halogen atoms independently selected from the group consisting of F, Br, and Cl; phenyl; pyridyl; pyrimidyl; imidazolyl; pyrrolyl; furanyl; thiophenyl; tetrazolyl; pyrazolyl; oxazolyl; isoxazolyl; —O—$C_{1-4}$alkyl; —N(—H)—C(=O)—$C_{1-6}$ alkyl; —N(—H)—C(=O)-phenyl; methoxycarbonylphenyl; carboxyphenyl; —$(CH_2)_n$—C(=O)—OH; —$(CH_2)_n$—C(=O)—O—$C_{1-6}$alkyl, —$(CH_2)_n$—C(=O)—N(—H, —$C_{1-6}$alkyl; —$(CH_2)_n$—C(=O)—N(—$C_{1-6}$alkyl, —$C_{1-6}$alkyl), —$(CH_2)_n$—C(=O)—[N]-morpholinyl; —$(CH_2)_n$—C(=O)—[N]-piperidyl; —$(CH_2)_n$—C(=O)—[N]-piperazinyl; —$(CH_2)_n$—S(=O)$_2$—$C_{1-6}$alkyl; —$(CH_2)_n$—S(=O)$_2$-phenyl; —$(CH_2)_n$—P(=O, (—O—$C_{1-6}$alkyl)$_2$); —CN, benzyl, pryidylmethyl and imidazolylmethyl;
n is 0–2
E is —N($R^5$)—C(=O)—;
  wherein $R^5$, $R^6$, $R^{5a}$, $R^{6a}$, $R^{5b}$ $R^{6b}$, $R^{5c}$ and $R^{6c}$ are independently selected from:
    H, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$ cycloalkyl, —OH, —O—$C_{1-4}$alkyl, —SH, —S—$C_{1-4}$ alkyl, —CN and —$NO_2$;
K is a member selected from the group consisting of:
  (a) phenyl, which is independently substituted with 0–2 $R^b$ substituents;
  (b) naphthyl, which is independently substituted with 0–2 $R^b$ substituents; and (c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^b$ substituents;

$R^b$ is a member selected from the group consisting of:

halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, $NR^{1b}R^{2b}$, $SO_2NR^{1b}R^{2b}$, $SO_2R^{1b}$, $CF_3$, $OR^{1b}$, O—$CH_2$—$CH_2$—$OR^{1b}$, O—$CH_2$—$COOR^{1b}$, $N(R^{1b})$—$CH_2$—$CH_2$—$OR^{1b}$, $N(-CH_2$—$CH_2$—$OR^{1b})_2$, $N(R^{1b})$—$C(=O)R^{2b}$, $N(R^{1b})$—$SO_2$—$R^{2b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{1b}$ and $R^{2b}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

L is selected from:

H, —CN, $C(=O)NR^{12}R^{13}$, $(CH_2)_nNR^{12}R^{13}$, —$C(=NR^{12})NR^{12}R^{13}$, —CH=N—N(—$R^{12}$)—C(=$NR^{12a}$, —N(—$R^{12b}$,—$R^{12c}$), —$OR^{12}$, —$NR^{12}C(=NR^{12})NR^{12}R^{13}$, and $NR^{12}C(=NR^{12})$—$R^{13}$;

$R^{12}$, $R^{12a}$, $R^{2b}$, $R^{12c}$ and $R^{13}$ are independently selected from:

hydrogen, —$OR^{14}$, —$NR^{14}R^{15}$, $C_{1-4}$alkyl, $C_{0-4}$alkylphenyl, $C_{0-4}$alkylnaphthyl, $COOC_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, —OH, —O—$C_{1-4}$alkyl, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

$R^{14}$ and $R^{15}$ are independently selected from:

H, $C_{1-4}$alkyl, —$C(=O)$—O—$C_{0-6}$alkyl, —$C(=O)$—$NH_2$, —$C(=O)$—N(—H, —$C_{1-6}$alkyl) —$C(=O)$—N(—$C_{1-6}$alkyl, —$C_{1-6}$alkyl), —$C(=O)$—N(—H, —$C_{1-6}$alkyl-N(—$C_{1-6}$alkyl, —$C1-_6$alkyl)), —$C(=O)$—N(—$C_{1-6}$ alkyl, —$C_{1-6}$alkyl-N(—$C_{1-6}$alkyl, —$C_{1-6}$ alkyl)), —$C(=O)$—([N,N]-piperazino-$C_{1-6}$ alkyl), —$C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, and —COO—$C_{0-4}$alkyl;

and all pharmaceutically acceptable isomers, salts, hydrates, solvates and prodrug derivatives thereof.

3. A compound according to claim 1 of the formula:

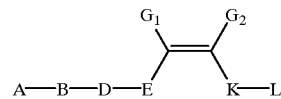

wherein:

A is selected from:
(a) phenyl, which is independently substituted with 0–2 R substituents; and
(b) an aromatic or non-aromatic monocyclic heterocyclic ring having from 5 to 6 ring atoms, wherein 1–4 ring atoms of the ring system are selected from N, O and S, and wherein the ring system may be substituted with 0–2 R substituents;

R is selected from:
—$(CH_2)_mNR^1R^2$, —$SO_2NR^1R^2$, —$C(=O)$—$NR^1R^2$, —$SO_2R^1$, —$CF_3$, —$SR^1$, —$OR^1$, and a 5–6 membered aromatic heterocyclic system containing from 1–4 heteroatoms selected from N, O and S;

$R^1$ and $R^2$ are independently selected from the group consisting of:

H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, —$C(=O)$—OH, —$C(=O)$—O—$C_{1-6}$alkyl, —$C(=O)$—$NH_2$, —$C(=O)$—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$NH_2$; —N(—$C_{1-4}$alkyl, —$C_{0-4}$alkyl), and —$NO_2$;

m is an integer of 0–2;

B is a member selected from the group consisting of:
a direct link,

D is a member selected from the group consisting of:
(a) phenyl, which is independently substituted with 0–2 $R^a$ substituents; and
(b) pyridyl, which may be substituted with 0–2 $R^a$ substituents;

R<sup>a</sup> is selected from:
halo, —CF$_3$, —CHF$_2$, —CH$_2$—F, —SR$^{1a}$ and —OR$^{1a}$;
R$^{1a}$, in each occurrence, is independently selected from the group consisting of:
H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

G$^1$ and G$^2$ are each independently selected from hydrogen or R$^4$;
R$^4$ is independently a member selected from the group consisting of:
F; Br; Cl; —CN; —NO$_2$; —C$_{1-6}$alkyl; —O—C$_{1-6}$alkyl; —C$_{1-4}$alkyl substituted by up to 4 of the same or different halogen atoms independently selected from the group consisting of F, Br, and Cl; —C$_{3-8}$ cycloalkyl substituted by up to 6 of the same or different halogen atoms independently selected from the group consisting of F, Br, and Cl; phenyl; pyridyl; pyrimidyl; imidazolyl; pyrrolyl; furanyl; thiophenyl; tetrazolyl; pyrazolyl; oxazolyl; isoxazolyl; —O—C$_{1-4}$alkyl; —N(—H)—C(=O)—C$_{1-6}$ alkyl; —N(—H)—C(=O)-phenyl; methoxycarbonylphenyl; carboxyphenyl; —(CH$_2$)$_n$—C(=O)—OH; —(CH$_2$)$_n$—C(=O)—O—C$_{1-6}$alkyl, —(CH$_2$)$_n$—C(=O)—N(—H, —C$_{1-6}$alkyl; —(CH$_2$)$_n$—C(=O)—N(—C$_{1-6}$alkyl, —C$_{1-6}$alkyl), —(CH$_2$)$_n$—C(=O)—[N]-morpholinyl; —(CH$_2$)$_n$—C(=O)—[N]-piperidyl; —(CH$_2$)$_n$—C(=O)—[N]-piperazinyl; —(CH$_2$)$_n$—S(=O)$_2$—C$_{1-6}$alkyl; —(CH$_2$)$_n$—S(=O)$_2$-phenyl; —(CH$_2$)$_n$P(=O, (—O—C$_{1-6}$alkyl)$_2$); —CN, benzyl, pryidylmethyl and imidazolylmethyl;
n is 0–2

E is —N(R$^5$)—C(=O)—;
wherein R$^5$, R$^6$, R$^{5a}$, R$^{6a}$, R$^{5b}$ R$^{6b}$, R$^{5c}$ and R$^{6c}$ are independently selected from:
H, —OH, —O—C$_{1-4}$alkyl, —C$_{1-4}$alkyl, C$_{2-6}$alkenyl, C$_{2-6}$alkynyl, C$_{3-8}$cycloalkyl, C$_{0-4}$alkylC$_{3-8}$ cycloalkyl, C$_{0-4}$alkylphenyl, C$_{0-4}$alkylnaphthyl, C$_{0-4}$alkylheteroaryl, C$_{1-4}$alkylCOOH and C$_{1-4}$alkylCOOC$_{1-4}$alkyl, wherein from 0–4 hydrogen atoms on the ring atoms of the phenyl, naphthyl and heteroaryl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$ cycloalkyl, —OH, —O—C$_{1-4}$alkyl, —SH, —S—C$_{1-4}$alkyl, —CN and —NO$_2$;

K and L taken together are a member selected from the group consisting of:

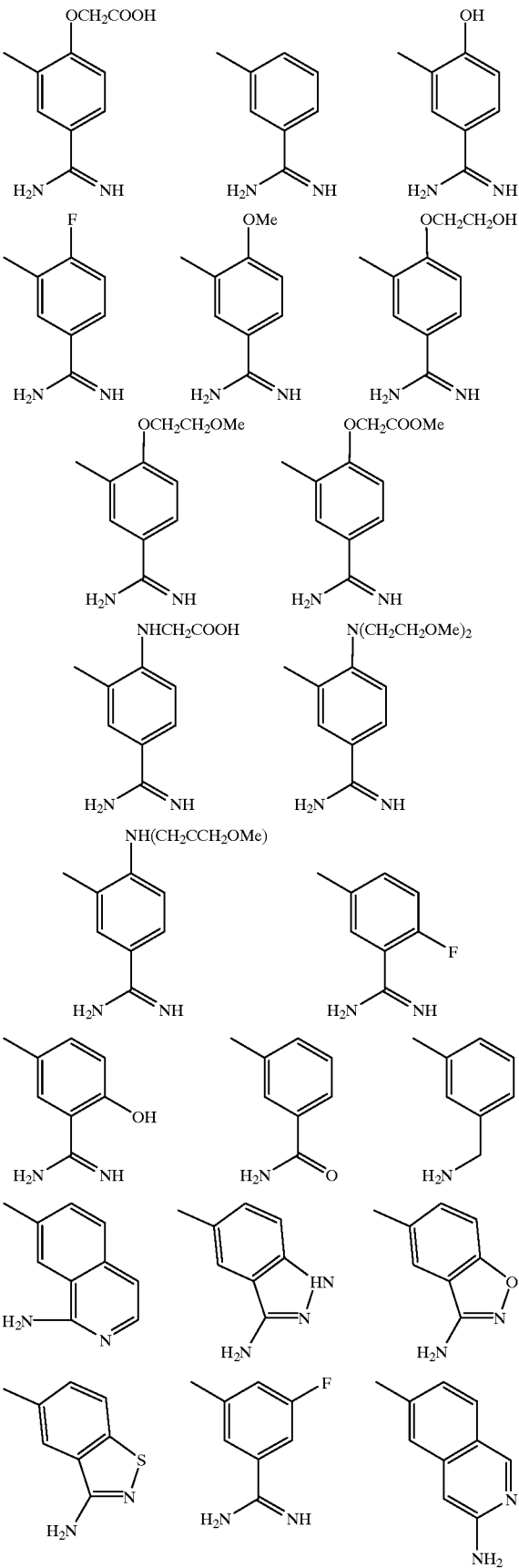

-continued

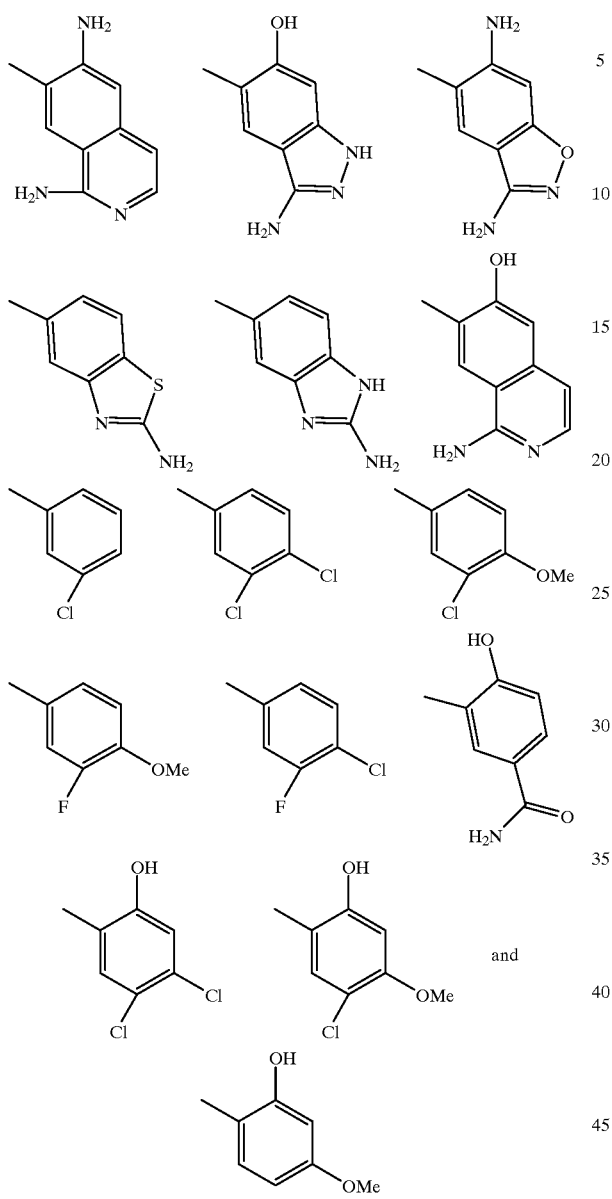

and all pharmaceutically acceptable isomers, salts, hydrates, solvates and prodrug derivatives thereof.

4. A compound according to claim 1, of the formula:

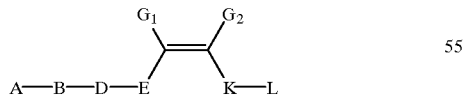

wherein:
A is selected from:
(a) phenyl, which is independently substituted with 0–2 R substituents; and
(b) an aromatic or non-aromatic monocyclic heterocyclic ring having from 5 to 6 ring atoms, wherein 1–4 ring atoms of the ring system are selected from N, O and S, and wherein the ring system may be substituted with 0–2 R substituents;

R is selected from:
—$(CH_2)_m NR^1 R^2$, —$SO_2 NR^1 R^2$, —$C(=O)$—$NR^1 R^2$, —$SO_2 R^1$, —$CF_3$, —$SR^1$, —$OR^1$, and a 5–6 membered aromatic heterocyclic system containing from 1–4 heteroatoms selected from N, O and S;
$R^1$ and $R^2$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkylC$_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkylC$_{3-8}$cycloalkyl, —CN, and —$NO_2$, —$C(=O)$—OH, —$C(=O)$—O—$C_{1-6}$alkyl, —$C(=O)$—$NH_2$, —$C(=O)$—N(—$C_{1-4}$alkyl, —$C_{0-4}$alkyl), or $R^1$ and $R^2$ combine with the nitrogen atom to which they are attached to form a 5–8 membered saturated, unsaturated or partially unsaturated heterocyclic ring containing from 0–2 further heteroatoms selected from N, O and S, wherein from 1–4 hydrogen ring atoms on the heterocyclic ring may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkylC$_{3-8}$cycloalkyl, —$NH_2$; —N(—$C_{1-4}$alkyl, —$C_{0-4}$alkyl), and —$NO_2$;
m is an integer of 0–2;
B is a member selected from the group consisting of:
a direct link,
D is a member selected from the group consisting of:
(a) phenyl, which is independently substituted with 0–2 $R^a$ substituents; and
(b) pyridyl, which may be substituted with 0–2 $R^a$ substituents;
$R^a$ is selected from:
halo, —$CF_3$, —$CHF_2$, —$CH_2$—F, —$SR^{1a}$ and —$OR^{1a}$;
$R^{1a}$, in each occurrence, is independently selected from the group consisting of:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN and —$NO_2$;
$G^1$ and $G^2$ are each independently selected from hydrogen or $R^4$;
$R^4$ is independently a member selected from the group consisting of:
F; Br; Cl; —CN; —$NO_2$; —$C_{1-6}$alkyl; —O—$C_{1-6}$alkyl; —$C_{1-4}$alkyl substituted by up to 4 of the same or different halogen atoms independently selected from the group consisting of F, Br, and Cl; —$C_{3-8}$cycloalkyl substituted by up to 6 of the same or different halogen atoms independently selected from the group consisting of F, Br, and Cl; phenyl;

pyridyl; pyrimidyl; imidazolyl; pyrrolyl; furanyl; thiophenyl; tetrazolyl; pyrazolyl; oxazolyl; isoxazolyl; —O—$C_{1-4}$alkyl; —N(—H)—C(=O)—$C_{1-6}$ alkyl; —N(—H)—C(=O)-phenyl; methoxycarbonylphenyl; carboxyphenyl; —$(CH_2)_n$—C(=O)—OH; —$(CH_2)_n$—C(=O)—O—$C_{1-6}$alkyl, —$(CH_2)_n$—C(=O)—N(—H, —$C_{1-6}$alkyl; —$(CH_2)_n$—C(=O)—N(—$C_{1-6}$alkyl, —$C_{1-6}$alkyl), —$(CH_2)_n$—C(=O)—[N]-morpholinyl; —$(CH_2)_n$—C(=O)—[N]-piperidyl; —$(CH_2)_n$—C(=O)—[N]-piperazinyl; —$(CH_2)_n$—S(=O)$_2$—$C_{1-6}$alkyl; —$(CH_2)_n$—S(=O)$_2$-phenyl; —$(CH_2)_n$—P(=O, (—O—$C_{1-6}$alkyl)$_2$); —CN, benzyl, pryidylmethyl and imidazolylmethyl;

n is 0–2

E is —N($R^5$)—C(=O)—;

wherein $R^5$, $R^6$, $R^{5a}$, $R^{6a}$, $R^{5b}$, $R^{6b}$, $R^{5c}$ and $R^{6c}$ are independently selected from:

H, —OH, —O—$C_{1-4}$alkyl, —$C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOOC$_{1-4}$alkyl, wherein from 0–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —OH, —O—$C_{1-4}$alkyl, —SH, —S—$C_{1-4}$ alkyl, —CN and —$NO_2$;

K and L taken together are a member selected from the group consisting of:

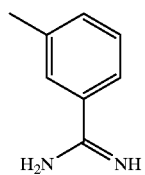 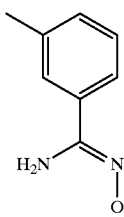 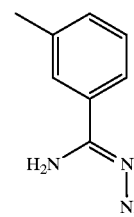

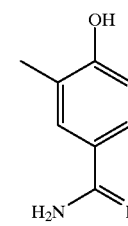 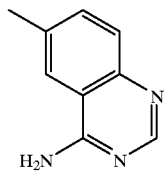 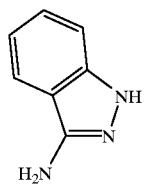

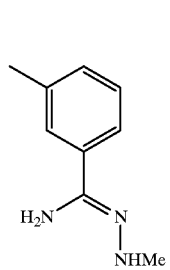 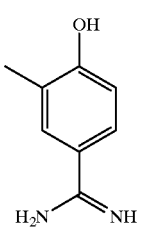 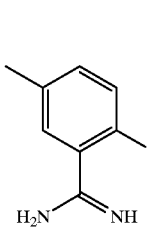

-continued

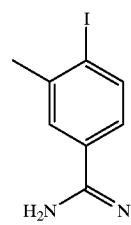 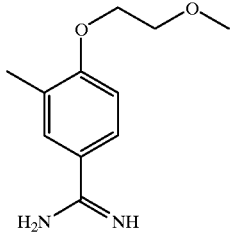

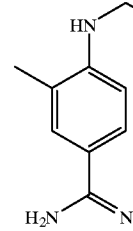 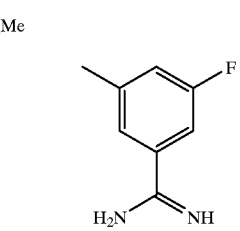

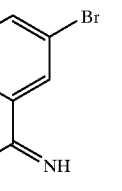 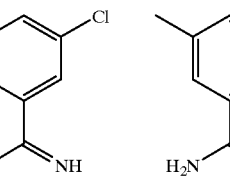

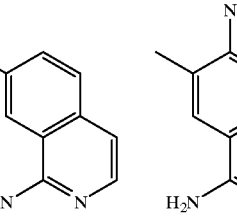

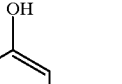 

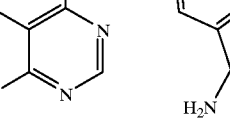

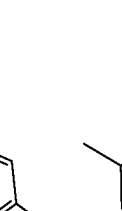 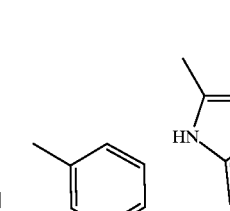

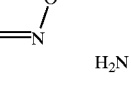 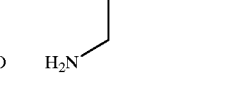

 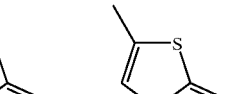

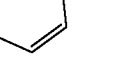 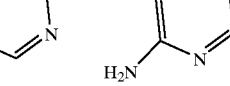

and

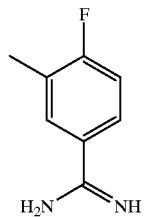 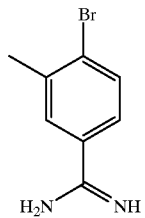 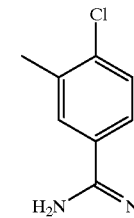

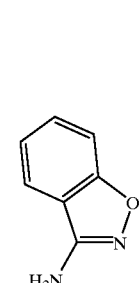 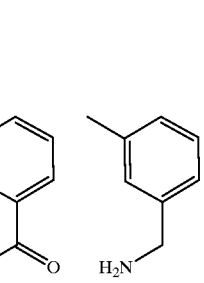 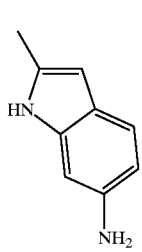

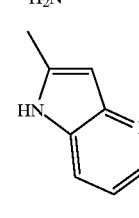 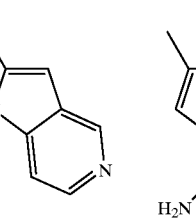 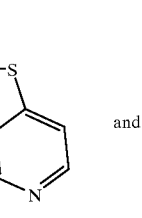

-continued

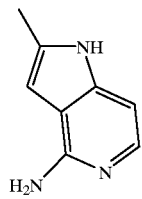

and all pharmaceutically acceptable isomers, salts, hydrates, solvates and prodrug derivatives thereof.

5. A compound according to claim 1 of the formula:

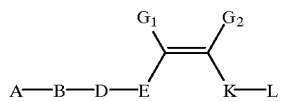

wherein:

A is a member selected from the group consisting of:

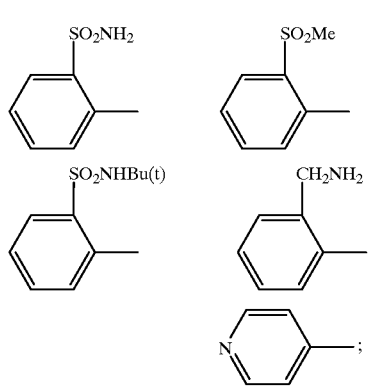

B is a direct link;

D is a member selected from the group consisting of:

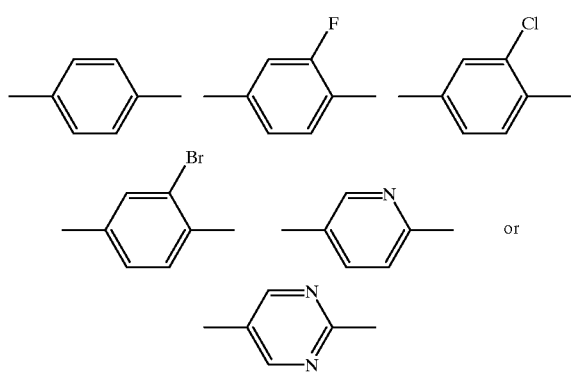

E is the group:

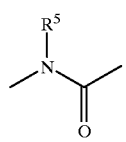

wherein $R^5$ is a member selected from the group consisting of:

H, $CH_2CO_2H$, $CH_2CO_2CH_3$, benzyl, carboxybenzyl, phenyl and carboxyphenyl;

K and L taken together are a member selected from the group consisting of:

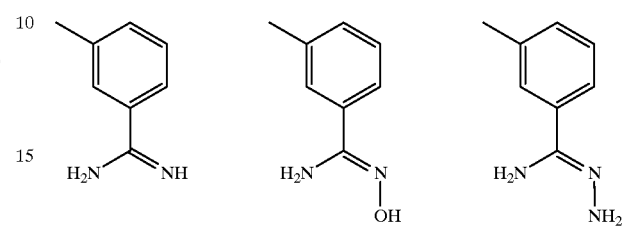

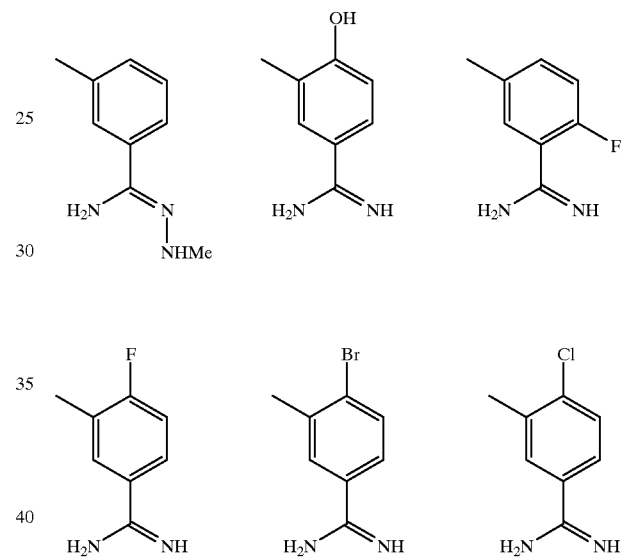

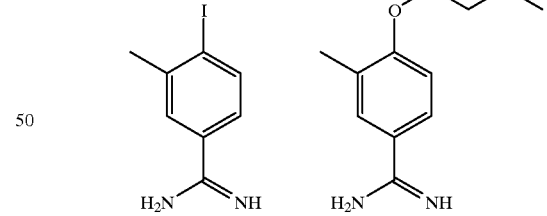

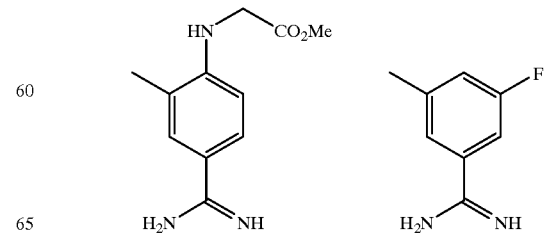

-continued
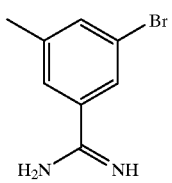 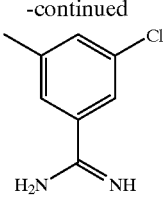 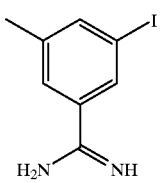
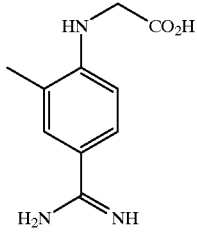 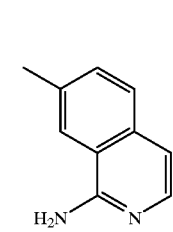 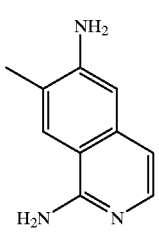
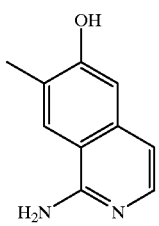 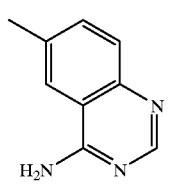 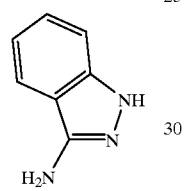
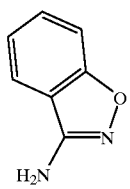 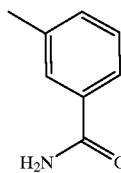 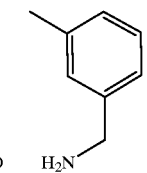 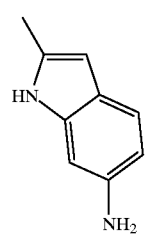
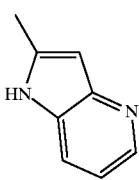 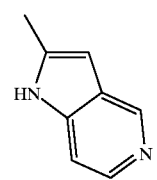 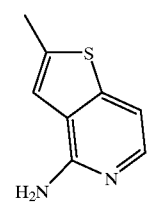 and
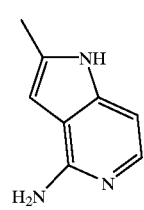
and all pharmaceutically acceptable isomers, salts, hydrates, solvates and prodrug derivatives thereof.
6. A compound according to claim 1, which is a member selected from the group consisting of:
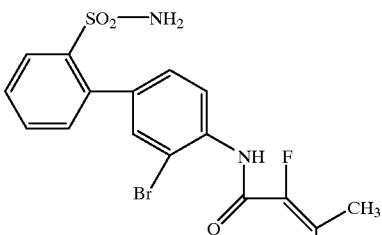
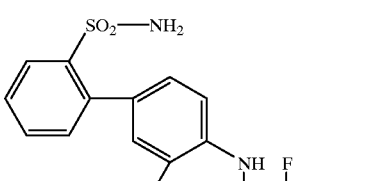
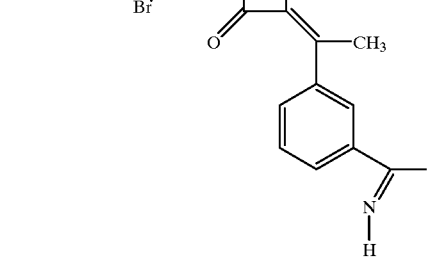
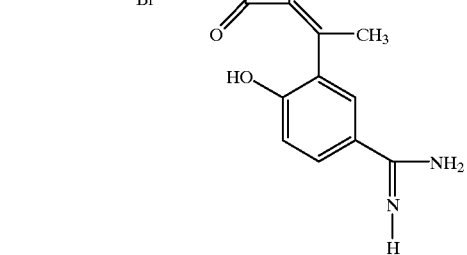 and
and all pharmaceutically acceptable isomers, salts, hydrates, solvates and prodrug

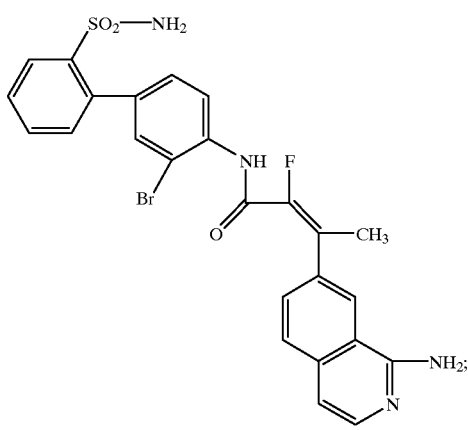

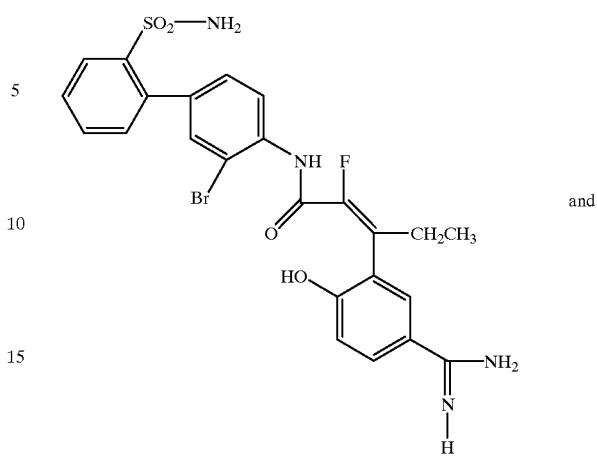

and all pharmaceutically acceptable isomers, salts, hydrates, solvates and prodrug derivatives thereof.

7. A compound according to claim 1, which is a member selected from the group consisting of:

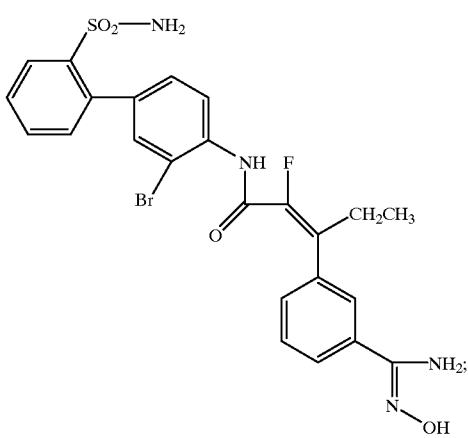

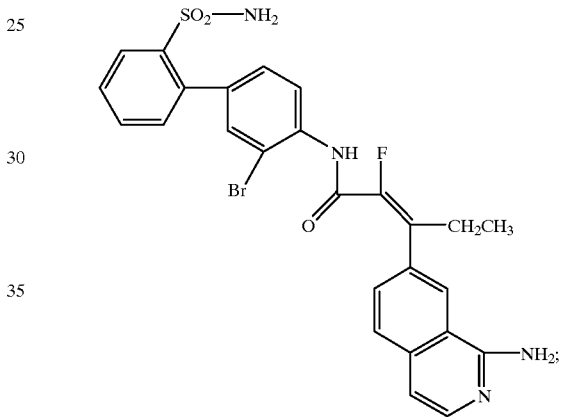

and all pharmaceutically acceptable isomers, salts, hydrates, solvates and prodrug derivatives thereof.

8. A compound according to claim 1, which is a member selected from the group consisting of:

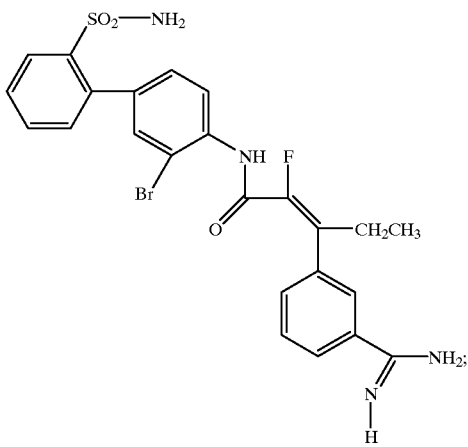

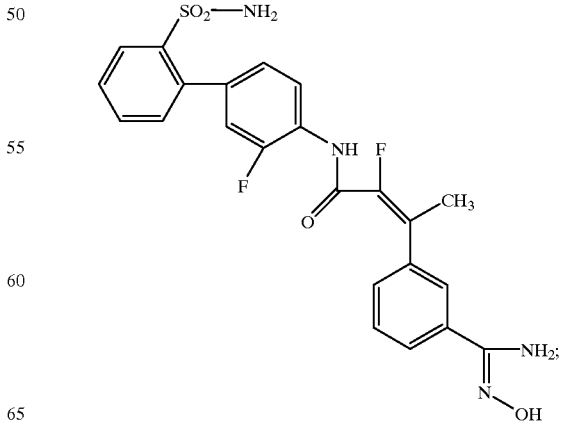

-continued
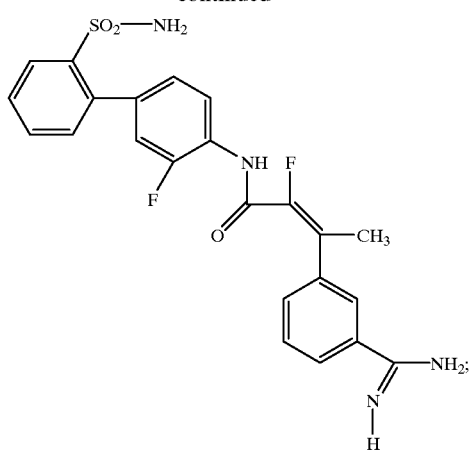
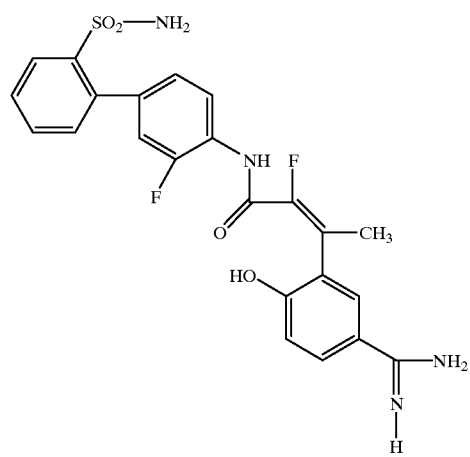
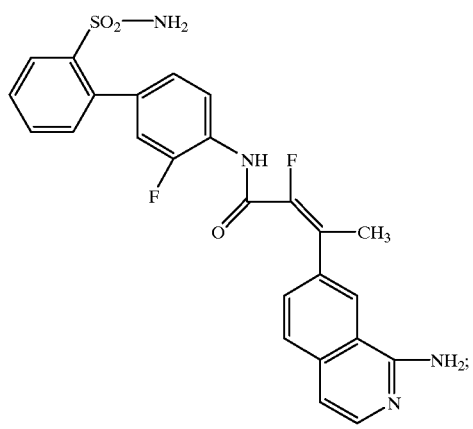
and all pharmaceutically acceptable isomers, salts, hydrates, solvates and prodrug derivatives thereof.
9. A compound according to claim 1, which is a member selected from the group consisting of:
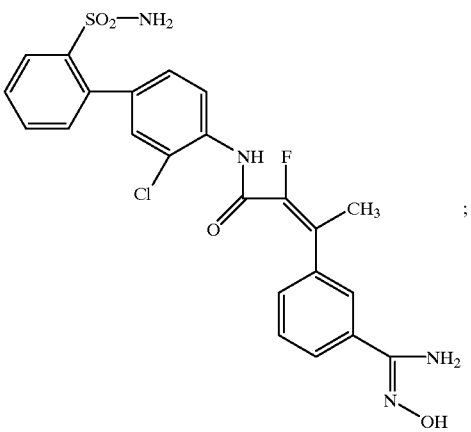
;
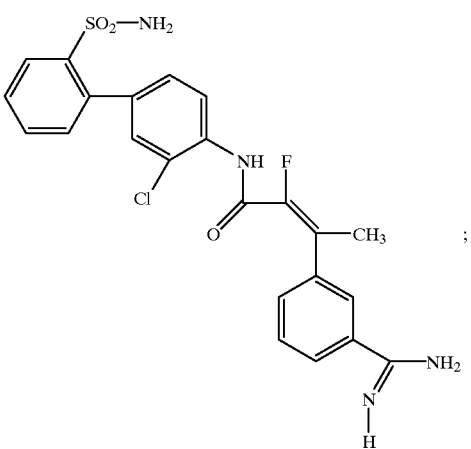
;
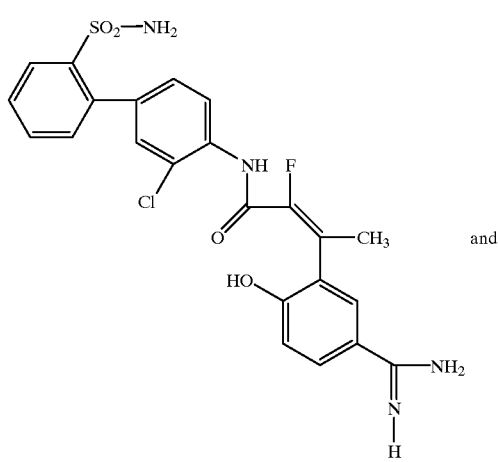
and

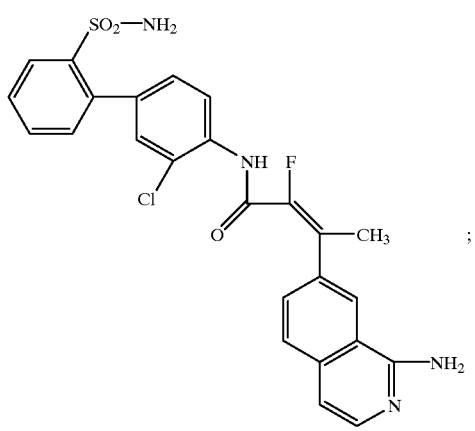

and all pharmaceutically acceptable isomers, salts, hydrates, solvates and prodrug derivatives thereof.

10. A compound according to claim 1, which is a member selected from the group consisting of:

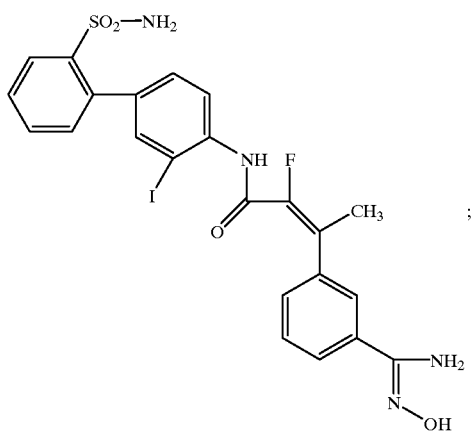

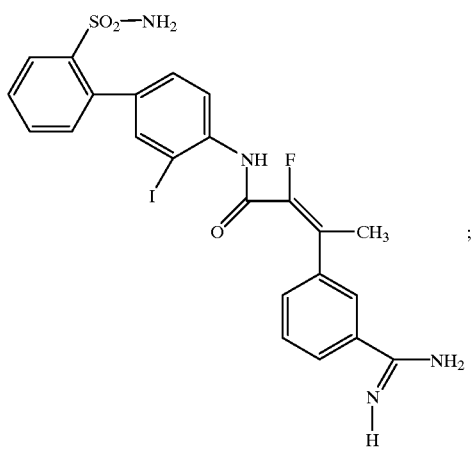

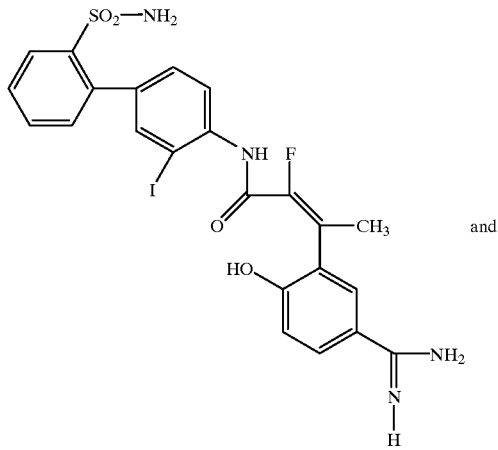

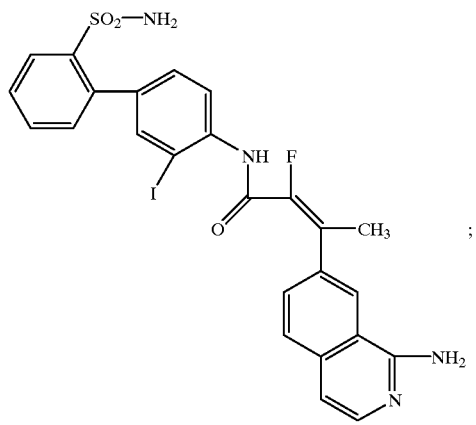

and all pharmaceutically acceptable isomers, salts, hydrates, solvates and prodrug derivatives thereof.

11. A compound according to claim 1, which is a member selected from the group consisting of:

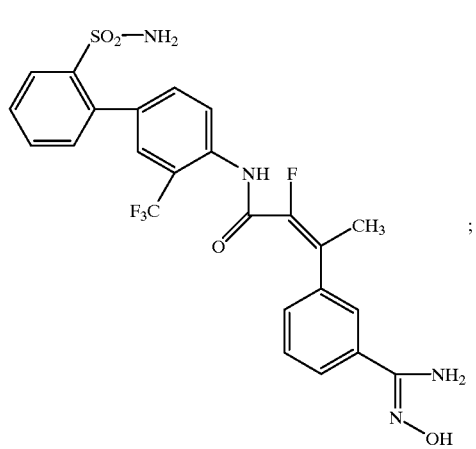

-continued
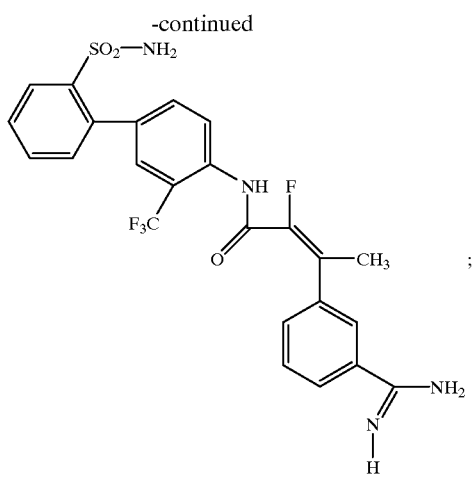
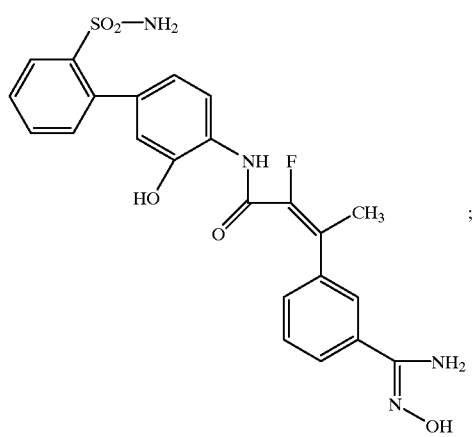
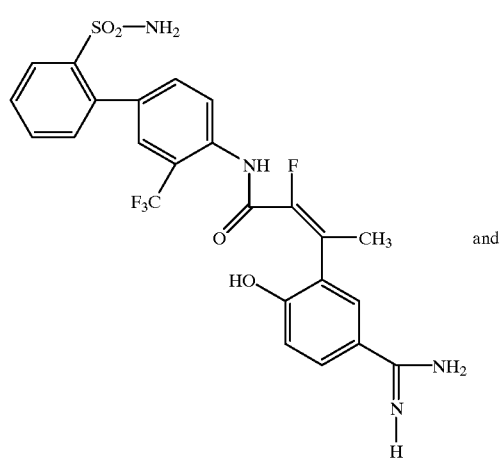
and
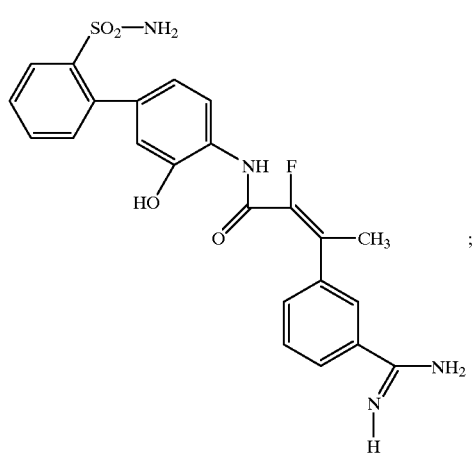
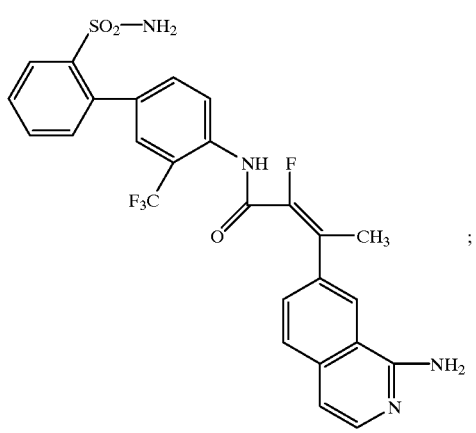
;
and all pharmaceutically acceptable isomers, salts, hydrates, solvates and prodrug derivatives thereof.
12. A compound according to claim 1, which is a member selected from the group consisting of:
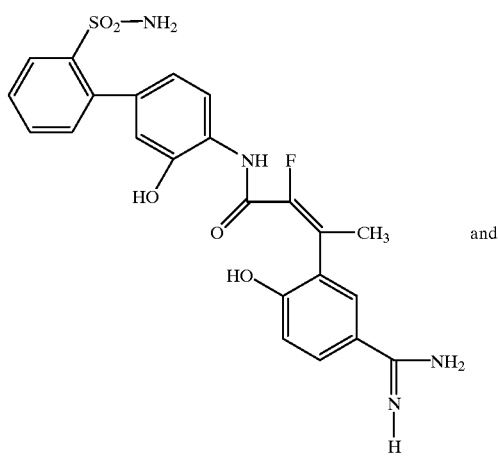
and -continued

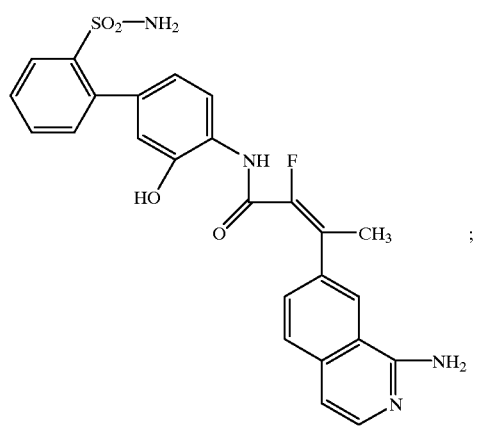

and all pharmaceutically acceptable isomers, salts, hydrates, solvates and prodrug derivatives thereof.

13. A compound according to claim 1, which is a member selected from the group consisting of:

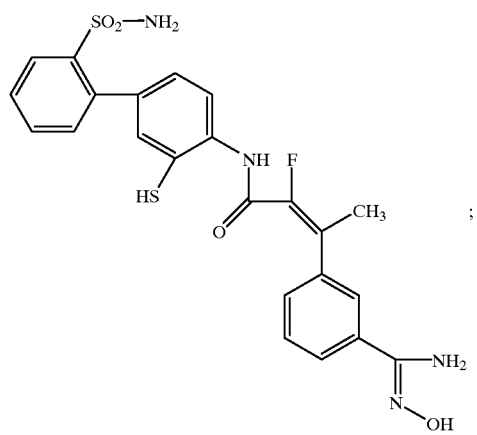

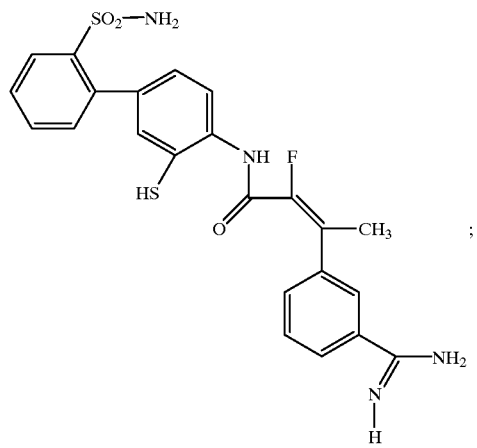

-continued

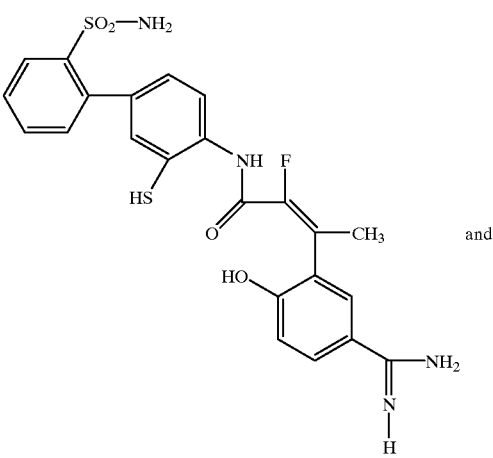

and

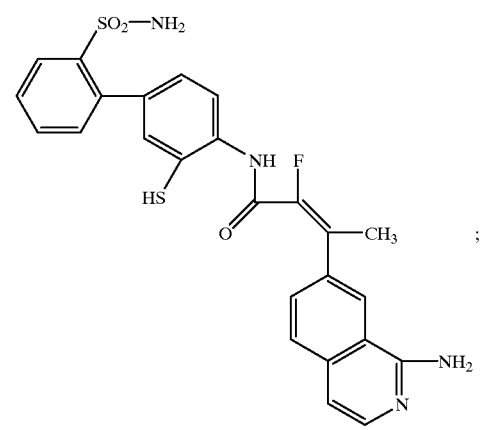

and all pharmaceutically acceptable isomers, salts, hydrates, solvates and prodrug derivatives thereof.

14. A compound according to claim 1, which is a member selected from the group consisting of:

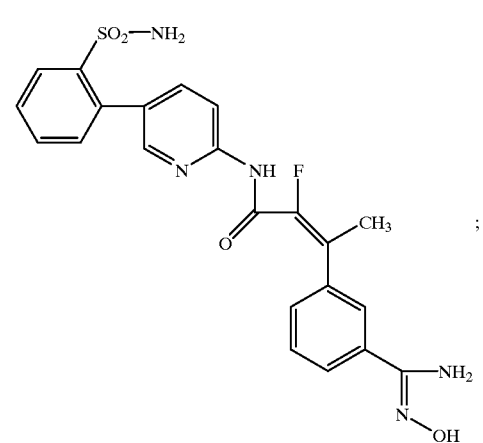

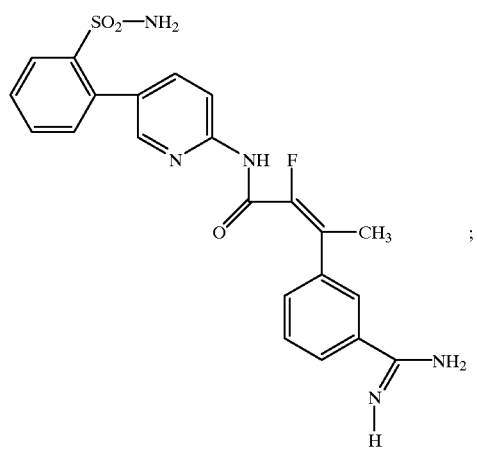
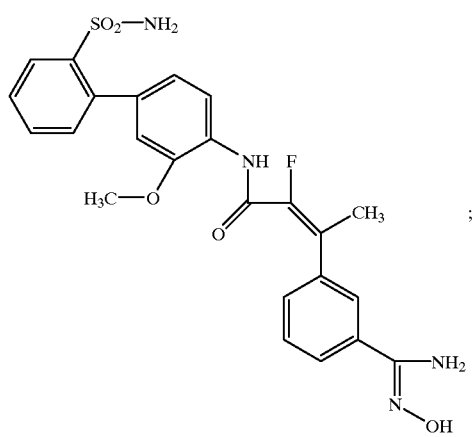
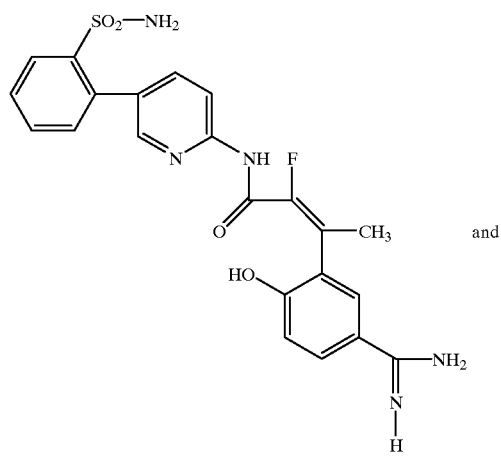
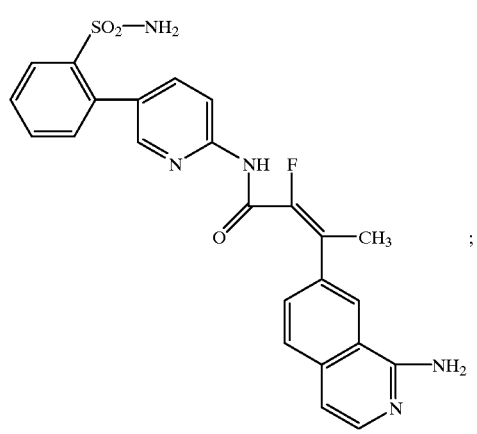
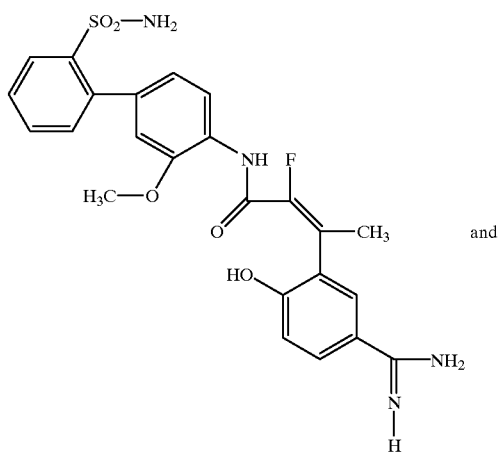
and all pharmaceutically acceptable isomers, salts, hydrates, solvates and prodrug derivatives thereof.
15. A compound according to claim 1, which is a member selected from the group consisting of:

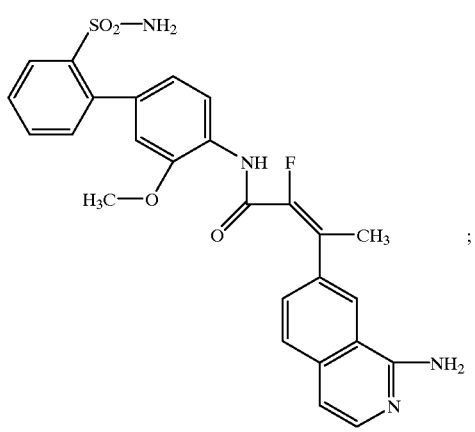
and all pharmaceutically acceptable isomers, salts, hydrates, solvates and prodrug derivatives thereof.
16. A compound according to claim 1, which is a member selected from the group consisting of:
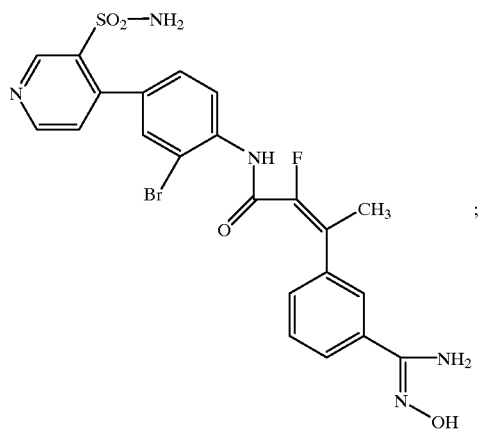
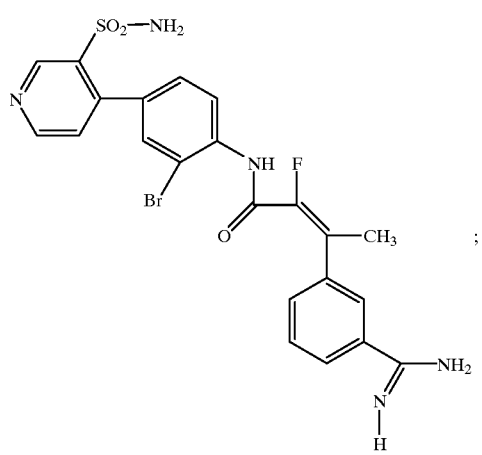
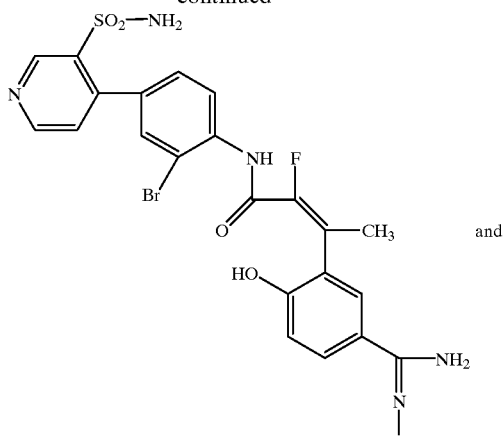
and
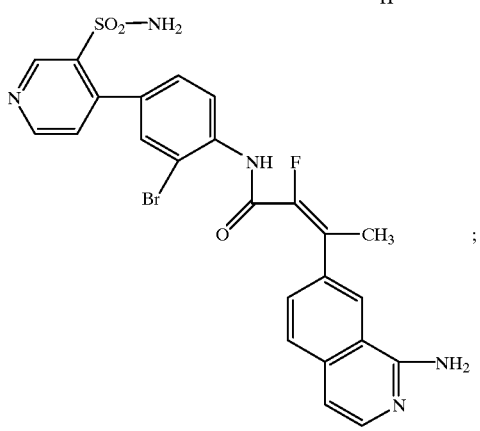
and all pharmaceutically acceptable isomers, salts, hydrates, solvates and prodrug derivatives thereof.
17. A compound according to claim 1, of the formula:
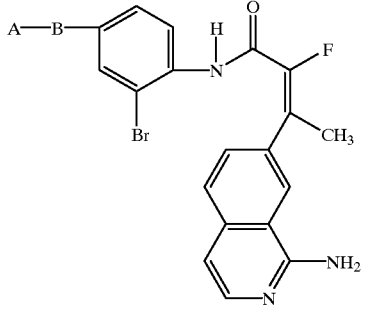
wherein A—B is:
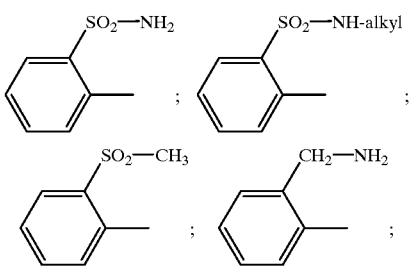

-continued
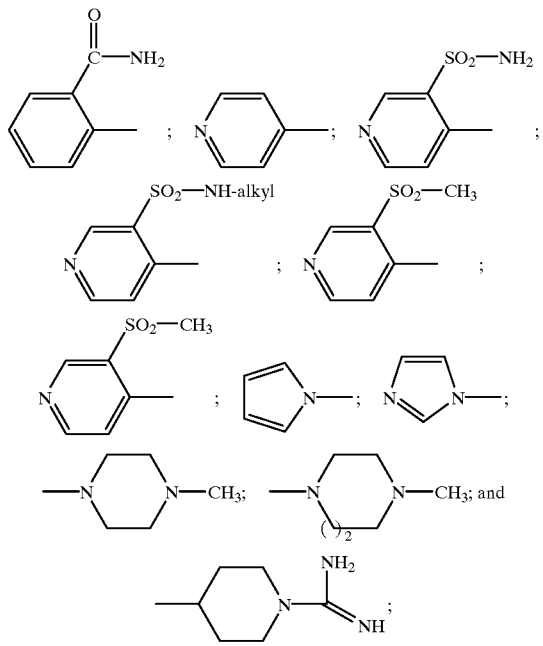
and all pharmaceutically acceptable isomers, salts, hydrates, solvates and prodrug derivatives thereof.
18. A compound according to claim 1, of the formula:
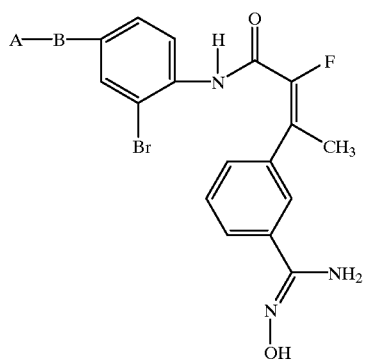
wherein A—B is:
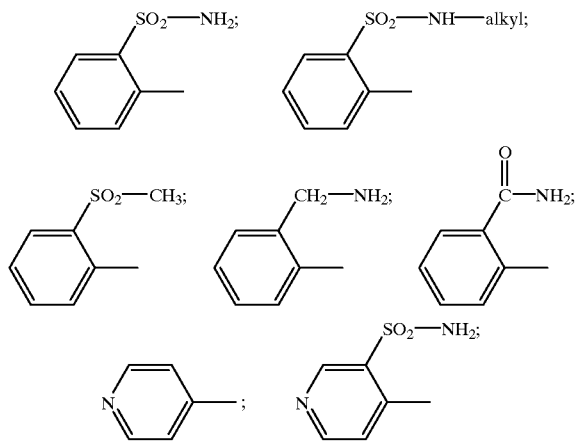
-continued
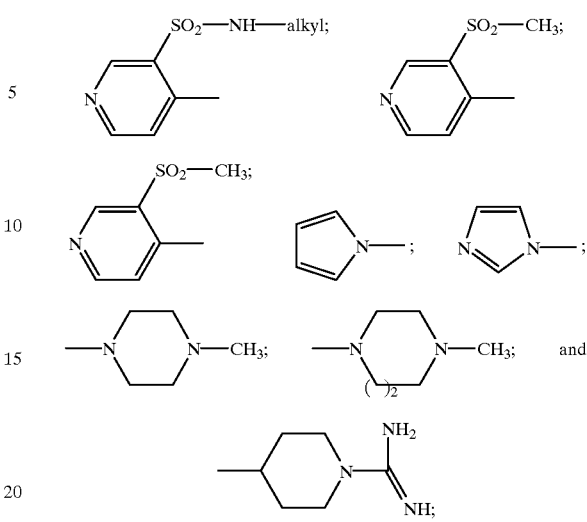
and all pharmaceutically acceptable isomers, salts, hydrates, solvates and prodrug derivatives thereof.
19. A compound according to claim 1, of the formula:
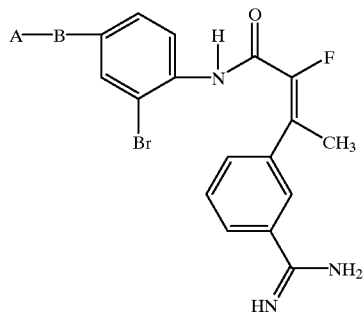
wherein A—B is:
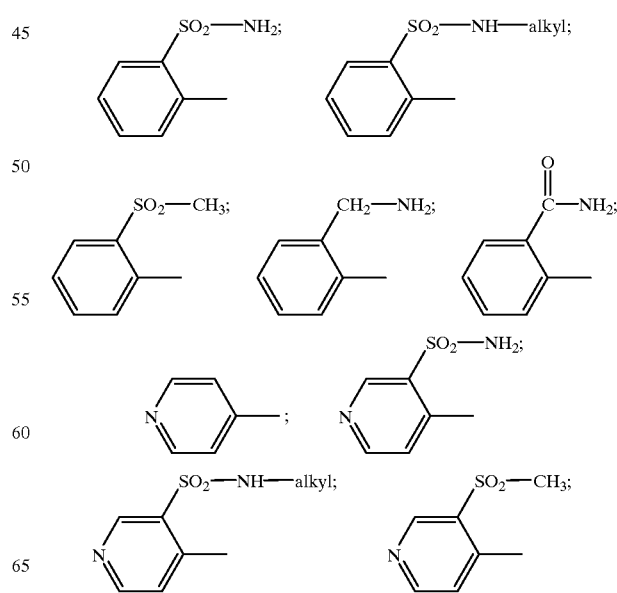

-continued
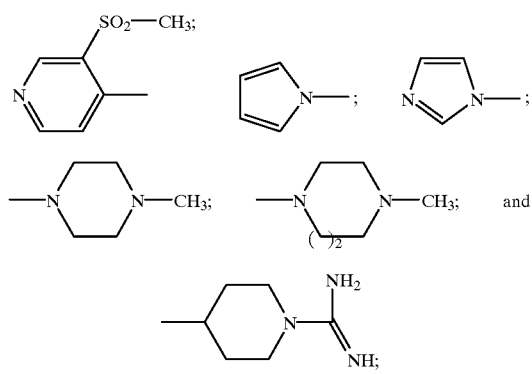
and all pharmaceutically acceptable isomers, salts, hydrates, solvates and prodrug derivatives thereof.
20. A compound according to claim 1, of the formula:
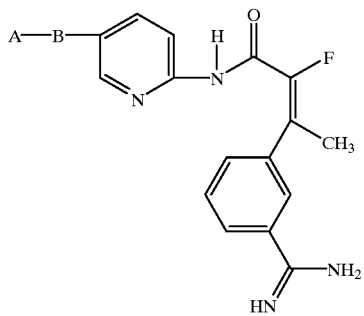
wherein A—B is:
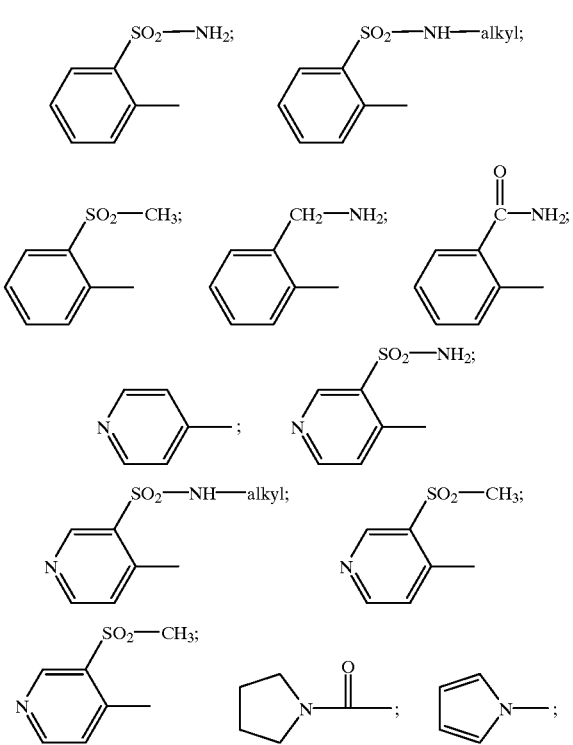
-continued
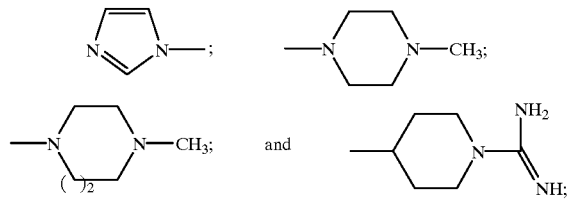
and all pharmaceutically acceptable isomers, salts, hydrates, solvates and prodrug derivatives thereof.
21. A compound according to claim 1, of the formula:
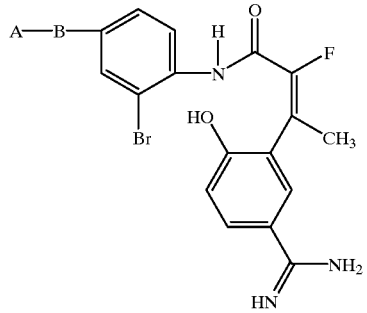
wherein A—B is:
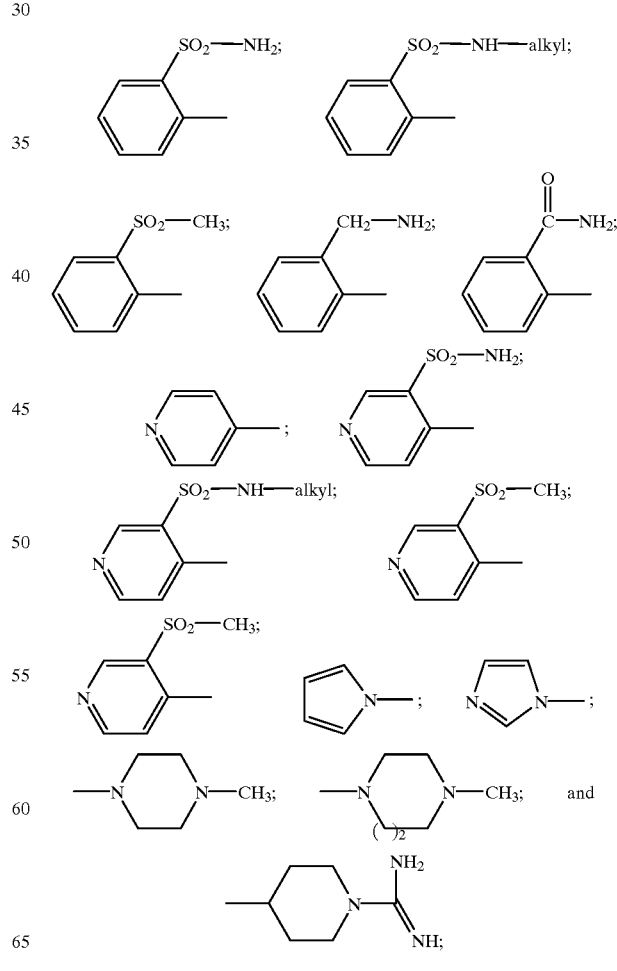

and all pharmaceutically acceptable isomers, salts, hydrates, solvates and prodrug derivatives thereof.

22. A pharmaceutical composition for treating a condition in a mammal characterized by undesired thrombosis comprising a therapeutically acceptable carrier and a therapeutically effective amount of a compound of claim 1.

23. A method for treating a condition in a mammal characterized by undesired thrombosis comprising administering to said mammal a therapeutically effective amount of a compound of claim 1.

24. The method of claim 23, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

25. A method for inhibiting the coagulation biological samples, comprising the administration of a compound of claim 1.

* * * * *

UNITED STATES PATENT AND TRADEMARK OFFICE
CERTIFICATE OF CORRECTION

PATENT NO.    : 6,399,627 B1
DATED         : June 4, 2002
INVENTOR(S)   : Song et al.

It is certified that error appears in the above-identified patent and that said Letters Patent is hereby corrected as shown below:

Column 152,
Line 29, replace "—C2-6alkynl," with -- $C_{2-6}$alkynl --.

Column 153,
Line 62, replace "$C_{-04}$alkyl$C_{3-8}$" with -- $C_{0-4}$alkyl$C_{3-8}$ --.

Column 156,
Line 23, replace "$R^{1a}$" with -- $R^4$ --

Column 157,
Line 56, replace "C1-$_6$alkyl" with -- $C_{1-6}$alkyl --

Column 160,
Approximately line 55, in the second chemical structure, replace "HN" with -- NH --.

Column 185,
Line 65, delete the second chemical structure.

Signed and Sealed this

Twenty-ninth Day of July, 2003

JAMES E. ROGAN
*Director of the United States Patent and Trademark Office*